US011742076B2

(12) United States Patent
Banerjee et al.

(10) Patent No.: US 11,742,076 B2
(45) Date of Patent: Aug. 29, 2023

(54) MACHINE LEARNING SYSTEMS FOR GENERATING MULTI-MODAL DATA ARCHETYPES

(71) Applicant: NEUMORA THERAPEUTICS, INC., San Francisco, CA (US)

(72) Inventors: Tathagata Banerjee, Waltham, MA (US); Matthew Edward Kollada, Deerfield, IL (US)

(73) Assignee: Neumora Therapeutics, Inc., San Francisco, CA (US)

( * ) Notice: Subject to any disclaimer, the term of this patent is extended or adjusted under 35 U.S.C. 154(b) by 0 days.

(21) Appl. No.: 17/960,755

(22) Filed: Oct. 5, 2022

(65) Prior Publication Data

US 2023/0107415 A1 Apr. 6, 2023

Related U.S. Application Data

(60) Provisional application No. 63/413,150, filed on Oct. 4, 2022, provisional application No. 63/400,250, filed
(Continued)

(51) Int. Cl.
*G16H 40/20* (2018.01)
*G16H 50/70* (2018.01)
(Continued)

(52) U.S. Cl.
CPC ............ *G16H 40/20* (2018.01); *G06N 3/02* (2013.01); *G06N 3/045* (2023.01); *G06N 3/08* (2013.01);
(Continued)

(58) Field of Classification Search
CPC ............ G06N 3/08; G06N 3/045; G06N 3/02; G16H 40/20; G16H 50/70; G16H 50/20;
(Continued)

(56) References Cited

U.S. PATENT DOCUMENTS 11,106,950 B2 * 8/2021 Kecskemethy ..... G06F 18/2411

OTHER PUBLICATIONS

Shen, D., et al, Deep Learning in Medical Image Analysis, [received on Apr. 4, 2023], Retrieved from Internet:<https://www.annualreviews.org/doi/abs/10.1146/annurev-bioeng-071516-044442> (Year: 2017).*
(Continued)

*Primary Examiner* — Miranda M Huang
*Assistant Examiner* — Bart I Rylander
(74) *Attorney, Agent, or Firm* — Fish & Richardson P.C.

(57) ABSTRACT

Methods, systems, and apparatus, including computer programs encoded on a computer storage medium, for generating multi-modal data archetypes. In one aspect, a method comprises obtaining a plurality of training examples, wherein each training example corresponds to a respective patient and includes multi-modal data, having a plurality of feature dimensions, that characterizes the patient; jointly training an encoder neural network and a decoder neural network on the plurality of training examples; and generating a plurality of multi-modal data archetypes that each correspond to a respective dimension of a latent space, comprising, for each multi-modal data archetype: processing a predefined embedding that represents the corresponding dimension of the latent space using the decoder neural network to generate multi-modal data, having the plurality of feature dimensions, that defines the multi-modal data archetype.

20 Claims, 40 Drawing Sheets

Related U.S. Application Data on Aug. 23, 2022, provisional application No. 63/337,753, filed on May 3, 2022, provisional application No. 63/328,189, filed on Apr. 6, 2022, provisional application No. 63/294,751, filed on Dec. 29, 2021, provisional application No. 63/292,115, filed on Dec. 21, 2021, provisional application No. 63/252,523, filed on Oct. 5, 2021, provisional application No. 63/252,539, filed on Oct. 5, 2021, provisional application No. 63/252,562, filed on Oct. 5, 2021, provisional application No. 63/252,500, filed on Oct. 5, 2021.

(51) Int. Cl.

| | |
|---|---|
| *G16H 50/20* | (2018.01) |
| *G06N 3/02* | (2006.01) |
| *G06N 3/045* | (2023.01) |
| *G06N 3/08* | (2023.01) |
| *G16H 30/40* | (2018.01) |
| *G06V 10/77* | (2022.01) |
| *G06V 10/82* | (2022.01) |
| *G06V 10/774* | (2022.01) |
| *G06T 7/00* | (2017.01) |
| *G06N 20/00* | (2019.01) |

(52) U.S. Cl.
CPC .......... *G06T 7/0016* (2013.01); *G06V 10/774* (2022.01); *G06V 10/7715* (2022.01); *G06V 10/82* (2022.01); *G16H 30/40* (2018.01); *G16H 50/20* (2018.01); *G16H 50/70* (2018.01); *G06N 20/00* (2019.01); *G06T 2207/10088* (2013.01); *G06T 2207/10104* (2013.01); *G06T 2207/20081* (2013.01); *G06T 2207/20084* (2013.01); *G06T 2207/30016* (2013.01); *G06T 2207/30104* (2013.01); *G06V 2201/03* (2022.01)

(58) Field of Classification Search
CPC .... G16H 30/40; G06V 10/7715; G06V 10/82; G06V 10/774; G06T 7/0016
See application file for complete search history.

(56) References Cited

OTHER PUBLICATIONS

Tran, D., et al., DeepCoder: Semi-parametric Variational Autoencoders for Automatic Facial Action Coding, [received on Apr. 4, 2023], Retrieved from Internet:<https://openaccess.thecvf.com/content_iccv_2017/html/Tran_DeepCoder_Semi-Parametric_Variational_ICCV_2017_paper.html> (Year: 2017).*
Park, J., et al, Deep-learned time-signal intensity pattern analysis using an autoencoder captures magnetic resonance perfusion heterogeneity for brain tumor differentiation, [received on Apr. 4, 2024], Retrieved from Internet:<https://www.nature.com/articles/s41598-020-78485-x> (Year: 2020).*
Ieracitano, C., et al., A novel multi-modal machine learning based approach for automatic classification of EEG recordings in dementia, [received on 4/4/42023], Retrieved from Internet:<https://www.sciencedirect.com/science/article/pii/S0893608019303983> (Year: 2020).*
Tian, J., et al, Towards Automatic Diagnosis from Multi-modal Medical Data, [received on Apr. 4, 2023], Retrieved from Internet:<https://link.springer.com/chapter/10.1007/978-3-030-33850-3_8> (Year: 2019).*
Eleftheriadis, S., et al., Variational Gaussian Process Auto-Encoder for Ordinal Prediction of Facial Action Units, [received on Apr. 4, 2023], Retrieved from Internet:< https://link.springer.com/chapter/10.1007/978-3-319-54184-6_10> (Year: 2017).*
Shen, D., et al, Deep Learning in Medical Image Analysis, [received on Apr. 4, 2023], Retrieved from Internet:<https://www.annualreviews.org/doi/abs/10.1146/annurev-bioeng-071516-044442> (Year: 2017).*
Tran, D., et al., DeepCoder: Semi-parametric Variational Autoencoders for Automatic Facial Action Coding, [received on Apr. 4, 2023], Retrieved from Internet:<https://openaccess.thecvf.com/content_iccv_2017/html/Tran_DeepCoder_Semi-Parametric_Variational_ICCV_2017_paper.html> (Year: 2017).*
Tahmassebi, A., et al., Deep Learning in Medical Imaging: fMRI Big Data Analysis via Convolutional Neural Networks, [received on Apr. 4, 2023], Retrieved from Internet:<https://dl.acm.org/doi/abs/10.1145/3219104.3229250> (Year: 2018).*
Goodwin, T., Multi-modal Patient Cohort Identification from EEG Report and Signal Data, [received May 24, 2023], Retrieved from Internet:<https://www.ncbi.nlm.nih.gov/pmc/articles/PMC5333290/> (Year: 2016).*
Banerjee et al., "Predicting mood disorder symptoms with remotely collected videos using an interpretable multimodal dynamic attention fusion network," Sep. 7, 2021, arXiv.2109.03029, 8 pages.
Gala et al., "A coupled autoencoder approach for multi-modal analysis of cell types," Nov. 6, 2019, arXiv, 1911.05663, 10 pages.
Ghosal et al., "G-MIND: an end-to-end multimodal imaging-genetics framework for biomarker identification and disease classification," Jan. 27, 2021, arXiv.2101.11656, 10 pages.
Ghosh et al., "Importance-based multimodal autoencoder," OpenReview.net, Sep. 28, 2020 (modified Mar. 6, 2021), Retrieved from URL<https://openreview.net/pdf?id=4jXnFYaDOuD, Retrieved on Dec. 20, 2022, 14 pages.
International Search Report and Written Opinion in International Appln. No. PCT/US2022/045815, dated Jan. 9, 2023, 16 pages.
Udandarao et al., "COBRA: contrastive bi-modal representation algorithm," May 24, 2020, arXiv.2005.03687, 13 pages.
Angelopoulos et al., "A Gentle Introduction to Conformal Prediction and Distribution-Free Uncertainty Quantification," Feb. 1, 2022, 43 pages.
Barber et al., "The Quickhull Algorithm for Convex Hulls," ACM Transactions on Mathematical Software, vol. 22, Issue 4, Dec. 1996, pp. 469-483.
Bates et al., "Distribution-free, risk-controlling prediction sets," arXiv preprint, Dec. 2021, 34 pages.
Brendel et al., "Comprehensive subtyping of Parkinson's disease patients with similarity fusion: a case study with BioFIND data," NPJ Parkinson's Disease, Sep. 17, 2021, 9 pages.
Chen et al., "InfoGAN: Interpretable Representation Learning by Information Maximizing Generative Adversarial Nets," UC Berkeley, Department of Electrical Engineering and Computer Sciences, Jun. 12, 2016, 14 pages.
Edelsbrunner, "Alpha shapes—a survey," Tessellations in the Sciences: Virtues, Techniques and Applications of Geometric Tilings, Springer, 2011, 25 pages.
Goodfellow et al., "Generative adversarial nets," Advances in neural information processing systems, Jun. 2014, 9 pages.
Havaei et al., "Conditional generation of medical images via disentangled adversarial inference," Medical Image Analysis, Aug. 2021, 22 pages.
Higgins et al., "beta-vae: Learning basic visual concepts with a constrained variational framework," ICLR Poster, Nov. 4, 2016, 22 pages.
Hu et al., "Learning discrete representations via information maximizing selfaugmented training," International conference on machine learning, Aug. 2017, pp. 1558-1567.
Kingma et al., "Semi-supervised learning with deep generative models," Advances in neural information processing systems, Jun. 2014, pp. 3581-3589.
Kurutach et al., "Learning plannable representations with causal infogan," arXiv preprint, 2018, 19 pages.
Mirza et al., "Conditional generative adversarial nets," arXiv preprint, Nov. 2014, 7 pages.
Monnier et al., "Deep transformation-invariant clustering," arXiv preprint, Jun. 2020, 14 pages.

(56) References Cited

OTHER PUBLICATIONS

Monti et al., "Consensus clustering: a resampling-based method for class discovery and visualization of gene expression microarray data," Machine learning, 2003, 52(1):91-118.

Moreira et al., "Concave hull: a k-nearest neighbors approach for the computation of the region occupied by a set of points," International Conference on Computer Graphics Theory and Applications, Jan. 2007, pp. 61-68.

Mukherjee et al., "Clustergan: Latent space clustering in generative adversarial networks," AAAI Conference on Artificial Intelligence, 2019, vol. 33, pp. 4610-4617.

Radford et al., "Unsupervised representation learning with deep convolutional generative adversarial networks," arXiv preprint, Nov. 2015, 16 pages.

Wu et al., "Multimodal Generative Models for Scalable Weakly-Supervised Learning," 32nd Conference on Neural Information Processing Systems, Feb. 14, 2018, 19 pages.

Xie et al., "Unsupervised deep embedding for clustering analysis," PMLR, International conference on machine learning, 2016, pp. 478-487.

Yang et al., "Joint unsupervised learning of deep representations and image clusters," IEEE conference on computer vision and pattern recognition, Jun. 2016, pp. 5147-5156.

Zhou et al., "Graph neural networks: a review of methods and applications," AI Open, vol. 1, 2020, pp. 57-81.

\* cited by examiner

US 11,742,076 B2

MACHINE LEARNING SYSTEMS FOR GENERATING MULTI-MODAL DATA ARCHETYPES

RELATED APPLICATIONS

This application claims priority to U.S. provisional application No. 63/252,523, filed Oct. 5, 2011; U.S. provisional application No. 63/252,539, filed Oct. 5, 2021; U.S. provisional application No. 63/252,562, filed Oct. 5, 2021; U.S. provisional application No. 63/252,500, filed Oct. 5, 2021; U.S. provisional application No. 63/292,115, filed Dec. 21, 2021, U.S. provisional application No. 63/294,751, filed Dec. 29, 2021; U.S. provisional application No. 63/328,189, filed Apr. 6, 2022; U.S. provisional application No. 63/337,753, filed May 3, 2022; U.S. provisional application No. 63/400,250, filed Aug. 23, 2022; and U.S. provisional application No. 63/413,150, filed Oct. 4, 2022, all of which are incorporated herein by reference.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a machine learning system implemented as computer programs on one or more computers in one or more locations for processing multi-modal data characterizing patients.

Throughout this specification, a data "modality" refers to a type of data, e.g., that is generated using a specified sensor or medical diagnostic technique, and "multi-modal" data refers to a collection of data from multiple different modalities. An "embedding" refers to an ordered collection of numerical values, e.g., a vector, matrix, or other tensor of numerical values. The term "patient" is used interchangeably with the term "subject."

Throughout this specification, a first set of elements is referred to as a "proper" subset of a second set of elements if: (i) the first set is a subset of the second set, and (ii) the first set includes fewer than all of the elements in the second set.

According to a first aspect, there is provided a method comprising: receiving multi-modal data characterizing a patient, wherein the multi-modal data comprises a respective feature representation for each of a plurality of modalities; processing the multi-modal data characterizing the patient using an encoder neural network to generate an embedding of the multi-modal data characterizing the patient; determining a respective classification score for each patient category in a set of patient categories based on the embedding of the multi-modal data characterizing the patient; and classifying the patient as being included in a corresponding patient category from the set of patient categories based on the classification scores.

In some implementations, the method further comprises, prior to receiving the multi-modal data characterizing the patient, determining the set of patient categories based on a set of training patients; wherein determining the set of patient categories based on the set of training patients comprises: receiving respective multi-modal data characterizing each training patient in the set of training patients; generating a set of training embeddings that each correspond to a respective training patient, wherein generating the training embedding for a training patient comprises processing the multi-modal data characterizing the training patient using the encoder neural network; and determining a partition of the set of training embeddings into a set of clusters of training embeddings, wherein each cluster of training embeddings comprises a plurality of training embeddings and represents a respective patient category.

In some implementations, determining the partition of the set of training embeddings into the set of clusters of training embeddings comprises: applying a clustering operation to the set of training embeddings to partition the set of training embeddings into the set of clusters of training embeddings.

In some implementations, each training patient is identified as being included in a patient category represented by the cluster of training embeddings that includes the training embedding for the training patient.

In some implementations, the method further comprises: determining, based on the classification of the patient as being included in the corresponding patient category, that the patient should receive a particular medical treatment.

In some implementations, the method further comprises applying the particular medical treatment to the patient in response to determining that the patient should receive the particular medical treatment.

In some implementations, the patient category that includes the patient also includes a plurality of training patients, wherein each training patient is associated with a respective class from a set of classes, and determining that the patient should receive the particular medical treatment comprises: determining a class distribution for the patient category that defines, for each class in the set of classes, a respective fraction of training patients included in the patient category that are associated with the class; and determining that the patient should receive the particular medical treatment based on the class distribution for the patient category.

In some implementations, the set of classes includes a first class and a second class, wherein each training patient associated with the first class is classified as having responded to the particular medical treatment when the particular medical treatment was applied to the training patient, and wherein each training patient associated with the second class is classified as having not responded to the particular medical treatment when the particular medical treatment was applied to the training patient.

In some implementations, determining the respective classification score for each patient category in the set of patient categories based on the embedding of the multi-modal data characterizing the patient comprises: processing the embedding of the multi-modal data characterizing the patient using a classification machine learning model to generate the respective classification score for each patient category in the set of patient categories; wherein the classification machine learning model has been trained on a set of training examples, wherein each training example corresponds to a respective training patient from the set of training patients and comprises: (i) the training embedding for the training patient, and (ii) a label identifying a respective patient category of the training patient.

In some implementations, determining the respective classification score for each patient category in the set of patient categories based on the embedding of the multi-modal data characterizing the patient comprises, for each patient category: determining a centroid embedding for the patient category as a combination of each training embedding in the cluster of training embeddings represented by the patient category; and determining the classification score for the patient category based on a similarity measure between: (i) the embedding of the multi-modal data characterizing the patient, and (ii) the centroid embedding for the patient category.

In some implementations, the encoder neural network includes a respective encoder subnetwork corresponding to each modality of the plurality of modalities, and processing the multi-modal data characterizing the patient using the encoder neural network to generate the embedding of the multi-modal data characterizing the patient comprises: processing, for each of the plurality of modalities, the respective feature representation for the modality using the corresponding encoder subnetwork of the encoder neural network to generate a respective encoder subnetwork output; and combining the respective encoder subnetwork output of each encoder subnetwork to generate the embedding of the multi-modal data characterizing the patient.

In some implementations, the encoder neural network has been jointly trained with a decoder neural network, wherein jointly training the decoder neural network comprises, for each training patient in a set of training patients: processing training multi-modal data characterizing the training patient using the encoder neural network, in accordance with current values of a set of encoder neural network parameters, to generate an embedding of the training multi-modal data characterizing the training patient; processing the embedding of the training multi-modal data characterizing the training patient using the decoder neural network, in accordance with current values of a set of decoder neural network parameters, to generate a reconstruction of the training multi-modal data characterizing the training patient; and updating the current values of the set of encoder neural network parameters and the current values of the set of decoder neural network parameters using gradients of a reconstruction loss function that measures an error in the reconstruction of the training multi-modal data characterizing the training patient.

In some implementations, the reconstruction loss function comprises a plurality of scaling factors that each scale a respective term in the reconstruction loss function that measures an error in the reconstruction of a corresponding proper subset of a set of feature dimensions of the training multi-modal data characterizing the training patient; and each of the plurality of scaling factors has a respective value that is based on a relevance of the corresponding proper subset of the set of feature dimensions of the training multi-modal data to a medical condition.

In some implementations, the respective value of each of the plurality of scaling factors is based on a relevance of the corresponding proper subset of the set of feature dimensions to a treatment for the medical condition.

In some implementations, for one or more feature dimensions, the reconstruction loss comprises a respective scaling factor corresponding to the feature dimension and a value of the scaling factor corresponding to the feature dimension is determined by operations comprising: obtaining, for each of one or more reference patients: (i) a pre-treatment value of a feature corresponding to the feature dimension that is measured for the reference patient prior to the reference patient receiving the treatment, and (ii) a post-treatment value of the feature corresponding to the feature dimension that is measured for the reference patient after the reference patient receives the treatment; and determining the value of the scaling factor corresponding to the feature dimension based on, for each reference patient, the pre-treatment value and the post-treatment value corresponding to the feature dimension for the reference patient.

In some implementations, classifying the patient as being included in a corresponding patient category from the set of patient categories based the classification scores comprises: classifying the patient as being included in a patient category with a highest classification score.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

In some implementations, the plurality of modalities include a clinical scale modality, and the feature representation of the clinical scale modality represents data obtained from a clinical interview with the patient.

In some implementations, the plurality of modalities include an electroencephalography (EEG) modality, and the feature representation of the EEG modality is derived from a plurality of voltage waveforms that are each measured by a respective electrode placed in proximity to a brain of the patient.

In some implementations, the plurality of modalities include a genomics modality, and the feature representation of the genomics modality is derived from data defining a sequence of nucleotides from a genome of the patient.

In some implementations, the plurality of modalities include an audio modality, and the feature representation of the audio modality is derived from audio data that represents a sequence of words spoken by the patient.

According to another aspect, there is provided a method comprising: obtaining a plurality of training examples, wherein each training example corresponds to a respective patient and includes multi-modal data, having a plurality of feature dimensions, that characterizes the patient; jointly training an encoder neural network having a set of encoder parameters and a decoder neural network having a set of decoder parameters on the plurality of training examples, comprising, for each training example: processing the multi-modal data from the training example using the encoder neural network, in accordance with current values of the encoder parameters, to generate an embedding of the multi-modal data from the training example; processing the embedding of the multi-modal data from the training example using the decoder neural network, in accordance with current values of the decoder parameters, to generate a reconstruction of the multi-modal data from the training example; and updating the current values of the set of encoder parameters and the current values of the set of decoder parameters using gradients of a reconstruction loss function that measures an error in the reconstruction of the multi-modal data from the training example, wherein: the reconstruction loss function comprises a plurality of scaling factors that each scale a respective term in the reconstruction loss function that measures an error in the reconstruction of a corresponding proper subset of the feature dimensions of the multi-modal data from the training example, and each of the plurality of scaling factors has a respective value that is based on a relevance of the corresponding proper subset of the feature dimensions of the multi-modal data from the training example to a particular medical condition.

In some implementations, the respective value of each of the plurality of scaling factors is based on a relevance of the corresponding proper subset of the feature dimensions of the multi-modal data from the training example to a treatment for the particular medical condition.

In some implementations, for one or more feature dimensions, the reconstruction loss comprises a respective scaling factor corresponding to the feature dimension and a value of the scaling factor corresponding to the feature dimension is determined by operations comprising: obtaining, for each of one or more reference patients: (i) a pre-treatment value of a feature corresponding to the feature dimension that is measured for the reference patient prior to the reference patient receiving the treatment, and (ii) a post-treatment value of the feature corresponding to the feature dimension that is measured for the reference patient after the reference patient receives the treatment; and determining the value of the scaling factor corresponding to the feature dimension based on, for each reference patient, the pre-treatment value and the post-treatment value corresponding to the feature dimension for the reference patient.

In some implementations, determining the value of the scaling factor corresponding to the feature dimension based on, for each reference patient, the pre-treatment value and the post-treatment value corresponding to the feature dimension for the reference patient comprises: determining a set of difference values, wherein each difference value represents a difference between the pre-treatment value and the post-treatment value corresponding to the feature dimension for a respective reference patient; determining a measure of central tendency of the set of difference values; and determining the value of the scaling factor corresponding to the feature dimension based on the measure of central tendency of the set of difference values.

In some implementations, determining a measure of central tendency of the set of difference values comprises: determining a mean or median of the set of difference values.

In some implementations, determining the value of the scaling factor corresponding to the feature dimension based on the measure of central tendency of the set of difference values comprises: determining the value of the scaling factor corresponding to the feature dimension based on an absolute value of the measure of central tendency of the set of difference values.

In some implementations, the treatment for the particular medical condition comprises a drug, and for each of one or more of the scaling factors: the proper subset of the feature dimensions corresponding to the scaling factor characterize a brain region in a brain parcellation; and a value of the scaling factor is determined by based on a positron emission tomography (PET) image of a brain of a reference patient that is captured after the drug has been labelled with a radiotracer and administered to the reference patient.

In some implementations, determining the value of the scaling factor based on the PET image of the brain of the reference patient comprises: determining a penetration score for the brain region that characterizes a concentration of the drug in the brain region in the brain of the reference patient based on a measure of central tendency of intensities of voxels included in the brain region in the PET image of the brain of the reference patient; and determining the value of the scaling factor based on the penetration score for the brain region.

In some implementations, for one or more feature dimensions, the reconstruction loss comprises a respective scaling factor corresponding to the feature dimension and a value of the scaling factor corresponding to the feature dimension is determined by operations comprising: obtaining, for each reference patient in a set of reference patients: (i) a value of a feature corresponding to the feature dimension that is measured for the reference patient, and (ii) a label indicating whether the reference patient has been diagnosed with the medical condition; determining a correlation between values of the feature corresponding to the feature dimension and diagnosis with the medical condition; and determining the scaling factor corresponding to the feature dimension based on the correlation between values of the feature corresponding to the feature dimension and diagnosis with the medical condition.

In some implementations, the treatment for the particular medical condition involves administering a drug to treat the particular medical condition.

In some implementations, scaling factors corresponding to proper subsets of the feature dimensions of the multi-modal data that are more relevant to the particular medical condition have higher values than scaling factors corresponding to proper subsets of the feature dimensions of the multi-modal data that are less relevant to the particular medical condition.

In some implementations, the particular medical condition is a psychiatric medical condition.

In some implementations, for each training example, processing the multi-modal data from the training example using the encoder neural network to generate the embedding of the multi-modal data from the training example comprises: processing the multi-modal data from the training example to generate parameters defining a posterior probability distribution over a latent space; and sampling the embedding of the multi-modal data from the training example in accordance with the posterior probability distribution over the latent space.

In some implementations, the multi-modal data from each training example comprises a respective feature representation for each of a plurality of modalities, the encoder neural network includes a respective encoder subnetwork corresponding to each modality of the plurality of modalities, and for each training example, processing the multi-modal data from the training example to generate the posterior probability distribution over the latent space comprises: processing, for each of the plurality of modalities, the respective feature representation for the modality using the corresponding encoder subnetwork of the encoder neural network to generate a respective encoder subnetwork output; and combining the respective encoder subnetwork output of each encoder subnetwork to generate the parameters defining the posterior probability distribution over the latent space.

In some implementations, the decoder neural network includes a respective decoder subnetwork corresponding to each modality of the plurality of modalities, and for each training example, processing the embedding of the multi-modal data from the training example to generate the reconstruction of the multi-modal data from the training example comprises: processing, for each of the plurality of modalities, the embedding of the multi-modal data from the training example using the corresponding decoder subnetwork of the decoder neural network to generate a reconstruction of the feature representation for the modality.

In some implementations, for each training example, the multi-modal data from the training example comprises a respective feature representation for each of a plurality of modalities.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

In some implementations, the plurality of modalities include a clinical scale modality, and the feature representation of the clinical scale modality represents data obtained from a clinical interview with the patient.

According to another aspect, there is provided a method comprising: obtaining a plurality of training examples, wherein each training example corresponds to a respective patient and includes multi-modal data, having a plurality of feature dimensions, that characterizes the patient; jointly training an encoder neural network and a decoder neural network on the plurality of training examples, wherein: the encoder neural network is configured to process input multi-modal data characterizing an input patient to generate an embedding of the input multi-modal data in a multi-dimensional latent space; and the decoder neural network is configured to process the embedding of the input multi-modal data to generate a reconstruction of the input multi-modal data; and generating a plurality of multi-modal data archetypes that each correspond to a respective dimension of the latent space, comprising, for each multi-modal data archetype: processing a predefined embedding that represents the corresponding dimension of the latent space using the decoder neural network to generate multi-modal data, having the plurality of feature dimensions, that defines the multi-modal data archetype.

In some implementations, the method further comprises generating a respective representation of each of the plurality of multi-modal data archetypes, comprising, for each multi-modal data archetype: generating a respective intensity score for each of the plurality of feature dimensions of the multi-modal data archetype based on: (i) a value of the feature dimension of the multi-modal data archetype, and (ii) a distribution defined by values of the feature dimension of multi-modal data included in the plurality of training examples; wherein the representation of the multi-modal data archetype comprises the respective intensity score for each of the plurality of feature dimensions of the multi-modal data archetype.

In some implementations, for each of the plurality of feature dimensions of the multi-modal data archetype, the intensity score for the feature dimension characterizes a likelihood of the value of the feature dimension of the multi-modal data archetype under the distribution defined by values of the feature dimension of multi-modal data included in the plurality of training examples.

In some implementations, for each of the plurality of feature dimensions of the multi-modal data archetype, determining the intensity score for the feature dimension comprises: determining a mean and a standard deviation of the distribution defined by values of the feature dimension of multi-modal data included in the plurality of training examples; and determining the intensity score for the feature dimension using the mean and the standard deviation of the distribution defined by values of the feature dimension of multi-modal data included in the plurality of training examples.

In some implementations, the method further comprises providing the representations of the multi-modal data archetypes as explainability data that explains the dimensions of the latent space.

In some implementations, the predefined embeddings that represent the dimensions of the latent space define a set of basis embeddings for the latent space, wherein each latent embedding in the latent space can be expressed as a linear combination of the set of basis embeddings for the latent space.

In some implementations, for each dimension of the latent space, the predefined embedding representing the dimension of the latent space is a unit embedding having: (i) a non-zero value in the dimension, and (ii) a zero value in each other dimension.

In some implementations, jointly training the encoder neural network and the decoder neural network comprises, for each training example: processing the multi-modal data from the training example using the encoder neural network, in accordance with current values of the encoder parameters, to generate an embedding of the multi-modal data from the training example; processing the embedding of the multi-modal data from the training example using the decoder neural network, in accordance with current values of the decoder parameters, to generate a reconstruction of the multi-modal data from the training example; and updating the current values of the set of encoder parameters and the current values of the set of decoder parameters using gradients of a reconstruction loss function that measures an error in the reconstruction of the multi-modal data from the training example, wherein: the reconstruction loss function comprises a plurality of scaling factors that each scale a respective term in the reconstruction loss function that measures an error in the reconstruction of a corresponding proper subset of the feature dimensions of the multi-modal data from the training example, and each of the plurality of scaling factors has a respective value that is based on a relevance of the corresponding proper subset of the feature dimensions of the multi-modal data from the training example to a particular medical condition.

In some implementations, the respective value of each of the plurality of scaling factors is based on a relevance of the corresponding proper subset of the feature dimensions of the multi-modal data from the training example to diagnosing the particular medical condition.

In some implementations, the respective value of each of the plurality of scaling factors is based on a relevance of the corresponding proper subset of the feature dimensions of the multi-modal data from the training example to a treatment for the particular medical condition.

In some implementations, scaling factors corresponding to proper subsets of the feature dimensions of the multi-modal data that are more relevant to the particular medical condition have higher values than scaling factors corresponding to proper subsets of the feature dimensions of the multi-modal data that are less relevant to the particular medical condition.

In some implementations, jointly training the encoder neural network and the decoder neural network comprises, for each latent dimension in a proper subset of a plurality of latent dimensions of the latent space: obtaining multi-modal data that defines a target multi-modal data archetype, having a plurality of feature dimensions, that corresponds to the latent dimension; processing a predefined embedding that represents the latent dimension using the decoder neural network to generate multi-modal data, having the plurality of feature dimensions, that defines a predicted multi-modal data archetype corresponding to the latent dimension; and updating the values of the set of decoder parameters using gradients of a loss function that measures an error between: (i) the predicted multi-modal data archetype corresponding to the latent dimension, and (ii) the target multi-modal data archetype corresponding to the latent dimension.

In some implementations, for each training example, the multi-modal data from the training example comprises a respective feature representation for each of a plurality of modalities.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

In some implementations, the plurality of modalities include an electroencephalography (EEG) modality, and the feature representation of the EEG modality is derived from a plurality of voltage waveforms that are each measured by a respective electrode placed in proximity to a brain of the patient.

In some implementations, the plurality of modalities include a genomics modality, and the feature representation of the genomics modality is derived from data defining a sequence of nucleotides from a genome of the patient.

In some implementations, the method further comprises: processing the plurality of multi-modal data archetypes to identify one or more dimensions to be removed from the latent space; and removing the identified dimensions from the latent space.

In some implementations, processing the plurality of multi-modal data archetypes to identify one or more dimensions to be removed from the latent space comprises, for each multi-modal data archetype: determining whether a value of a feature dimension of the multi-modal data archetype satisfies a threshold; and determining whether a corresponding dimension of the latent space should be removed based at least in part on the whether the value of the feature dimension of the multi-modal data archetype satisfies the threshold.

According to another aspect, there is provided a method comprising: obtaining a plurality of training examples, wherein each training example corresponds to a respective patient and includes multi-modal data that characterizes the patient; and jointly training an encoder neural network and a decoder neural network on the plurality of training examples, wherein: the encoder neural network is configured to process input multi-modal data characterizing an input patient, in accordance with values of a set of encoder parameters, to generate an embedding of the input multi-modal data in a latent space having a plurality of latent dimensions; and the decoder neural network is configured to process the embedding of the input multi-modal data, in accordance with values of a set of decoder parameters, to generate a reconstruction of the input multi-modal data; wherein the training comprises, for each latent dimension in a proper subset of the plurality of latent dimensions of the latent space: obtaining multi-modal data that defines a target multi-modal data archetype, having a plurality of feature dimensions, that corresponds to the latent dimension; processing a predefined embedding that represents the latent dimension using the decoder neural network to generate multi-modal data, having the plurality of feature dimensions, that defines a predicted multi-modal data archetype corresponding to the latent dimension; and updating the values of the set of decoder parameters using gradients of an archetype loss function that measures an error between: (i) the predicted multi-modal data archetype corresponding to the latent dimension, and (ii) the target multi-modal data archetype corresponding to the latent dimension.

In some implementations, for each latent dimension in the proper subset of the plurality of latent dimensions of the latent space, the predefined embedding that represents the latent dimension is a basis embedding from a set of basis embeddings that define a basis of the latent space, wherein each latent embedding in the latent space can be expressed as a linear combination of the set of basis embeddings.

In some implementations, for each latent dimension in the proper subset of the plurality of latent dimensions of the latent space, the predefined embedding that represents the latent dimension is a unit embedding having: (i) a non-zero value in the latent dimension, and (ii) a zero value in each other dimension.

In some implementations, the training further comprises, for each latent dimension in the proper subset of the plurality of latent dimensions of the latent space: processing the multi-modal data that defines the target multi-modal data archetype corresponding to the latent dimension using the encoder neural network to generate an embedding of the target multi-modal data archetype corresponding to the latent dimension; and updating the values of the set of encoder parameters using gradients of the archetype loss, wherein the archetype loss further measures an error between: (i) the embedding of the target multi-modal data archetype corresponding to the latent dimension, and (ii) the predefined embedding that represents the latent dimension.

In some implementations, obtaining the target multi-modal data archetypes comprises, prior to training the decoder neural network using the archetype loss function: jointly training the encoder neural network and the decoder neural network on the plurality of training examples over one or more initial training iterations to optimize an objective function that excludes the archetype loss function; processing, for each of the plurality of latent dimensions of the latent space, a predefined embedding that represents the latent dimension using the decoder neural network to generate multi-modal data that defines a candidate multi-modal data archetype corresponding to the latent dimension; and identifying one or more of the candidate multi-modal data archetypes as being target multi-modal data archetypes.

In some implementations, identifying one or more of the candidate multi-modal data archetypes as being target multi-modal data archetypes comprises: providing, to a user, a respective representation of each candidate multi-modal data archetype; and receiving, from the user, data selecting one or more of the candidate multi-modal data archetypes as target multi-modal data archetypes.

In some implementations, for each latent dimension in the proper subset of the plurality of latent dimensions of the latent space, the archetype loss function comprises a plurality of scaling factors that each scale a respective term in the archetype loss function that measures an error between: (i) the predicted multi-modal data archetype corresponding to the latent dimension, and (ii) the target multi-modal data archetype corresponding to the latent dimension, along a corresponding proper subset of the feature dimensions.

In some implementations, each of the plurality of scaling factors has a respective value that is based on a relevance of the corresponding proper subset of the feature dimensions to a particular medical condition.

In some implementations, the respective value of each of the plurality of scaling factors is based on a relevance of the corresponding proper subset of the feature dimensions to a treatment for the particular medical condition.

In some implementations, for one or more feature dimensions, the reconstruction loss comprises a respective scaling factor corresponding to the feature dimension and a value of the scaling factor corresponding to the feature dimension is determined by operations comprising: obtaining, for each of one or more reference patients: (i) a pre-treatment value of a feature corresponding to the feature dimension that is measured for the reference patient prior to the reference patient receiving the treatment, and (ii) a post-treatment value of the feature corresponding to the feature dimension that is measured for the reference patient after the reference patient receives the treatment; and determining the value of the scaling factor corresponding to the feature dimension based on, for each reference patient, the pre-treatment value and the post-treatment value corresponding to the feature dimension for the reference patient.

In some implementations, determining the value of the scaling factor corresponding to the feature dimension based on, for each reference patient, the pre-treatment value and the post-treatment value corresponding to the feature dimension for the reference patient comprises: determining a set of difference values, wherein each difference value represents a difference between the pre-treatment value and the post-treatment value corresponding to the feature dimension for a respective reference patient; determining a measure of central tendency of the set of difference values; and determining the value of the scaling factor corresponding to the feature dimension based on the measure of central tendency of the set of difference values.

In some implementations, scaling factors corresponding to proper subsets of the feature dimensions that are more relevant to the particular medical condition have higher values than scaling factors corresponding to proper subsets of the feature dimensions that are less relevant to the particular medical condition.

In some implementations, for each training example, the multi-modal data from the training example comprises a respective feature representation for each of a plurality of modalities.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

In some implementations, the plurality of modalities include a clinical scale modality, and the feature representation of the clinical scale modality represents data obtained from a clinical interview with the patient.

In some implementations, the plurality of modalities include an electroencephalography (EEG) modality, and the feature representation of the EEG modality is derived from a plurality of voltage waveforms that are each measured by a respective electrode placed in proximity to a brain of the patient.

In some implementations, the plurality of modalities include a genomics modality, and the feature representation of the genomics modality is derived from data defining a sequence of nucleotides from a genome of the patient.

In some implementations, the plurality of modalities include an audio modality, and the feature representation of the audio modality is derived from audio data that represents a sequence of words spoken by the patient.

According to another aspect, there is provided a method performed by one or more computers, the method comprising: receiving multi-modal data characterizing a target subject; generating conditioning data for conditioning the multi-modal data characterizing the target subject based on a population of reference subjects, comprising: receiving, for each reference subject in the population of reference subjects, a feature representation of the reference subject corresponding to a reference modality and having a plurality of feature dimensions; and generating the conditioning data based on the feature representations of the reference subjects; applying the conditioning data to the multi-modal data characterizing the target subject; and after applying the conditioning data to the multi-modal data characterizing the target subject, processing the multi-modal data characterizing the target subject using a machine learning model to generate a machine learning model output for the target subject.

In some implementations, generating the conditioning data based on the feature representations of the reference subjects comprises: determining, for each pair of feature dimensions comprising a first feature dimension and a second feature dimension from the plurality of feature dimensions, a respective correlation coefficient for the pair of feature dimensions that measures a correlation between: (i) a value of the first feature dimension in the feature representations of the reference subjects, and (ii) a value of the second feature dimension in the feature representations of the reference subjects; and generating the conditioning data based on the correlation coefficients.

In some implementations, for each reference subject in the population of reference subjects: the plurality of feature dimensions in the feature representation of the reference subject comprise a respective feature dimension corresponding to each protein in a predefined set of proteins; and the value of each feature dimension corresponding to a protein defines an expression level of the protein in the reference subject.

In some implementations, for each reference subject in the population of reference subjects: the plurality of feature dimensions in the feature representation of the reference subject comprise a respective feature dimension corresponding to each gene in a predefined set of genes; and the value of each feature dimension corresponding to a gene defines an expression level of the gene in the reference subject.

In some implementations, the method further comprises receiving, for each reference subject in the population of reference subjects, a label that defines: (i) whether the reference subject has a particular medical condition, or (ii) whether the reference subject has responded to a treatment for a particular medical condition; wherein generating the conditioning data based on the feature representations of the reference subjects comprises: determining, for each feature dimension from the plurality of feature dimensions, a respective correlation coefficient that measures a correlation between: (i) a value of the feature dimension in the feature representations of the reference subjects, and (ii) the labels of the reference subjects; and generating the condition data based on the correlation coefficients.

In some implementations, for each reference subject in the population of reference subjects, receiving a feature representation of the reference subject corresponding to a reference modality comprises: receiving a pre-treatment feature representation of the reference subject captured before a medical treatment is applied to the reference subject; and receiving a post-treatment feature representation of the reference subject captured after the medical treatment is applied to the reference subject.

In some implementations, generating the conditioning data based on the feature representations of the reference subjects comprises: generating, for each reference subject, a differential feature representation of the reference subject as a difference between: (i) the pre-treatment feature representation of the reference subject, and (ii) the post-treatment feature representation of the reference subject; generating the conditioning data as a combination of the differential feature representations of the reference subjects.

In some implementations, generating the conditioning data as a combination of the differential feature representations of reference subjects comprises: generating the conditioning data as an average of the differential feature representations of the reference subjects.

In some implementations, the pre-treatment feature representation and the post-treatment feature representation of the reference subject are captured using functional magnetic resonance imaging (fMRI).

In some implementations, the pre-treatment feature representation and the post-treatment feature representation of the reference subject are captured using positron emission tomography (PET) imaging.

In some implementations, applying the conditioning data to the multi-modal data characterizing the target subject comprises: pointwise multiplying each of a plurality of feature dimensions of the multi-modal data by a corresponding dimension of the conditioning data.

In some implementations, the conditioning data is represented as a two-dimensional (2D) matrix of numerical values, and wherein applying the conditioning data to the multi-modal data characterizing the target subject comprises: matrix multiplying a plurality of feature dimensions of the multi-modal data by the 2D matrix of numerical values representing the conditioning data.

In some implementations, applying the conditioning data to the multi-modal data characterizing the target subject comprises: applying the conditioning data to a plurality of feature dimensions of the multi-modal data corresponding to a target modality, wherein the target modality is a different modality than the reference modality used to generate the conditioning data.

In some implementations, the machine learning model comprises an encoder neural network, and wherein processing the multi-modal data characterizing the target subject using the machine learning model comprises: processing the multi-modal data characterizing the target subject using the encoder neural network to generate an embedding of the multi-modal data characterizing the target subject; determining a respective classification score for each patient category in a set of patient categories based on the embedding of the multi-modal data characterizing the target subject; and classifying the target subject as being included in a corresponding patient category from the set of patient categories based on the classification scores.

In some implementations, processing the multi-modal data characterizing the target subject using the machine learning model comprises: processing the multi-modal data characterizing the target subject using the machine learning model, in accordance with values of a plurality of machine learning model parameters, to generate a prediction characterizing the target subject.

In some implementations, the prediction characterizing the target subject comprises a prediction for whether the target subject has a particular medical condition.

In some implementations, the multi-modal data characterizing the target subject comprises a respective feature representation for each of a plurality of modalities.

In some implementations, each of the plurality of modalities corresponds to a respective sensor, and wherein the feature representation of each modality is based on data generated by the corresponding sensor.

According to another aspect, there is provided a method comprising: jointly training an encoder neural network having a set of encoder parameters and a decoder neural network having a set of decoder parameters, comprising, at each of a plurality of training iterations: obtaining a batch of training examples, wherein each training example corresponds to a respective subject and includes multi-modal data that characterizes the subject; processing the multi-modal data from each training example using the encoder neural network, in accordance with current values of the encoder parameters, to generate a respective embedding of the multi-modal data from each training example in a latent space; processing the embedding of the multi-modal data from each training example using the decoder neural network, in accordance with current values of the decoder parameters, to generate a respective reconstruction of the multi-modal data from each training example; clustering a set of embeddings into a plurality of clusters of embeddings, wherein each cluster of embeddings includes a plurality of embeddings from the set of embeddings, and wherein the set of embeddings includes the respective embedding of the multi-modal data from each training example; determining a clustering loss based on the clustering of the set of embeddings into the plurality of clusters of embeddings; and updating the current values of the set of encoder parameters and the current values of the set of decoder parameters using gradients of an objective function that depends on: (i) a respective error in the reconstruction of the multi-modal data from each training example, and (ii) the clustering loss.

In some implementations, each embedding in the set of embeddings is associated with a cluster label that identifies a cluster that includes the embedding, and wherein determining the clustering loss based on the clustering of the set of embeddings into the plurality of clusters of embeddings comprises: designating a proper subset of the set of embeddings as being training embeddings; training a classification machine learning model, comprising, for each training embedding, training the classification machine learning model to process the training embedding to predict the cluster label of the training embedding; and after training the classification machine learning model, determining the clustering loss using the classification machine learning model.

In some implementations, determining the clustering loss using the classification machine learning model comprises: designating a proper subset of the set of embeddings as validation embeddings; evaluating a classification accuracy of the classification machine learning model on a task of processing each validation embedding to predict the cluster label of the validation embedding; and determining the clustering loss based on the classification accuracy of the classification machine learning model.

In some implementations, the set of validation embeddings excludes any training embeddings.

In some implementations, updating the current values of the set of encoder parameters using gradients of the objective function that depends on the clustering loss encourages an increase in the classification accuracy of the classification machine learning model.

In some implementations, the classification machine learning model comprises a neural network model.

In some implementations, each embedding in the set of embeddings is associated with: (i) a cluster label that identifies a cluster that includes the embedding, and (ii) a set of confounding features; wherein determining the clustering loss based on the clustering of the set of embeddings into the plurality of clusters of embeddings comprises: designating a proper subset of the set of embeddings as being training embeddings; training a classification machine learning model, comprising, for each training embedding, training the classification machine learning model to process the set of confounding features corresponding to the training embedding to predict the cluster label of the training embedding; and after training the classification machine learning model, determining the clustering loss using the classification machine learning model.

In some implementations, determining the clustering loss using the classification machine learning model comprises: designating a proper subset of the set of embeddings as validation embeddings; evaluating a classification accuracy of the classification machine learning model on a task of processing the set of confounding features corresponding to each validation embedding to predict the cluster label of the validation embedding; and determining the clustering loss based on the classification accuracy of the classification machine learning model.

In some implementations, the set of confounding features are designated as being substantially irrelevant to a medical condition.

In some implementations, the set of confounding features are designated as being substantially irrelevant to a treatment for a medical condition.

In some implementations, for each embedding, the set of confounding features are not included in multi-modal data processed by the encoder neural network to generate the embedding.

In some implementations, for each embedding, the corresponding set of confounding features comprise: features of a sensor that captured sensor data included in the multi-modal data processed by the encoder neural network to generate the embedding, or features of an acquisition protocol used to acquire a portion of the multi-modal data processed by the encoder neural network to generate the embedding, or both.

In some implementations, updating the current values of the set of encoder parameters using gradients of the objective function that depends on the clustering loss encourages a decrease in the classification accuracy of the classification machine learning model.

In some implementations, updating the current values of the set of encoder parameters using gradients of the objective function that depends on the clustering loss encourages confounding features corresponding to embeddings with different cluster labels to become more entangled in a confounding feature space.

In some implementations, clustering the set of embeddings into the plurality of clusters of embeddings comprises applying a k-means clustering operation to the set of embeddings.

In some implementations, the method further comprises: outputting the encoder neural network and the decoder neural network after the joint training of the encoder neural network and the decoder neural network.

In some implementations, for each training example, the multi-modal data included in the training example comprises a respective feature representation for each of a plurality of modalities.

In some implementations, for each training example, the plurality of modalities include a functional magnetic resonance imaging (fMRI) modality, the feature representation for the fMRI modality is derived from a series of fMRI images that each correspond to a respective time point in a sequence of time points and characterize blood flow in a brain of the corresponding subject at the time point.

According to another aspect, there is provided a method performed by one or more computers, the method comprising: receiving multi-modal data characterizing a patient, wherein the multi-modal data comprises a respective feature representation for each of a plurality of modalities; processing the multi-modal data characterizing the patient using a machine learning model, in accordance with values of a set of machine learning model parameters, to generate a patient classification that classifies the patient as being included in a patient category from a set of patient categories; determining an uncertainty measure that characterizes an uncertainty of the patient classification generated by the machine learning model; and generating a clinical recommendation for medical treatment of the patient based on: (i) the patient classification, and (ii) the uncertainty measure that characterizes the uncertainty of the patient classification.

In some implementations, generating the patient classification that classifies the patient as being included in a patient category from the set of patient categories comprises: generating, by the machine learning model, a respective classification score for each patient category in the set of patient categories; and classifying the patient as being included in the patient category based on the classification scores.

In some implementations, classifying the patient as being included in the patient category based on the classification scores comprises: classifying the patient as being included in a patient category having a highest classification score.

In some implementations, determining the uncertainty measure that characterizes the uncertainty of the patient classification generated by the machine learning model comprises: processing the classification scores for the patient categories to identify a trust set for the patient, wherein: the trust set specifies a plurality of patient categories that form a proper subset of the set of patient categories; and the patient is predicted to be included in a patient category within the trust set with at least a threshold probability; and determining the uncertainty measure based on the trust set for the patient.

In some implementations, determining the uncertainty measure based on the trust set for the patient comprises: determining the uncertainty measure based on a number of patient categories included in the trust set for the patient.

In some implementations, processing the classification scores for the patient categories to identify the trust set for the patient comprises: determining an ordering of the patient categories in the set of patient categories based on the classification scores for the patient categories; identifying that, for a particular patient category: (i) a sum of the classification scores for patient categories up to and including the particular patient category, in the ordering of the patient categories, exceeds a predefined threshold, and (ii) a sum of the classification scores for patient categories strictly preceding the particular patient category does not exceed the predefined threshold; and determining that each patient category up to and including the particular patient category, in the ordering of the patient categories, is included in the trust set.

In some implementations, the predefined threshold is determined by operations comprising: obtaining a set of calibration examples, wherein each calibration example corresponds to a respective calibration patient and comprises: (i) multi-modal data characterizing the calibration patient, and (ii) a target patient category of the calibration patient; determining a respective calibration score for each calibration patient; and determining the predefined threshold as a quantile of the calibration scores.

In some implementations, determining the predefined threshold as a quantile of the calibration scores comprises: determining the predefined threshold as an a-th quantile of the calibration scores, wherein a is based on: (i) a number of calibration examples in the set of calibration examples, and (ii) the threshold probability for the trust set.

In some implementations, determining the respective calibration score for each calibration patient comprises, for each calibration patient: processing the multi-modal data characterizing the calibration patient using the machine learning model to generate a respective classification score for each patient category in the set of patient categories; and determining the calibration score for the calibration patient based on an error between: (i) the classification scores for the patient categories, and (ii) the target patient category of the calibration patient.

In some implementations, the machine learning model comprises an encoder neural network, and wherein generating a respective classification score for each patient category in the set of patient categories comprises: processing the multi-modal data characterizing the patient using the encoder neural network to generate an embedding of the multi-modal data characterizing the patient; determining the respective classification score for each patient category in the set of patient categories based on the embedding of the multi-modal data characterizing the patient.

In some implementations, wherein generating a clinical recommendation for medical treatment of the patient comprises: evaluating a confidence criterion based at least in part on the uncertainty measure that characterizes the uncertainty of the patient classification; and in response to determining that the confidence criterion is satisfied, generating the clinical recommendation for the patient based on the patient classification.

In some implementations, evaluating the confidence criterion comprises: determining that the uncertainty measure that characterizes the uncertainty of the patient classification satisfies an uncertainty threshold.

In some implementations, evaluating the confidence criterion further comprises: determining that the patient category includes at least a threshold number of patients.

In some implementations, generating the clinical recommendation for the patient based on the patient classification comprises: determining a fraction of patients included in the patient category that have been designated as having responded to a medical treatment; and determining that the patient should receive the medical treatment based on the fraction of patients included in the patient category that have been designated as having responded to the medical treatment, wherein the clinical recommendation indicates that the patient should receive the medical treatment.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

In some implementations, the plurality of modalities include a genomics modality, and the feature representation of the genomics modality is derived from data defining a sequence of nucleotides from a genome of the patient.

In some implementations, the plurality of modalities include an audio modality, and the feature representation of the audio modality is derived from audio data that represents a sequence of words spoken by the patient.

In some implementations, the plurality of modalities include an electroencephalography (EEG) modality, and the feature representation of the EEG modality is derived from a plurality of voltage waveforms that are each measured by a respective electrode placed in proximity to a brain of the patient.

According to another aspect, there is provided a method performed by one or more computers, the method comprising: obtaining, for each patient in a population of patients, multi-modal data that characterizes the patient; processing, for each patient in the population of patients, the multi-modal data characterizing the patient using an encoder neural network to generate an embedding of the multi-modal data in a latent space, wherein the embeddings of multi-modal data characterizing the patients in the population of patients collectively define a set of embeddings in the latent space; processing the set of embeddings in the latent space to generate a set of parameters defining a region of the latent space that encloses the set of embeddings in the latent space; processing: (i) the set of parameters defining the region of the latent space, and (ii) the set of embeddings, to identify a proper subset of the embeddings in the set of embeddings as being archetype embeddings; and identifying the respective multi-modal data represented by each archetype embedding as a respective multi-modal data archetype.

In some implementations, the region of the latent space that encloses the set of embeddings in the latent space is a convex set.

In some implementations, the region of the latent space that encloses the set of embeddings in the latent space is a convex hull of the set of embeddings in the latent space.

In some implementations, processing: (i) the set of parameters defining the region of the latent space, and (ii) the set of embeddings, to identify a proper subset of the embeddings in the set of embeddings as being archetype embeddings comprises: determining a set of vertices of the region enclosing the set of embeddings in the latent space; and identifying the archetype embeddings using the set of vertices of the region enclosing the set of embeddings in the latent space.

In some implementations, identifying the archetype embeddings using the set of vertices of the region enclosing the set of embeddings in the latent space comprises, for each vertex: identifying an embedding in the set of embeddings that has a minimum distance to the vertex from among the embeddings in the set of embeddings as being an archetype embedding corresponding to the vertex.

In some implementations, the method further comprises, for each multi-modal data archetype: generating a respective intensity score for each of a plurality of feature dimensions of the multi-modal data archetype based on: (i) a value of the feature dimension of the multi-modal data archetype, and (ii) a distribution defined by values of the feature dimension of multi-modal data across the population of patients; generating a representation of the multi-modal data archetype that includes the respective intensity score for each of the plurality of feature dimensions of the multi-modal data archetype.

In some implementations, for each of the plurality of feature dimensions of the multi-modal data archetype, the intensity score for the feature dimension characterizes a likelihood of the value of the feature dimension of the multi-modal data archetype under the distribution defined by values of the feature dimension of multi-modal data across the population of patients.

In some implementations, for each of the plurality of feature dimensions of the multi-modal data archetype, determining the intensity score for the feature dimension comprises: determining a mean and a standard deviation of the distribution defined by values of the feature dimension of multi-modal data across the population of patients; and determining the intensity score for the feature dimension using the mean and the standard deviation of the distribution defined by values of the feature dimension of multi-modal data across the population of patients.

In some implementations, the method further comprises providing the representations of the multi-modal data archetypes as explainability data that explains patterns in multi-modal data across the population of patients.

In some implementations, the method further comprises: clustering the set of embeddings to generate a set of clusters of embeddings, wherein each cluster is represented by a respective archetype embedding; and identifying each cluster of embeddings as representing a respective patient category.

In some implementations, clustering the set of embeddings to generate the set of clusters of embeddings comprises, for one or more embeddings in the set of embeddings: determining, for each archetype embedding, a respective distance between the embedding and the archetype embedding; and assigning the embedding to a cluster represented by an archetype embedding having minimum distance to the embedding.

In some implementations, the encoder neural network has been jointly trained with a decoder neural network on a set of training examples, wherein each training example corresponds to a respective patient and includes multi-modal data that characterizes the patient, wherein: the encoder neural network is configured to process input multi-modal data characterizing an input patient to generate an embedding of the input multi-modal data in the latent space; and the decoder neural network is configured to process the embedding of the input multi-modal data to generate a reconstruction of the input multi-modal data.

In some implementations, jointly training the encoder neural network and the decoder neural network comprises, for each training example: processing the multi-modal data from the training example using the encoder neural network, in accordance with current values of the set of encoder neural network parameters, to generate an embedding of the multi-modal data from the training example; processing the embedding of the multi-modal data from the training example using the decoder neural network, in accordance with current values of the set of decoder neural network parameters, to generate a reconstruction of the multi-modal data from the training example; and updating the current values of the set of encoder neural network parameters and the current values of the set of decoder neural network parameters using gradients of a reconstruction loss function that measures an error in the reconstruction of the multi-modal data from the training example, wherein: the reconstruction loss function comprises a plurality of scaling factors that each scale a respective term in the reconstruction loss function that measures an error in the reconstruction of a corresponding proper subset of a set of feature dimensions of the multi-modal data from the training example, and each of the plurality of scaling factors has a respective value that is based on a relevance of the corresponding proper subset of the set of feature dimensions of the multi-modal data from the training example to a particular medical condition.

In some implementations, the respective value of each of the plurality of scaling factors is based on a relevance of the corresponding proper subset of the set of feature dimensions of the multi-modal data from the training example to diagnosing the particular medical condition.

In some implementations, the respective value of each of the plurality of scaling factors is based on a relevance of the corresponding proper subset of the set of feature dimensions of the multi-modal data from the training example to a treatment for the particular medical condition.

In some implementations, scaling factors corresponding to proper subsets of the set of feature dimensions of the multi-modal data that are more relevant to the particular medical condition have higher values than scaling factors corresponding to proper subsets of the feature dimensions of the multi-modal data that are less relevant to the particular medical condition.

In some implementations, for each patient, the multi-modal data characterizing the patient comprises a respective feature representation for each of a plurality of modalities.

In some implementations, the plurality of modalities include a functional magnetic resonance imaging (fMRI) modality, and the feature representation for the fMRI modality is derived from a series of fMRI images that each correspond to a respective time point in a sequence of time points and characterize blood flow in a brain of the patient at the time point.

According to another aspect, there is provided a method performed by one or more computers, the method comprising: generating a drug signature for a drug, wherein: the drug signature comprises a respective impact score for each of a plurality of features; and the impact score for a feature characterizes an impact, caused by administering a drug to one or more entities, on a value of the feature measured for the one or more entities; generating an embedding of the drug signature in a latent space, comprising: generating a network input to an encoder neural network based on the drug signature; and processing the network input generated based on the drug signature using the encoder neural network to generate the embedding of the drug signature in the latent space; and processing: (i) the embedding of the drug signature in the latent space, and (ii) data defining a plurality of patient categories, to generate a plurality of response scores, wherein each response score corresponds to a respective patient category and characterizes a predicted response of patients included in the patient category to the drug.

In some implementations, generating the drug signature comprises: obtaining, for each of the entities: (i) a pre-treatment feature representation of the entity that comprises, for each of the plurality of features, a respective pre-treatment value of the feature that is measured for the entity prior to the drug being administered to the entity; and (ii) a post-treatment feature representation of the entity that comprises, for each of the plurality of features, a respective post-treatment value of the feature that is measured for the entity after the drug is administered to the entity; and generating the drug signature based on the pre-treatment and post-treatment feature representations of the entities.

In some implementations, generating the drug signature based on the pre-treatment and post-treatment feature representations of the entities comprises: generating, for each of the plurality of entities, a respective differential feature representation of the entity based on a difference between: (i) the pre-treatment feature representation of the entity, and (ii) the post-treatment feature representation of the entity;

and generating the drug signature based on the differential feature representations of the entities.

In some implementations, generating the drug signature based on the differential feature representations of the entities comprises: generating a respective entity-specific drug signature for each of the entities based on the differential feature representation of the entity; and generating the drug signature by combining the entity-specific drug signatures.

In some implementations, for each of the entities, generating the entity-specific drug signature for the entity comprises: element-wise dividing the differential feature representation for the entity by the pre-treatment feature representation of the entity.

In some implementations, generating the drug signature by combining the entity-specific drug signatures comprises: averaging the entity-specific drug signatures.

In some implementations, the drug signature comprises one or more impact scores that each characterize an impact, caused by administering the drug to the one or more entities, on a level of expression of a respective gene in the one or more entities.

In some implementations, the drug signature comprises one or more impact scores that each characterize an impact, caused by administering the drug to the one or more entities, on a level of expression of a respective protein in the one or more entities.

In some implementations, the network input to the encoder neural network includes the drug signature.

In some implementations, each of the plurality of patient categories is defined by a cluster of patient embeddings in the latent space, wherein each patient embedding corresponds to a respective patient and is generated by processing multi-modal data characterizing the patient using the encoder neural network.

In some implementations, for each of the plurality of patient categories, generating the response score for the patient category comprises: determining a respective similarity measure between: (i) the embedding of the drug signature, and (ii) each of one or more patient embeddings in the cluster of patient embeddings defining the patient category; and determining the response score for the patient category based on the similarity measures.

In some implementations, the method further comprises determining a ranking of the plurality of patient categories based on the response scores.

In some implementations, the method further comprises: determining that a new patient is included in a patient category of the plurality of patient categories; identifying the response score for the patient category of the new patient; and automatically generating a recommendation for whether the new patient should receive the drug based at least in part on the response score for the patient category of the new patient.

In some implementations, each of the one or more entities comprises a cell.

In some implementations, each of the one or more entities comprises a collection of cells.

In some implementations, each of the one or more entities is a patient.

In some implementations, the encoder neural network has been trained to process multi-modal data characterizing patients.

In some implementations, the encoder neural network has been trained by operations comprising: obtaining a plurality of training examples, wherein each training example corresponds to a respective patient and includes multi-modal data that characterizes the patient; jointly training the encoder neural network along with a decoder neural network on the plurality of training examples, comprising, for each training example: processing the multi-modal data from the training example using the encoder neural network to generate an embedding of the multi-modal data from the training example; processing the embedding of the multi-modal data from the training example using the decoder neural network to generate a reconstruction of the multi-modal data from the training example; and updating current values of a set of encoder parameters and current values of a set of decoder parameters using gradients of a reconstruction loss function that measures an error in the reconstruction of the multi-modal data from the training example.

Particular embodiments of the subject matter described in this specification can be implemented so as to realize one or more of the following advantages.

The machine learning system described in this specification can process multi-modal data characterizing a patient to generate a multi-modal data embedding that represents the multi-modal data in a lower-dimensional latent space. In particular, the machine learning system can process respective multi-modal data characterizing each patient in a population of patients to generate a set of multi-modal data embeddings distributed across the latent space. The machine learning system can then apply a clustering operation to partition the set of multi-modal data embeddings into a set of clusters. The clustering of the multi-modal data embeddings in the latent space defines a partition of the population of patients into a set of patient categories, i.e., where each patient category corresponds to a respective cluster of multi-modal data embeddings in the latent space.

Each patient category can be understood to represent a "type" of patient, e.g., such that patients included in the same patient category are more likely to share similar characteristics. Conventional approaches for dividing populations of patients into patient categories can rely on criteria that are manually specified by human experts, e.g., traditional medical taxonomic criteria, which are often basic in nature and rely on data from few modalities, in many cases, only one modality. In contrast, the machine learning system provides a data-driven approach for automatically identifying patient categories based on complex patterns and correlations in multi-modal data well beyond what could be analyzed by a human or solely in the human mind.

Patient categories identified by the machine learning system can be used a basis for making inferences (predictions) about patients and for making clinical decisions related to patient care. For example, the patient categories identified by the machine learning system can be used to identify types of patients that are more likely to respond well to certain medical treatments, as will be described in more detail below.

The machine learning system generates embeddings of multi-modal data using a deep neural network, referred to as an encoder neural network. The encoder neural network is configured to process multi-modal data in accordance with values of a set of encoder neural network parameters to implement a non-linear dimensionality reducing transformation that maps the multi-modal data to a corresponding embedding in the latent space. Generating multi-modal data embeddings using a deep neural network (as opposed to, e.g., a linear transformation) can increase the likelihood that the embeddings are readily separable into clusters, and that the clustering is "stable." Clustering can be said to be stable, e.g., if similar clusters are obtained by applying the clustering process to different patient populations.

Generally, multi-modal data characterizing patients is interpretable, e.g., because the value of each feature dimension of the multi-modal data measures a real-world attribute, e.g., blood flow in a region of a brain. In contrast, the latent space (i.e., in which the machine learning system clusters multi-modal data embeddings to identify patient categories), is not directly interpretable. Lack of interpretability can limit the applicability of machine learning systems and their outputs, particularly in settings where acting on the outputs generated by the machine learning system requires user trust and confidence in their validity.

To address this issue, the machine learning system can generate a set of multi-modal data "archetypes," e.g., that can provide a way of interpreting the dimensions of the latent space. More specifically, each multi-modal data archetype can be a collection of multi-modal data that explains a respective dimension of the latent embedding space, i.e., by providing a representation of the dimension of the latent space in the space of multi-modal data. By providing a way of interpreting the dimensions of the latent space, the multi-modal data archetypes can facilitate more efficient use of computational resources. For example, as will be described in more detail below, a user can evaluate the multi-modal data archetypes to determine that one or more dimensions of the latent space represent multi-modal data that is substantially irrelevant, e.g., to a medical condition of interest. In response, the machine learning system can remove the specified dimensions of the latent space, thus reducing the dimensionality of the latent space, and as a result, reducing consumption of computational resources (e.g., memory and computing power) during clustering of the multi-modal data embeddings in the latent space.

In some cases, to generate multi-modal data archetypes, the machine learning system can process multi-modal data characterizing each patient in a population of patients using an encoder neural network to generate a set of embeddings in a latent space. The machine learning system can process the set of embeddings to generate a set of region parameters defining a region of the latent space that encloses the set of embeddings, e.g., the convex hull of the set of embeddings. The machine learning system can then generate multi-modal data archetypes based on the region of the latent space, e.g., by generating a respective multi-modal data archetype corresponding to each vertex of the region. In particular, for each vertex of the region, the machine learning system can identify a respective embedding having minimum distance to the vertex from among the set of embeddings, and identify the multi-modal data represented by the minimum distance embedding as being a multi-modal data archetype.

The machine learning system can thus leverage the geometry of the distribution of the set of embeddings in the latent space to identify a set of multi-modal data archetypes that represent patterns and correlations in multi-modal data across the population of patients. The number of multi-modal data archetypes can be significantly less than the number of patients in the population of patients (e.g., by one or more orders of magnitude), and the multi-modal data archetypes thus provide an efficient and compact representation of multi-modal data characterizing the population of patients. Each multi-modal data archetype can define actual multi-modal data characterizing a real-world patient, as opposed to, e.g., multi-modal data synthesized by the machine learning system, and is thus more reliable as a result of being directly anchored to real-world multi-modal patient data.

The machine learning system jointly trains the encoder neural network (that processes multi-modal data to generate embeddings) along with a decoder neural network (that processes embeddings to generate multi-modal data). The machine learning system then uses the trained neural networks to identify patient categories. The machine learning system trains the encoder and decoder neural networks to optimize an objective function that increases the clinical relevance, e.g., to a particular medical condition, of the patient categories identified using the encoder and decoder neural networks.

For example, the objective function can include a reconstruction loss function. To train the encoder and decoder neural networks using the reconstruction loss function, the machine learning system processes multi-modal data using the encoder neural network to generate an embedding, and then processes the embedding using the decoder neural network to generate a reconstruction (i.e., an estimate) of the original multi-modal data.

The reconstruction loss function penalizes errors in the reconstructed multi-modal data, in particular, by penalizing a respective error in the reconstruction of each feature dimension of the multi-modal data based on the relevance of the feature dimension to a medical condition. More specifically, errors in the reconstruction of feature dimensions that are more relevant to the medical condition incur a higher penalty, under the reconstruction loss function, than errors in the reconstruction of feature dimensions that are less relevant to the medical condition. The reconstruction loss function thereby encourages embeddings to preferentially preserve information content from multi-modal data that is most relevant to the medical condition, and thus increases the relevance of the patient categories (i.e., which are determined by clustering the embeddings) to the medical condition.

As another example, the objective function can include an archetype loss function that is defined with reference to one or more "target" multi-modal data archetypes which can be specified, e.g., by a user of machine learning system. Each target multi-modal data archetype is associated with a corresponding dimension of the latent space and represents a target (i.e., desired) output to be generated by the decoder neural network by processing an embedding representing the dimension of the latent space. For each of one or more dimensions of the latent space that are associated with a respective target multi-modal data archetype, the archetype loss function encourages the decoder neural network to map an embedding representing the dimension of the latent space onto the target multi-modal data archetype.

Generally, a user can select target multi-modal data archetypes using any appropriate criteria, and selecting target multi-modal data archetypes can enable a user to control how the encoder neural network represents multi-modal data in the latent space. This provides a significant advantage over training paradigms that treat the latent space as a "black box" outside the control of the user.

Moreover, users can select target multi-modal data archetypes that represent clinically meaningful patterns in multi-modal data characterizing patients. In particular, users can select target multi-modal data archetypes that are relevant to a medical condition, e.g., that include multi-modal features that typically co-occur in patients having the medical condition. Thus the archetype loss function can encourage embeddings generated by the encoder neural network to represent information relevant to the medical condition, and thereby increase the relevance of the patient categories (i.e., which are determined by clustering the embeddings) to the medical condition.

As another example, the objective function can include a clustering loss function based on a clustering, in the latent space, of embeddings generated by the encoder neural network. The clustering loss function can encourage embeddings generated by the encoder neural network to separate into clusters in the latent space, and can reduce any dependence of the clusters on "confounding" features. Confounding features can refer to features that are designated (e.g., by a user) as being substantially irrelevant, e.g., to a medical condition or to a treatment for a medical condition.

The reconstruction loss function, the archetype loss function, and the clustering loss function can enable reduced consumption of computational resources, e.g., memory and computing power, during training of the encoder and decoder neural networks. For example, the reconstruction, archetype, and clustering loss functions can enable the machine learning system to achieve an acceptable performance in identifying patient categories using encoder and decoder neural networks that have been trained over fewer training iterations, using less training data, or both.

The machine learning system can condition multi-modal data characterizing a "target" subject based on conditioning data, derived from a population of "reference" subjects, to generate conditioned multi-modal data, e.g., that the machine learning system can subsequently process to classify the target subject into a patient category. ("Conditioning" multi-modal data based on conditioning data can refer to updating the multi-modal data by combining the conditioning data with the multi-modal data). Conditioning the multi-modal data has the effect of enriching the information content of the multi-modal data characterizing the target subject based on auxiliary data derived from a population of reference subjects. For example, the reference subjects may be subjects who have received a medical treatment, in particular, a drug, and the machine learning system can condition the multi-modal data characterizing the target subject on average penetration of the drug into respective brain regions across the population of reference patients. As another example, the machine learning system can condition the multi-modal data characterizing the target subject on conditioning data defining statistical correlations, measured across the population of reference subjects, e.g., between gene expression levels or protein expression levels in the reference subjects.

Conditioning multi-modal data on conditioning data derived from a population of reference subjects can enable the encoder neural network to generate richer multi-modal data embeddings that facilitate more effective (e.g., more clinically relevant) patient classification. Moreover, conditioning multi-modal data can enable reduced consumption of computational resources during training of the encoder and decoder neural networks, e.g., by causing the machine learning system to achieve an acceptable performance, e.g., in identifying patient categories and classifying patients, over fewer training iterations, using less training data, or both.

As part of classifying a patient as being included in a patient category, the machine learning system can determine an uncertainty of the patient classification. Uncertainty in patient classification can arise from, e.g., errors and noise in the multi-modal data characterizing the patient, as well as ambiguity inherent in mapping complex, high-dimensional multi-modal data to a discrete set of patient categories. The machine learning system can incorporate the uncertainty of the patient classification into an automated process for generating clinical recommendations (e.g., for patient treatment), e.g., by refraining from generating a clinical recommendation in cases where the patient classification is uncertain. Acting on clinical recommendations, e.g., to administer treatments to patients, requires user trust and confidence in the validity of the clinical recommendations. Measuring uncertainty as part of an automated process for generating clinical recommendations can increase the clinical applicability of the machine learning system.

The machine learning system can generate a "trust set" for a patient that specifies a proper subset of the full set of patient categories, where the patient is predicted to be included in a patient category within the trust set with at least a threshold probability (e.g., 95%). In contrast to a point estimate for a patient classification, i.e., that defines a single "best guess" for the patient category of the patient, the trust set can explain the uncertainty in the patient classification. The trust set can thus increase the interpretability of patient classifications generated by the machine learning system, e.g., by explaining the uncertainty in patient classifications, which can further enhance the clinical applicability of the machine learning system.

The machine learning system can generate a response score for each patient category in the set of patient categories, where the response score for a patient category characterizes a predicted response of patients included in the patient category to receiving a drug. To generate the response scores, the machine learning system can generate a drug signature that characterizes a respective impact of the drug on the value of each of multiple features characterizing an entity that receives the drug, e.g., genomic features, proteomic features, etc. The machine learning system can generate an embedding of the drug signature using an encoder neural network which has been trained to process multi-modal data characterizing patients. The machine learning system can then generate the response scores for the patient categories, e.g., by comparing the drug signature embedding to clusters of multi-modal data embedding representing the patient categories.

The machine learning system can thus generate response scores by leveraging an encoder neural network which has been trained to process one type of data—in particular, multi-modal data characterizing patients—to process a different type of data—in particular, drug signatures—without requiring the use of additional training data or training iterations. Moreover, the machine learning system can generate the response scores in an unsupervised fashion, in particular, without requiring "labeled" training data, e.g., that associates patients or patient categories with real world patient response data. The machine learning system thereby enables more efficient use of computational resources, e.g., as compared to a system that generates response scores by training a specialized machine learning model from scratch on labeled training data.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
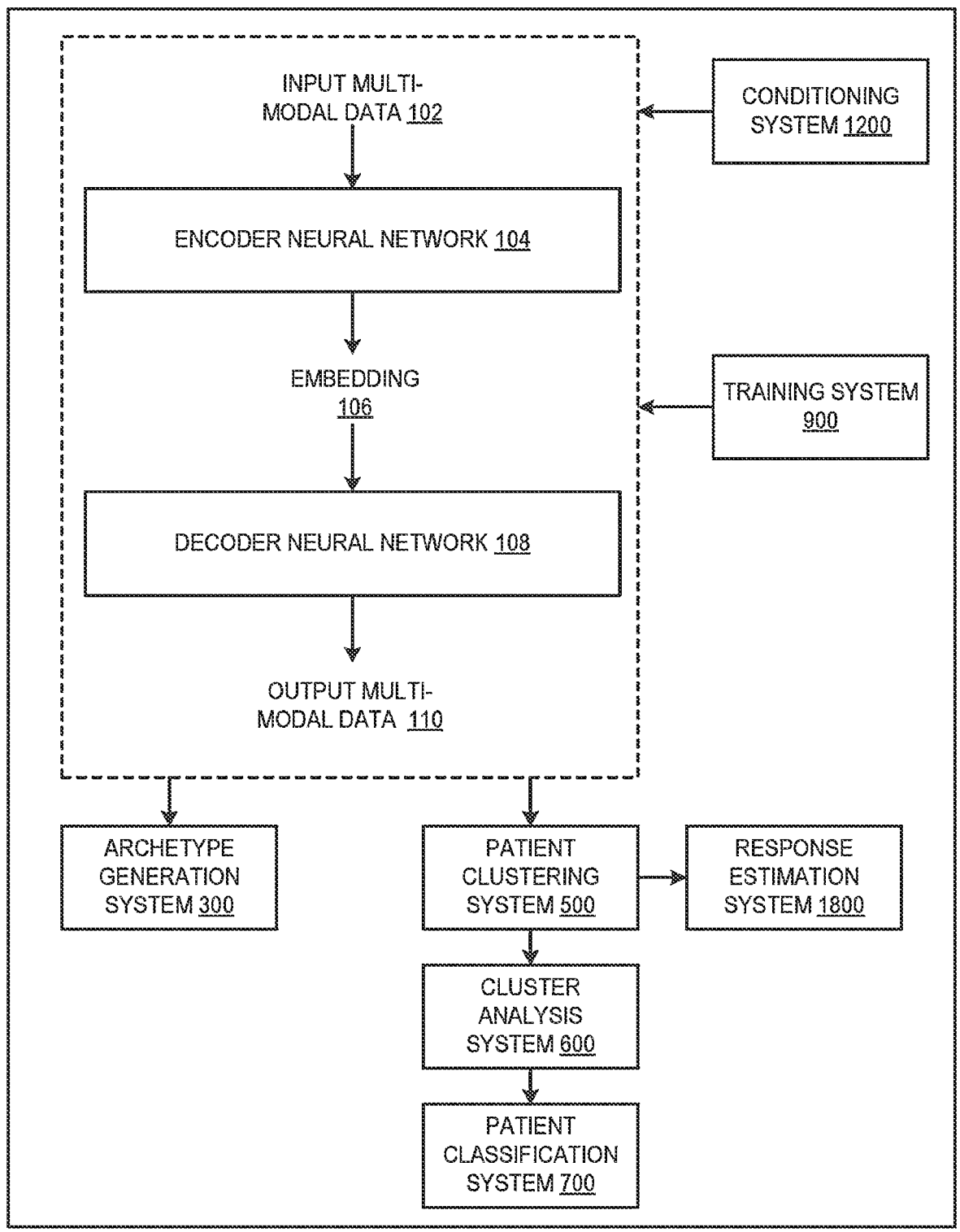
FIG. 1 shows an example machine learning system.

FIG. 1 shows an example machine learning system 100. The machine learning system 100 is an example of a system implemented as computer programs on one or more computers in one or more locations in which the systems, components, and techniques described below are implemented.

The machine learning system 100 processes multi-modal data characterizing patients.

Generally, multi-modal data characterizing a patient includes a respective feature representation for each modality in a set of multiple modalities. A feature representation for a modality refers to a collection of features that collectively represent data from the modality. For convenience, a set of (scalar) features representing multi-modal data can be understood as being indexed by a set of dimensions, referred to as "feature" dimensions.

A few examples of possible modalities, and feature representations for these modalities, are described in more detail next.

In some implementations, multi-modal data characterizing a patient includes data derived from functional magnetic resonance imaging (fMRI) of the brain of the patient. fMRI data can be derived from a sequence of fMRI images, where each fMRI image corresponds to a respective time point in a sequence of time points and characterizes blood flow in the brain at the time point. More specifically, each fMRI image can be represented as array of voxels, where each voxel is associated with an intensity value that represents blood flow at a corresponding location in the brain.

To generate a feature representation of fMRI data of the brain of the patient, the machine learning system 100 can process the fMRI images to generate a respective blood flow curve for each brain region in a set of brain regions that collectively define a parcellation (i.e., partition) of the brain. The blood flow curve for a brain region can define, for each time point in the sequence of time points, the average blood flow in the brain region at the time point. The machine learning system 100 can compute the average blood flow in a brain region at a time point, e.g., by averaging the intensity values of the voxels in the brain region in the fMRI image for the time point. The machine learning system 100 can process the blood flow curves for the brain regions to generate an N×N "functional connectivity" matrix, where N is the number of regions in the parcellation, and where entry (i, j) of the functional connectivity matrix represents a correlation between the blood flow curves for brain region i and brain region j.

A few example techniques for deriving a feature representation of the fMRI data from the functional connectivity matrix are described in more detail next.

In one example, a feature representation of the fMRI data includes the functional connectivity matrix.

In another example, the machine learning system 100 can generate a feature representation of the fMRI data by projecting the functional connectivity matrix onto a vector, where each component of the vector is a combination (e.g., sum or average) of a respective row or column of the functional connectivity matrix.

In another example, to generate a feature representation of the fMRI data, the machine learning system 100 can process the functional connectivity matrix to generate an adjacency matrix that represents a graph. The machine learning system 100 can generate the adjacency matrix, e.g., by setting each value in the functional connectivity matrix exceeds a predefined threshold to 1, and setting each other value in the functional connectivity matrix to 0. The adjacency matrix represents a graph that includes: (i) a set of nodes, where each node corresponds to a respective brain region, and (ii) a set of edges, where each edge connects a respective pair of nodes in the graph. The adjacency matrix defines which nodes in the graph are connected by edges. In particular, an edge connects node i to node j if the value of entry (i, j) in the adjacency matrix of the graph is 1.

After generating the adjacency matrix representing the graph, the machine learning system 100 can generate a set of graph statistics characterizing the topology of the graph represented by the adjacency matrix, and the set of graph statistics can define the feature representation of the fMRI data. The machine learning system 100 can generate any appropriate graph statistics characterizing the topology of the graph represented by the adjacency matrix, e.g., an average measure of centrality (e.g., degree centrality, or PageRank centrality) of the nodes in the graph, an average size of connected components of the graph (where the size of a connected component of the graph can refer to, e.g., the number of nodes in the connected component of the graph), a diameter of the graph, etc.

In another example, to generate the feature representation of the fMRI data, the machine learning system 100 can instantiate a graph that includes: (i) a set of nodes, where each node corresponds to a respective brain region, and (ii) a set of edges, where each edge connects a respective pair of nodes in the graph. The graph can be a fully-connected graph, i.e., such that every pair of nodes in the graph is connected by a respective edge in the graph. The machine learning system 100 can further instantiate a respective node embedding for each node in the graph and a respective edge embedding for each edge in the graph. The node embedding for a node can be an embedding (e.g., a one-hot embedding) that identifies the brain region represented by the node. The edge embedding for an edge connecting a pair of nodes representing brain regions indexed by i and j can be an embedding representing the value of entry (i, j) in the functional connectivity matrix. Thus the machine learning system 100 can instantiate the edge embeddings for the edges in the graph using the functional connectivity matrix.

After instantiating the graph, the machine learning system 100 can process data defining the graph (including the node embeddings and the edge embeddings associated with the graph) using a graph neural network to generate a latent representation of the graph that defines the feature representation of the fMRI data. More specifically, at each of one or more time steps, the graph neural network can update the respective node embedding for each node in the graph by processing the current node embeddings and the current edge embeddings in accordance with values of a set of graph neural network parameters. The machine learning system 100 can then combine (e.g., sum or average) the updated node embeddings associated with the nodes in the graph as of the final time step to generate the feature representation of the fMRI data. The graph neural network can have any appropriate graph neural network architecture that enables it to perform its described function. Examples of graph neural network architectures are described with reference to: J. Zhou et al., "Graph neural networks: a review of methods and applications," *AI Open*, Volume 1, 2020, pages 57-81.

Optionally, in addition to generating a "full" functional connectivity matrix representing functional connectivity between each pair of regions in the set of regions defining the parcellation of the brain, the machine learning system 100 can generate one or more "reduced" functional connectivity matrices. Each reduced functional connectivity matrix represents functional connectivity between each pair of regions in a respective proper subset of the set of regions in the parcellation of the brain. That is, each reduced functional connectivity matrix can be represented by an n×n matrix, where n is the number of regions in the corresponding proper subset of the set of regions in the parcellation of the brain, and entry (i, j) of the reduced functional connectivity matrix represents a correlation between the blood flow curves for brain region i and brain region j.

In some cases, the machine learning system 100 generates one or more reduced functional connectivity matrices that each represent functional connectivity between a respective set of brain regions that are involved in performing a respective biological function in the brain. Examples of biological functions include, e.g., visual data processing, auditory data processing, natural language processing, motor control, etc.

In some cases, the machine learning system 100 generates one or more reduced functional connectivity matrices that each represent functional connectivity between a respective set of brain regions that are anatomically connected in the brain, e.g., that are physically adjacent to one another in the brain.

The machine learning system 100 can generate a respective feature representation of each reduced functional connectivity matrix using any appropriate technique, including any of the techniques described above for generating a feature representation of a full functional connectivity matrix.

In some implementations, multi-modal data characterizing a patient can include clinical scale data obtained from a clinical interview with the patient. Clinical scale data for a patient includes a respective score for the patient in each of multiple categories, where each category is associated with a predefined set of possible scores (e.g., integer values between 1 and 10). Examples of possible categories include, e.g.: apparent sadness, reported sadness, inner tension, reduced sleep, reduced appetite, irritability, aggressiveness, etc. Examples of clinical scales include, e.g.: Positive and Negative Syndrome Scale (PANSS), Brief Assessment of Cognition in Schizophrenia (BACS), Young Mania Rating Scale (YMRS), and Montgomery-Asberg Depression Rating Scale (MADRS). The machine learning system 100 can generate a feature representation of clinical scale data, e.g., e.g., as a sequence of embeddings (e.g., one-hot embeddings), where each embedding represents the score for the patient in a respective category.

In some implementations, multi-modal data characterizing a patient includes electroencephalography (EEG) data. Generally, EEG data includes a respective voltage waveform measured by each of one or more electrodes that are placed at respective locations in proximity to the brain of the patient. The voltage waveform measured by an electrode includes a respective voltage measurement at the location of the electrode at each time point in a sequence of time points.

The machine learning system 100 can generate a feature representation of EEG data in a variety of possible ways. For example, the machine learning system 100 can generate a feature representation of the EEG data by stacking each of the voltage waveforms into a waveform array, e.g., such that each row or column of the waveform array represents a respective voltage waveform. As another example, the machine learning system 100 can transform each voltage waveform into a different domain, e.g., by applying a Fourier transform to each voltage waveform to transform the voltage waveform into a frequency domain, and then stack the transformed voltage waveforms into a transformed waveform array.

In some implementations, multi-modal data characterizing a patient includes genomic data. The machine learning system 100 can represent genomic data in any of a variety of possible formats. A few examples techniques for representing genomic data are described in more detail next.

In one example, the machine learning system 100 can represent genomic data as a sequence of nucleotides from the genome of the patient, where each nucleotide includes a respective nucleobase from a set of possible nucleobases (in particular: guanine, adenine, cytosine, and thymine). The machine learning system 100 can generate a feature representation of the genomic data, e.g., as a sequence of embeddings, where each embedding corresponding to a respective nucleotide in the sequence of nucleotides and identifies the nucleobase included in the nucleotide.

In another implementation, the machine learning system 100 can represent genomic data with reference to a predefined set of genes. In particular, the machine learning system 100 can measure a respective degree to which each gene in the predefined set of genes is expressed in the genome of the patient, and the collection of gene expression values can collectively define the genomic data.

In another example, the machine learning system 100 can represent genomic data with reference to a predefined set of locations of interest in the genome of the patient. In particular, the machine learning system 100 can generate a respective representation (e.g., one-hot embedding) identifying the nucleobase included in the nucleotide at each location of interest in the genome of the patient. The representations of the nucleobases at the locations of interest in the genome of the patient can collectively define the genomic data.

In some implementations, multi-modal data characterizing a patient includes proteomic data, e.g., that characterizes the expression levels of various proteins in the patient. The proteomic data represent, for each protein in a predefined set of proteins, a level of expression of the protein in the patient.

In some implementations, multi-modal data characterizing a patient includes epigenetic data, e.g., that characterizes epigenetic modifications to the genetic material of the patient. Epigenetic modifications are modifications of DNA that can affect gene expression without necessarily altering the DNA sequence. Examples of epigenetic modifications include, e.g., DNA methylation and histone modification. The machine learning system 100 can represent epigenetic data for a patient in any of a variety of possible formats, e.g., by defining a respective rate of occurrence, in the genome of a patient, of each of multiple epigenetic modifications.

In some implementations, multi-modal data characterizing a patient includes transcriptomic data, e.g., that characterizes RNA transcripts that are produced by the genome of a patient. The machine learning system 100 can represent transcriptomic data for a patient in any of a variety of possible formats, e.g., by defining a respective rate of expression, in the patient, of each of multiple RNA transcripts.

In some implementations, multi-modal data characterizing a patient includes demographic data for the patient, e.g., characterizing one or more of: the age, sex, or race of the patient.

In some implementations, multi-modal data characterizing a patient includes characteristics of the family history of the patient, e.g., whether the extended family of the patient includes incidents of disease, e.g., amyotrophic lateral sclerosis (ALS), dementia, Alzheimer's disease, or frontotemporal disorders (FTD).

In some implementations, multi-modal data characterizing a patient includes data characterizing progression of disease in the patient, e.g., the site of onset of a disease, e.g., the bulbar region of the body, the axial region of the body, or the limbs.

In some implementations, multi-modal data characterizing a patient include data characterizing a severity of the disease in the patient, e.g., on a predefined staging scale, e.g., the El Escorial Criteria, or the Revised Amyotrophic Lateral Sclerosis Functional Rating Scale (ALSFRSR).

In some implementations, multi-modal data characterizing a patient can include one more physiological characteristics of the patient, e.g., the grip strength of the patient or the respiratory function of the patient (e.g., the forced vital capacity and slow vital capacity of the patient).

In some implementations, multi-modal data characterizing a patient includes audio data, e.g., that represents a sequence of words spoken by the patient. The feature representation of the audio data can include, e.g., an audio waveform that includes a respective audio sample at each time point in a sequence of time points, or a spectrogram representation.

In some implementations, multi-modal data characterizing a patient includes video data that shows, e.g., the face of the patient or the entire body of the patient as the patient performs a task, e.g., speaking a sequence of words. The video data can be represented, e.g., as a sequence of video frames, or as a sequence of facial activity vectors. Each facial activity vector can correspond to a respective video frame, and can identify whether the face of the patient in the corresponding video frame is exhibiting each facial activity in a set of possible facial activities, e.g., eyes downcast, eyes turned left, eyes turned right, eyebrows raised, etc.

In some cases, multi-modal data characterizing a patient can include multiple feature representations for certain modalities in the set of modalities (i.e., rather than only a single feature representation for each modality). For example, the multi-modal data can include multiple feature representations corresponding to the fMRI modality, including respective feature representations of a full functional connectivity matrix and one or more reduced functional connectivity matrices, as described above.

In many cases, multi-modal data is collected by a device that measures one or more physical attributes of a patient. Such physical attributes are often indicative of the health of the patient.

In some cases, multi-modal data characterizing a patient can be "longitudinal" multi-modal data. That is, multi-modal data characterizing a patient can include respective multi-modal data captured at each time point in a sequence of multiple time points. Longitudinal multi-modal data can extend across any appropriate time span, e.g., with multi-modal data captured each hour in a sequence of hours, or each day in a sequence of day, or each month in a sequence of months, or each year in a sequence of years, etc.

The machine learning system 100 includes one or more of: an encoder neural network 104, a decoder neural network 108, a training system 900, an archetype generation system 300, a patient clustering system 500, a cluster analysis system 600, a patient classification system 700, and a conditioning system 1600 which will each be described in more detail below.

The encoder neural network 104 is configured to process input multi-modal data 102 characterizing a patient to generate an embedding 106 of the input multi-modal data 102 in a multi-dimensional latent space, i.e., a space of possible embeddings.

The decoder neural network 108 is configured to process an embedding 106 from the latent space to generate output multi-modal data 110.

Generally, the encoder neural network 104 and the decoder neural network 108 can have any appropriate neural network architectures that enable them to perform their described functions. Example architectures of the encoder neural network and the decoder neural network 108 are described in more detail with reference to FIG. 2.

The training system 900 can jointly train the encoder neural network 104 and the decoder neural network 108 on a set of training data that includes multiple training examples. Each training example corresponds to a respective patient and includes multi-modal data characterizing the patient.

To jointly train the encoder neural network 104 and the decoder neural network 108 on a training example, the training system 900 processes the multi-modal data from the training example using the encoder neural network 104, in accordance with values of a set of encoder neural network parameters, to generate an embedding of the multi-modal data. The training system 900 then processes the embedding of the multi-modal data using the decoder neural network, in accordance with values of a set of decoder neural network parameters, to generate multi-modal data that defines a reconstruction (i.e., an estimate) of the multi-modal data from the training example.

The training system 900 then updates the respective values of the encoder neural network parameters and the decoder neural network parameters to optimize an objective function that includes a reconstruction error term. The reconstruction error term measures an error between: (i) the multi-modal data from the training example, and (ii) the reconstruction of the multi-modal data from the training example.

The training encourages the encoder neural network 104 to generate embeddings of multi-modal data that preserve the information content of the multi-modal data, i.e., such that the multi-modal data can be reconstructed by the decoder neural network by processing the embeddings. Generally, an embedding of multi-modal data has a lower dimensionality than the multi-modal data itself, and thus an embedding of multi-modal data provides a compressed representation of the multi-modal data. The embeddings generated by the encoder neural network enable more efficient use of computational resources during processing of multi-modal data by the machine learning system 100. In particular, the embeddings occupy less space than the original multi-modal data when stored in a memory, and downstream processing of the embeddings requires fewer arithmetic operations (e.g., additions and multiplications) than would be required to process the original multi-modal data.

An example of a training system 900 for jointly training the encoder neural network 104 and the decoder neural network 108 is described in more detail with reference to FIG. 9. (Optionally, in implementations where the machine learning system 100 uses a graph neural network to generate feature representations of fMRI data, as described above, the training system 900 can jointly train the graph neural network along with the encoder neural network 104 and the decoder neural network 108).

After the encoder neural network 104 and the decoder neural network 108 have been jointly trained by the training system 900, the encoder neural network 104 and the decoder neural network 108 are provided for use by one or more of: the archetype generation system 300, the patient clustering system 500, the cluster analysis system 600, or the patient classification system 700.

The archetype generation system 300 is configured to generate a set of multi-modal data "archetypes." In some implementations, each multi-modal data archetype is a collection of multi-modal data of the same form as the multi-modal data provided as an input to the encoder neural network 104 and generated as an output by the decoder neural network 108. However, rather than directly characterizing individual patients, multi-modal data archetypes are exemplars that typify patterns expressed in multi-modal data characterizing a population of patients. In particular, each multi-modal data archetype can "explain" a respective dimension of the latent embedding space by providing a representation of the dimension of the latent embedding space in the space of multi-modal data. Thus the multi-modal data archetypes provide a way of interpreting the latent embedding space, as will be described in more detail below. Examples of archetype generation systems are described in more detail with reference to FIG. 3.

The patient clustering system 500 is configured to perform a clustering operation on a set of embeddings in the latent space representing respective multi-modal data for each patient in a population of patients to identify "clusters" (i.e., groups) of embeddings in the latent space. Each of these clusters represents a patient category, and the clusters define a partition of the population of patients into the patient categories. An example of a patient clustering system 500 is described in more detail below with reference to FIG. 5.

The cluster analysis system 600 is configured to generate a respective "class distribution" for each patient category identified by the patient clustering system 500. The class distribution for a patient category defines, for each class in a set of classes, a fraction (i.e., proportion) of patients included in the patient category that are associated with the class. The classes can include, e.g., one class indicating that a patient is classified as having responded to a medical treatment, and another class indicating that a patient is classified as having not responded to the medical treatment. An example of a cluster analysis system 600 is described in more detail with reference to FIG. 6.

The patient classification system 700 is configured to process multi-modal data characterizing a patient to classify the patient as being included in a patient category identified by the patient clustering system 500. The classification of a patient into a patient category can be used in conjunction with the class distribution for the patient category, e.g., as a basis for making inferences about the patient and for making clinical decisions related to medical care for the patient, as will be described in more detail below. An example of a patient classification system 700 is described in more detail with reference to FIG. 7A.

The conditioning system 1600 is configured to preprocess multi-modal data provided to the machine learning system 100, e.g., prior to the multi-modal data being processed by the encoder neural network 104. The conditioning system 1600 can process multi-modal data characterizing a "target" subject by conditioning the multi-modal data characterizing the target patient on conditioning data derived from a population of "reference" subjects. ("Conditioning" multi-modal data based on conditioning data can refer to updating the multi-modal data by combining the conditioning data with the multi-modal data). More specifically, the conditioning system 1600 can enrich the multi-modal data characterizing the target subject based on feature representations, corresponding to a reference modality (e.g., a PET or fMRI modality) of the reference subjects. An example of a conditioning system 1600 is described in more detail with reference to FIG. 16.

The response estimation system 1800 is configured to generate a respective response score for each patient category determined by the patient clustering system 500, where the response score for a patient category characterizes a predicted response of patients included in the patient category to receiving a drug. An example of a response estimation system 1800 is described in more detail with reference to FIG. 18.

Figure 2:
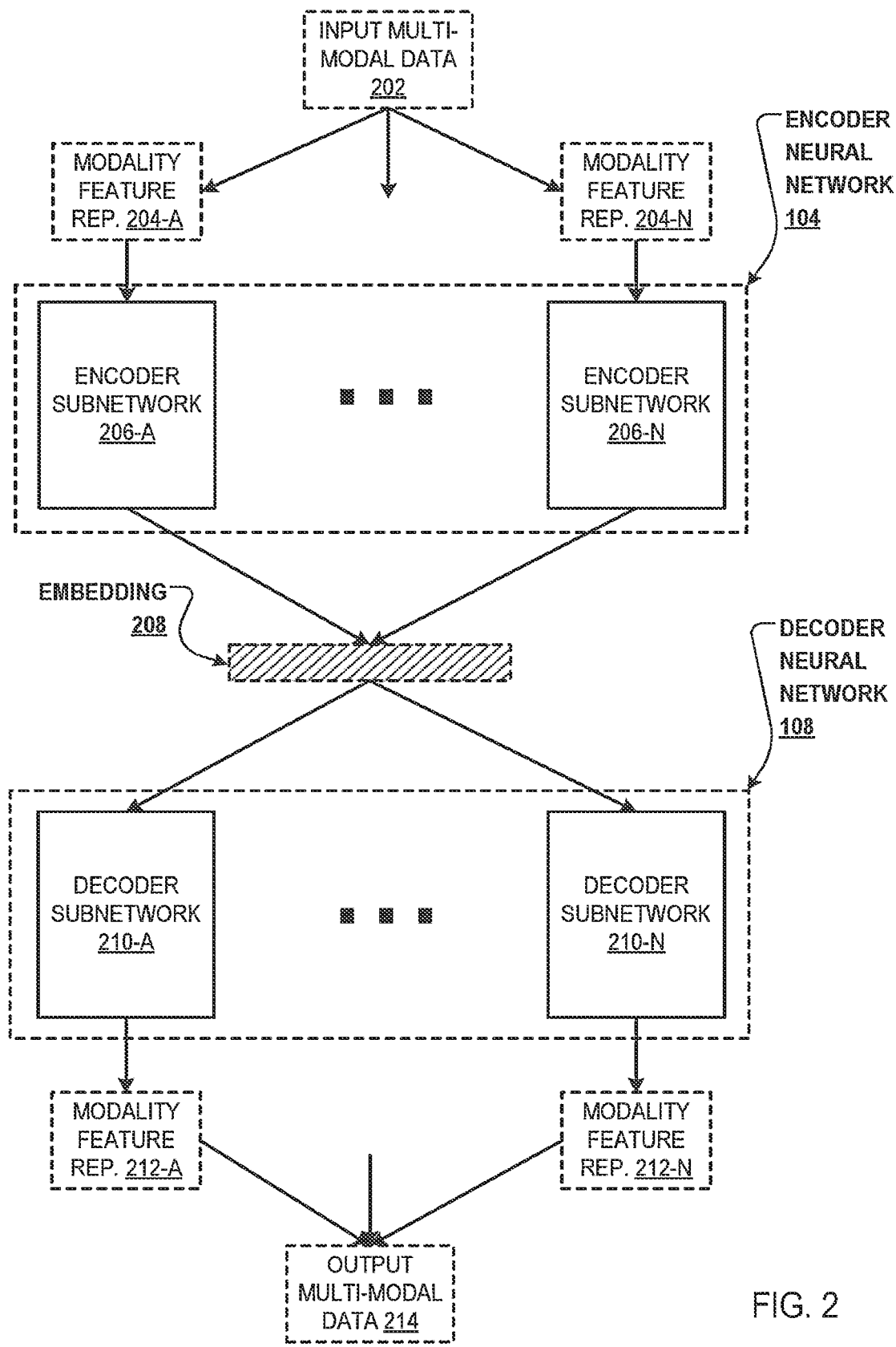
FIG. 2 shows an example architecture of an encoder neural network and a decoder neural network.

FIG. 2 shows an example architecture of an encoder neural network 104 and a decoder neural network 108.

The encoder neural network 104 receives input multi-modal data 202 that includes multiple modality feature representations 204-A-204-N. Each modality feature representation 204-A-204-N includes a collection of features that collectively represent data from a corresponding modality. Examples of modality feature representations are described with reference to FIG. 1.

The encoder neural network 104 includes multiple encoder subnetworks 206-A-206-N, where each encoder subnetwork corresponds to a respective modality and is configured to receive as input a feature representation of the corresponding modality. For example, encoder subnetwork 206-A is configured to receive modality feature representation 204-A, and encoder subnetwork 206-N is configured to receive modality feature representation 204-N.

Each encoder subnetwork processes a corresponding modality feature representation to generate a set of parameters that define a probability distribution over the latent space. For example, each encoder subnetwork $E_i$ can generate a mean vector $\mu_i$ and a covariance matrix $V_i$ of a Normal distribution over the latent space.

The encoder neural network 104 combines the probability distribution parameters generated by each encoder subnetwork to generate parameters of a "posterior" probability distribution over the latent space. For example, if each encoder subnetwork generates mean and covariance parameters of a Normal distribution, as described above, then the encoder neural network can generate the a mean vector $\mu$ and a covariance matrix V of the posterior probability distribution as:

$$\mu = \left(\sum_{i=0...n} \mu_i V_i^{-1}\right)\left(\sum_i V_i^{-1}\right)^{-1} \quad (1)$$

$$V = \left(\sum_{i=0...n} V_i\right)^{-1} \quad (2)$$

where $\mu_0$ is a mean vector of a predefined "prior" Normal probability distribution, $V_0$ is a covariance matrix of the predefined prior Normal distribution, and for each $i \in \{1, \ldots, n\}$, $\mu_i$ is the mean vector generated by encoder subnetwork $i$ and $V_i$ is the covariance matrix generated by encoder subnetwork $i$.

The encoder neural network 104 generates the embedding 208 of the input multi-modal data 202 using the posterior probability distribution over the latent space. For example, the encoder neural network 104 can select the embedding of the input multi-modal data as the mean of the posterior probability distribution over the latent space. (During training, the embedding 208 can be sampled from the latent space in accordance with the posterior probability distribution, as will be described in more detail below).

The decoder neural network 108 includes multiple decoder subnetworks 210-A-210-N. Each decoder subnetwork is configured to process an embedding 208 from the latent space (e.g., an embedding generated by the encoder neural network) to generate a corresponding modality feature representation. For example, decoder subnetwork 210-A is configured to generate modality feature representation 212-A, and decoder subnetwork 210-N is configured to generate modality feature representation 212-N. The collection of modality feature representations generated by the decoder subnetworks collectively define the output multi-modal data 214.

Generally, each of the encoder subnetworks and each of the decoder subnetworks can have any appropriate neural network architecture which enables them to perform their described functions. In particular, each encoder subnetwork and each decoder subnetwork can have any appropriate types of neural network layers (e.g., fully-connected layers, convolutional layers, attention layers, etc.) in any appropriate numbers (e.g., 5 layers, 25 layers, or 50 layers) and connected in any appropriate configuration (e.g., as a linear sequence of layers).

In some cases, the input multi-modal data 202 can be incomplete, i.e., certain modality feature representations can be missing from the input multi-modal data 202. This can occur, e.g., if data from certain modalities were not collected for a patient, or are otherwise unavailable for a patient. In this situation, the encoder neural network 104 can generate an embedding 208 of the input multi-modal data 202 by processing the available modality feature representations using the corresponding encoder subnetworks, and combining the outputs of the encoder subnetworks in accordance with equations (1)-(2). Encoder subnetworks that are configured to process the missing modality feature representations are not used to generate the embedding 208 of the input multi-modal data 202.

The decoder neural network 108 can generate a complete set of multi-modal output data 214, i.e., that includes each modality feature representation, by processing any embedding 208 from the latent space, including embeddings 208 generated by the encoder neural network using incomplete multi-modal input data 202.

Figure 3A:
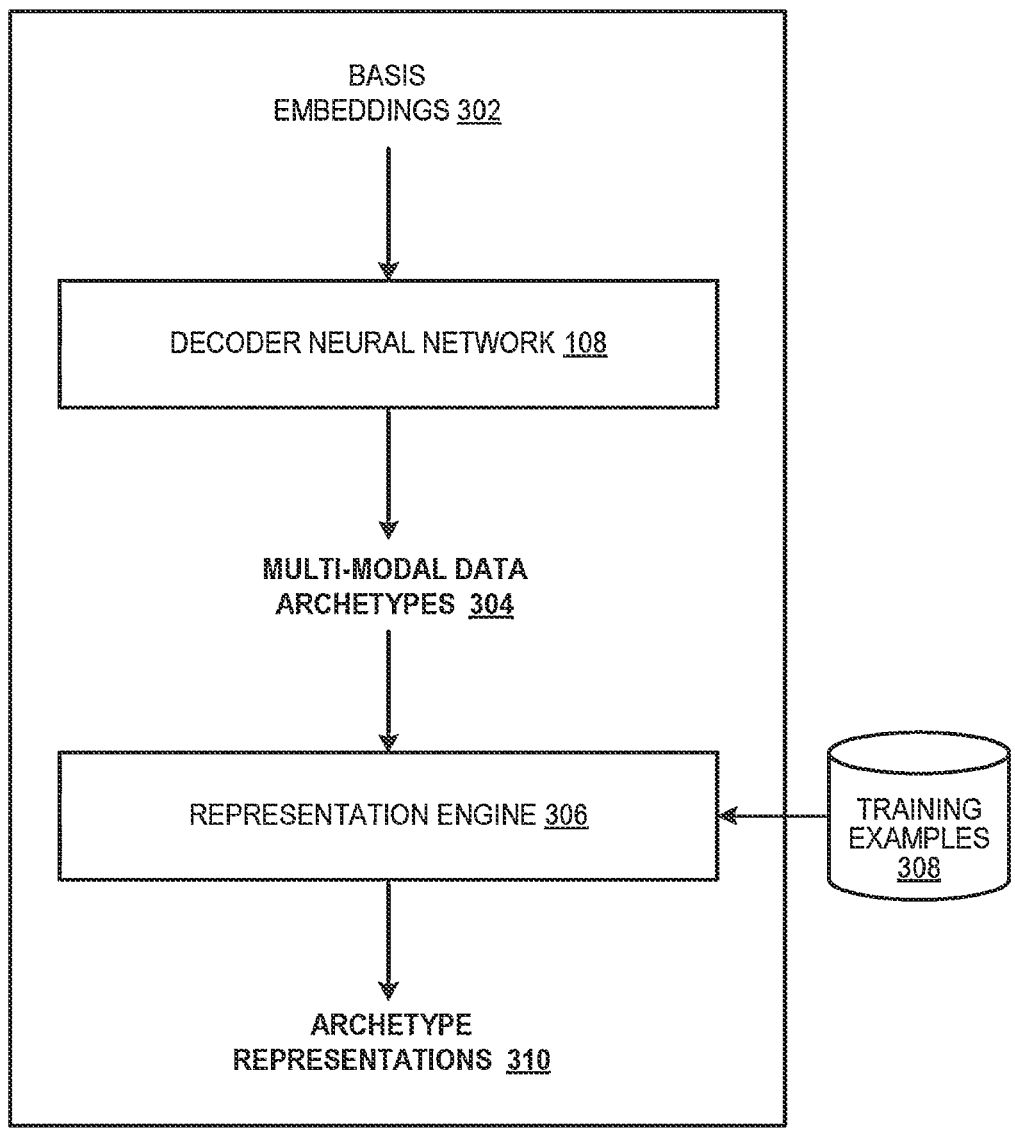
FIG. 3A-3B show example archetype generation systems.
Figure 3B:
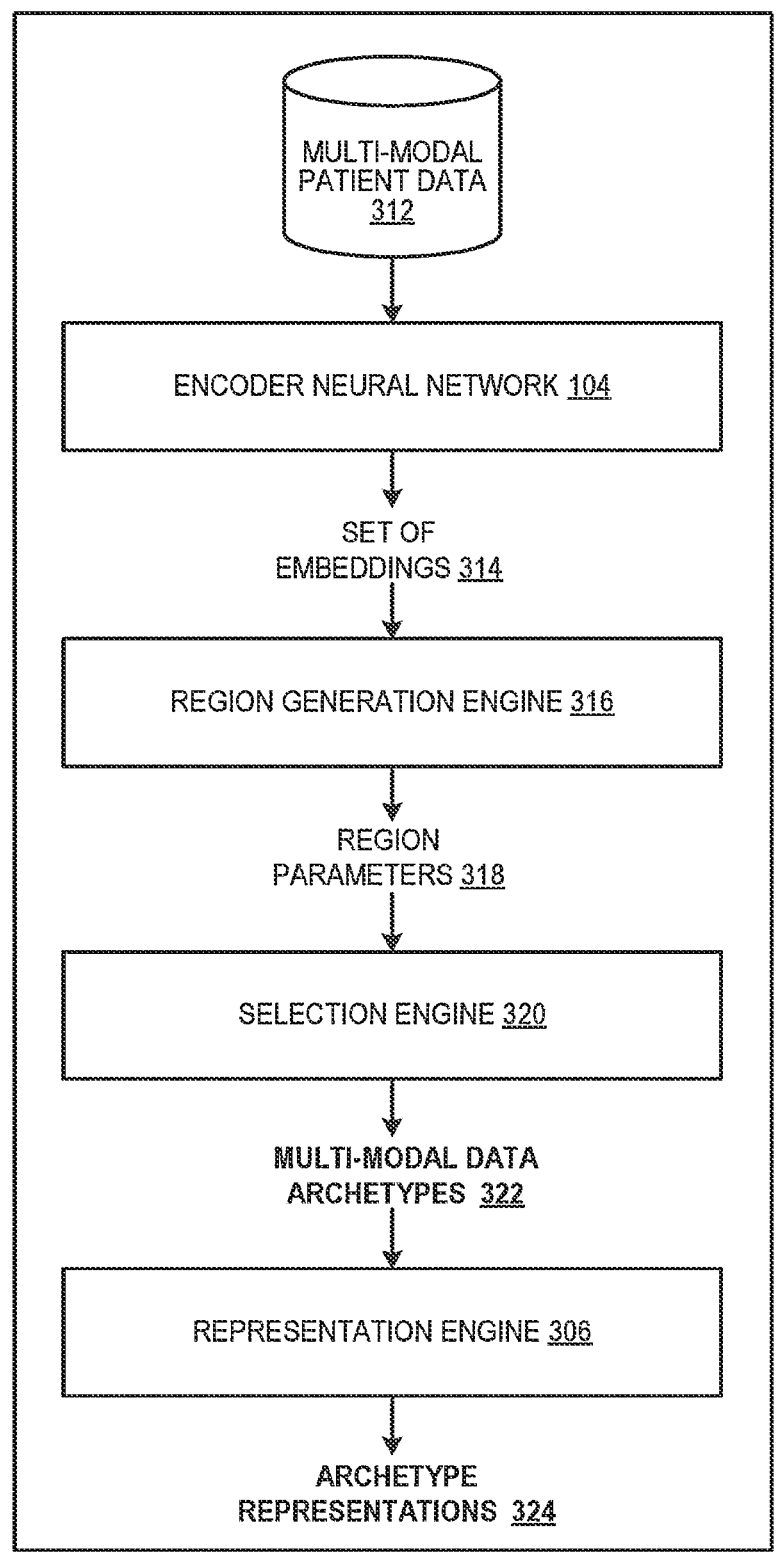

FIG. 3A and FIG. 3B show respective example implementations of an archetype generation system. The archetype generation systems shown in FIG. 3A and FIG. 3B are examples of systems implemented as computer programs on one or more computers in one or more locations in which the systems, components, and techniques described below are implemented. The archetype generation systems described with reference to FIG. 3A and FIG. 3B can be used in combination, or as alternatives, or otherwise implemented and used in any other appropriate fashion for generating multi-modal data archetypes and archetype representations, as will be described in more detail below.

FIG. 3A shows an example archetype generation system 300A. The archetype generation system 300A is configured to generate a set of multi-modal data archetypes 304, and for each archetype, a corresponding archetype representation 310. Each multi-modal data archetype 304 corresponds to a respective dimension of the latent space and provides a representation of the dimension of the latent space in the space of multi-modal data. An archetype representation of a multi-modal data archetype provides an interpretable representation of the multi-modal data archetype, as will be described in more detail below.

The archetype generation system 300A generates the multi-modal data archetypes 304 and the archetype representations 310 using a decoder neural network 108 (as described with reference to FIG. 1 and FIG. 2) and a representation engine 306. Prior to being used by the archetype generation system 300A, the decoder neural network 108 is jointly trained, along with an encoder neural network 104, e.g., by the training system 900 described with reference to FIG. 9. The representation engine 306 will be described in more detail below.

The archetype generation system 300A generates the multi-modal data archetypes using a set of "basis" embeddings in the latent space of multi-modal data embeddings that provide a basis of the latent space. A set of embeddings in the latent space is said to provide a basis of the latent space if each possible embedding in the latent space can be uniquely represented as a linear combination of set of embeddings. That is, a set of embeddings is said to provide a basis if, for each possible embedding, there exists a unique (i.e., exactly one) set of scalar coefficients such that combining the set of embeddings by a linear combination using the set of scalar coefficients yields the possible embedding. Each basis embedding in a set of basis embeddings can be understood to represent a respective dimension of the latent space.

The archetype generation system 300A can generate the multi-modal data archetypes using any appropriate set of basis embeddings in the latent space. For example, the set of basis embeddings can be given by the set of "unit" embeddings in the latent space. A unit embedding in the latent space refers to an embedding in the latent space where one position in the embedding has value 1, and the other positions in the embedding have value 0. As another example, the set of basis embeddings can be given by a set of embeddings obtained by scaling the set of unit embeddings by a non-zero value. As another example, the set of basis embeddings can be given by a set of embeddings obtained by rotating the set of unit embeddings in the latent space by any non-zero angle along any axis in the latent space.

The set of basis embeddings 302 can be a predefined set of basis embeddings, or a set of basis embeddings that are provided to the archetype generation system 300A, e.g., by a user of the archetype generation system.

The archetype generation system 300A processes each basis embedding 302 using the decoder neural network 108 to generate multi-modal data that defines a corresponding multi-modal data archetype 304. The multi-modal data archetypes are exemplars that typify patterns expressed in multi-modal data characterizing a population of patients, e.g., the population of patients that provided the multi-modal data used for training the decoder neural network 108. In particular, each multi-modal data archetype provides a representation of a corresponding dimension of the latent space in the space of multi-modal data.

Multi-modal data characterizing any patient can be represented as an embedding in the latent space, i.e., by processing the multi-modal data characterizing the patient using an encoder neural network. The embedding of the multi-modal data characterizing the patient can be uniquely expressed as a combination of the basis embeddings in the latent space. Thus the basis embeddings in the latent space provide a set of "latent archetypes" that can be used to represent an embedding of multi-modal data characterizing any patient. The multi-modal data archetypes provide a representation of the latent archetypes in the space of multi-modal data.

An illustration of the concept of archetypes is provided in FIG. 4. The shape of a human face is generally a combination of one or more underlying shapes, e.g., oblong, oval, round, rectangular, etc. For example, the shape of one face might be a combination of oblong and oval shapes, while the shape of another face might be a combination of diamond and inverted triangle shapes.

Figure 4A:
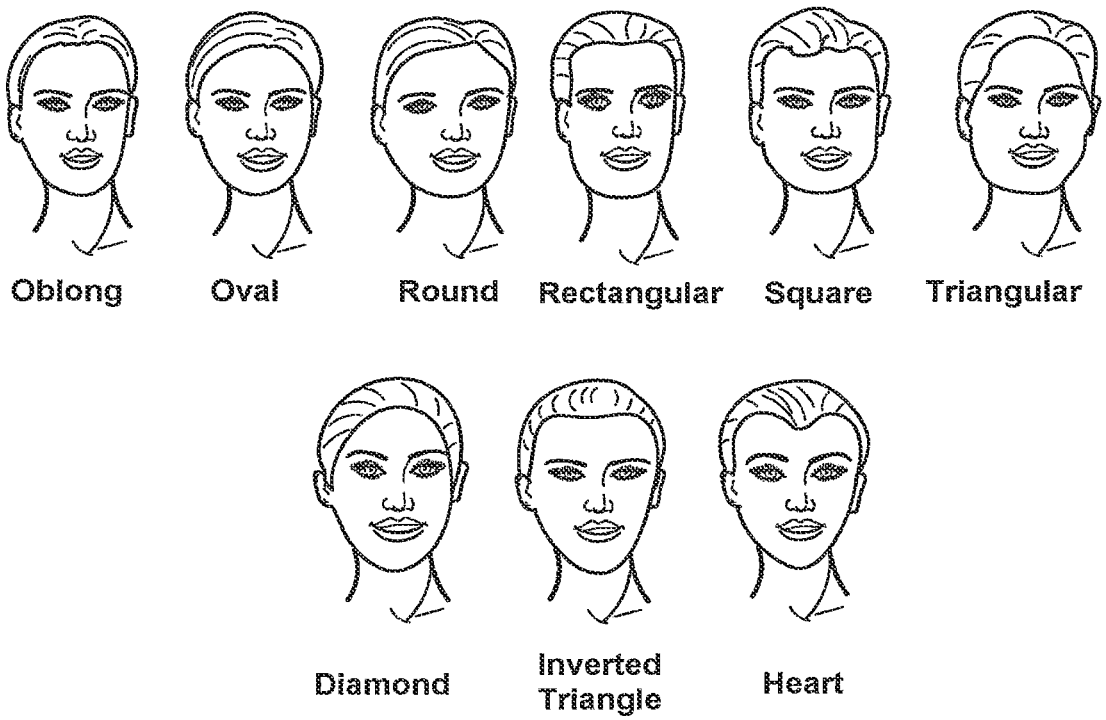
FIG. 4A-C illustrate archetypes and example processes for generating archetypes.

Each of the underlying shapes can be understood as being a face shape archetype, i.e., an exemplar that typifies patterns expressed in the shapes of human faces. Similarly, each of the multi-modal data archetypes typify patterns expressed in multi-modal data characterizing patients. It can be appreciated that the face shape archetypes illustrated in FIG. 4A provide a way of interpreting the distribution of human face shapes. The multi-modal data archetypes 304 similarly provide a way of interpreting the distribution of multi-modal data characterizing patients, and in particular, of interpreting the multi-modal data represented by each dimension of the latent space.

However, in contrast to the face shape archetypes illustrated in FIG. 4A, which accommodate immediate interpretation by visual inspection, the multi-modal data archetypes 304 are generally high-dimensional collections of modality feature representations that can be significantly more challenging to interpret. Thus while the multi-modal data archetypes provide a way of interpreting the dimensions of the latent space, there is a need for a way of interpreting the multi-modal data archetypes themselves.

To this end, the archetype generation system 300A uses the representation engine 306 to generate a respective archetype representation 310 for each multi-modal data archetype 304, as will be described in more detail next.

Generally, multi-modal data (including multi-modal data archetypes and multi-modal data characterizing patients) can be understood as being represented by a set of feature representations that each include a respective collection of features. For convenience, the features representing multi-modal data can be understood as being organized into a set of feature dimensions, where each feature dimension is associated with a value of a corresponding feature representing the multi-modal data, as described above.

The archetype representation 310 for a multi-modal data archetype 304 includes a respective "intensity score," represented as a numerical value, corresponding to each feature dimension of the multi-modal data archetype 304. To determine the intensity score for a feature dimension of a multi-modal data archetype, the representation engine 306 identifies a respective value of the feature dimension in multi-modal data included in each training example in a set of training examples 308. The values of the feature dimension in the multi-modal data of the training examples collectively define a distribution of values of the feature dimension. The representation engine 306 then determines the intensity score for the feature dimension based on: (i) the value of the feature dimension of the multi-modal data archetype, and (ii) the distribution defined by values of the feature dimension in the multi-modal data of the training examples.

Generally, the intensity score for a feature dimension of a multi-modal data archetype can characterize a likelihood of the value of the feature dimension of the multi-modal data archetype under the distribution defined by values of the feature dimension in the multi-modal data of the training examples. For example, the representation engine 306 can determine the intensity score for a feature dimension of a multi-modal data archetype as:

$$z = \frac{x - \mu}{\sigma} \quad (3)$$

where z is the intensity score for the feature dimension, x is the value of the feature dimension in the multi-modal data archetype, μ is the average of the distribution defined by values of the feature dimension in the multi-modal data of the training examples, and a is the standard deviation of the distribution defined by values of the feature dimension in the multi-modal data of the training examples. (In this example, a higher value of the intensity score represents a lower likelihood of the value of the feature dimension of the multi-modal data under the distribution defined by values of the feature dimension in the multi-modal data of the training examples).

The set of training examples 308 can be the same set of training examples that are used to train the decoder neural network jointly with the encoder neural network, e.g., by the training system described with reference to FIG. 9. Alternatively, some or all of the training examples 308 can be "held out" training examples that include multi-modal data that was not used during training of the decoder neural network and the encoder neural network.

The archetype representation 310 for a multi-modal data archetype 304 facilitates interpretation of the multi-modal data archetype by indicating which features in the multi-modal data archetype have values that differ most significantly from the "expected" feature values across the multi-modal data of the training examples. Particularly if the number of feature dimensions is very large (e.g., in the thousands), the archetype representation for a multi-modal data archetype can enable a user to rapidly identify the feature dimensions that best explain the multi-modal data archetype, e.g., the feature dimensions having the highest intensity scores.

Figure 4B:
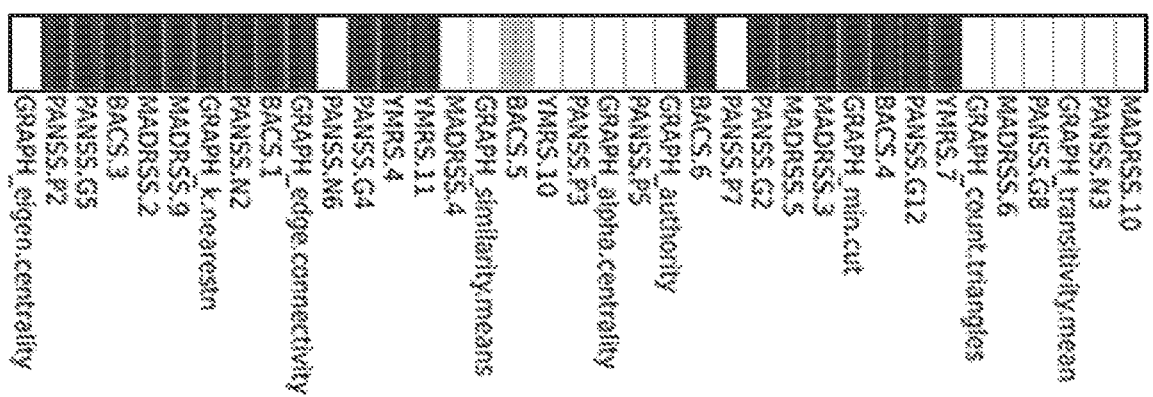

The archetype generation system 300A can make the multi-modal data archetypes 304 and the archetype representations 310 available to a user of the archetype generation system 300A in any of a variety of possible ways. For example, the archetype generation system 300A can illustrate the archetype representations 310 to a user in a visual format, e.g., as shown in FIG. 4B, where the intensity score for each of multiple feature dimensions of a multi-modal data archetype is represented by a shade of color. In this example, higher intensity scores are represented by darker shades, and lower intensity scores are represented by lighter shades.

In addition to providing a way of interpreting the dimensions of the latent space, the multi-modal data archetypes can further provide a mechanism for interpreting multi-modal data characterizing individual patients.

For example, to facilitate interpretation of input multi-modal data characterizing a patient, the archetype generation system 300A can process the input multi-modal data using the encoder neural network to generate an embedding of the input multi-modal data. The archetype generation system 300A can then determine a respective coefficient (i.e., numerical value) for each basis embedding in a set of basis embeddings in the latent space such that linearly combining the basis embeddings in accordance with the coefficients yields the embedding of the input multi-modal data. The archetype generation system 300A can then provide an output that identifies: (i) each multi-modal data archetype, and (ii) for each multi-modal data archetype, the value of the coefficient of the corresponding basis embedding in the latent space. The values of the coefficients can enable a user to interpret the contribution of each multi-modal data archetype to the input multi-modal data.

The archetype generation system 300A can make the multi-modal data archetypes 304 and the archetype representations 310 available to users, e.g., through a user interface, e.g., a graphical user interface (GUI).

FIG. 3B shows an example archetype generation system 300B. The archetype generation system 300B can be used as an alternative to, or in combination with, the archetype generation system 300A described above with reference to FIG. 3A.

The archetype generation system 300B is configured to generate a set of multi-modal data archetypes 322, and for each multi-modal data archetype 322, a corresponding archetype representation 324. The multi-modal data archetypes 322 are exemplars that typify patterns expressed in multi-modal data characterizing a population of patients. The number of multi-modal data archetypes 322 can be significantly less than the number of patients in the population, e.g., by one or more orders of magnitude. The multi-modal data archetypes thus provide an efficient way of representing patterns expressed in multi-modal data characterizing the population of patients. An illustration of the concept of archetypes is provided in FIG. 4, and is described in more detail above. An archetype representation of a multi-modal data archetype provides an interpretable representation of the multi-modal data archetype, as described in more detail above with reference to FIG. 3A.

The archetype generation system 300B generates the set of multi-modal data archetypes 322 using an encoder neural network 104, a region generation engine 316, and a selection engine 320, which are each described in more detail next.

The encoder neural network 104 is configured to process multi-modal data characterizing a patient to generate an embedding of the multi-modal data in a latent space. An example architecture of the encoder neural network is described above with reference to FIG. 2. Prior to being used by the archetype generation system 300B, the encoder neural network 104 is jointly trained, along with a decoder neural network 108, e.g., by the training system 900 described with reference to FIG. 9.

For each patient in a population of patients, the archetype generation system 300B processes multi-modal data 312 characterizing the patient using the encoder neural network 104 to generate a corresponding embedding in the latent space. The embeddings of the multi-modal data characterizing the patients in the population of patients collectively form a set of embeddings 314. The set of embeddings 314 includes a respective embedding for each patient in the population of patients.

The population of patients can include any appropriate number of patients, e.g., 1000 patients, 10,000 patients, or 100,000 patients. Patients can be selected for inclusion in the population of patients based on any appropriate selection criteria, e.g., selection criteria based on patient demographics, e.g., age, gender, etc. In some instances, the population of patients may be candidates for inclusion in a clinical trial for a therapy, e.g., a drug.

The region generation engine 316 processes the set of embeddings 314 to generate a set of region parameters 318 that define a region of the latent space. The region parameters 318 can define a region of the latent space that encloses the set of embeddings 314, e.g., such that each embedding in the set of embeddings 314 is included in the region defined by the region parameters 318. The region parameters can be represented as an ordered collection of numerical values, e.g., a vector, matrix, or other tensor of numerical values.

The region generation engine 316 can be configured to generate region parameters 318 that define a region of the latent space in any appropriate way. A few example techniques by which the region generation engine 316 can generate region parameters 318 defining a region of the latent space are described next.

In one example, the region generation engine 316 can generate region parameters 318 that define an (approximation of a) convex hull of the set of embeddings in the latent space. The "convex hull" of a set of embeddings can refer to a convex set, e.g., the minimal convex set, that contains each embedding in the set of embeddings. A set can be referred to as "convex" if, for any elements $v_1, \ldots, v_K$ included in the set, and for any non-negative scalar coefficients $\alpha_1, \ldots, \alpha_K$ that sum to 1, an element defined by:

$$v = \sum_{k=1}^{K} \alpha_k \cdot v_k$$

is also included in the set. Intuitively, any two elements in a convex set can be joined by a line that lies entirely within the convex set. A convex set that contains a set of embeddings can be referred to as the "minimal" convex set containing the set of embeddings if any convex set containing the set of embeddings necessarily includes the minimal convex set. The convex hull of the set of embeddings 314 can be a convex polytope, i.e., a convex region with flat sides. An example of a convex hull of a set of embeddings in three-dimensional (3D) space is illustrated with reference to FIG. 4C and described in more detail below.

The region generation engine 316 can generate region parameters 318 that define the convex hull of the set of embeddings in the latent space using any appropriate numerical technique, e.g., the "quickhull" technique described with reference to: C. Barber et al., "The quickhull algorithm for convex hulls," *ACM Transactions on Mathematical Software*, Volume 22, Issue 4, December 1996, pp. 469-483.

Region parameters 318 defining the convex hull of the set of embeddings 314 can be represented in any appropriate way. For instance, the region parameters 318 can define a set of vertex embeddings, where each vertex embedding represents a position of a respective vertex (e.g., corner) of the convex hull of the set of embeddings 314. As another example, the set of region parameters 318 can define a set of planar surfaces, where each planar surface represents a respective face of a convex polytope defining the convex hull of the set of embeddings 314. The region parameters 318 can define a planar surface, e.g., by defining an embedding orthogonal to the planar surface and a embedding positioned on the planar surface.

In another example, the region generation engine 316 can generate region parameters 318 that define an (approximation of a) concave hull of the set of embeddings in the latent space. The region generation engine 316 can generate region parameters 318 that define the concave hull of the set of embeddings in the latent space using any appropriate numerical technique, e.g., the techniques described with reference to: A. Moreira et al., "Concave hull: a k-nearest neighbors approach for the computation of the region occupied by a set of points," *International Conference on Computer Graphics Theory and Applications*, 2007, pp. 61-68.

In another example, the region generation engine 316 can generate region parameters 318 that define an (approximation of an) alpha shape for the set of embeddings in the latent space. The region generation engine 316 can generate region parameters 318 that define an alpha shape of the set of embeddings in the latent space using any appropriate numerical technique, e.g., the techniques described with reference to: H. Edelsbrunner, "Alpha shapes—a survey," in: van de Weygaert R, Vegter G, Ritzerveld J, Icke V, eds. *Tessellations in the Sciences: Virtues, Techniques and Applications of Geometric Tilings*. Springer, 2011.

The selection engine 320 is configured to generate the set of multi-modal data archetypes 322 based on: (i) the set of embeddings 314, and (ii) the region parameters 318. In particular, the selection engine 320 can select a proper subset of the set of embeddings 314 as being "archetype" embeddings based on their proximity to vertices of the region defined by the region parameters 318. For each archetype embedding, the selection engine 320 can identify the multi-modal data represented by the archetype embedding as being a multi-modal data archetype 322.

More specifically, to identify the archetype embeddings, the selection engine 320 can determine a set of vertices of the region of the latent space defined by the region parameters 318. (Each vertex can be represented as a point in the latent space, where each point in the latent space can be represented as an ordered collection of numerical values, e.g., a vector or other tensor of numerical values). For instance, the region parameters 318 can directly define the vertices of the region (as described above), and the selection engine 320 can thus directly identify the vertices of the region from the values of the region parameters 318. As another example, the region parameters 318 can define a set of planar surfaces representing faces of a convex polytope region, and the selection engine 320 can identify points on the surface of the convex polytope where multiple faces converge to a point as vertices of the region.

After identifying the vertices of the region of the latent space defined by the region parameters 318, the selection engine 320 can identify a respective multi-modal data archetype corresponding to each of the vertices of the region. In particular, for each vertex, the selection engine 320 can designate an embedding from the set of embeddings 314 that has a minimum distance to the vertex from among the embeddings in the set of embeddings 314 as being an archetype embedding. The selection engine 320 can then identify the multi-modal data represented by the archetype embedding as being a multi-modal data archetype 322. The multi-modal data represented by an archetype embedding can refer to the multi-modal data processed by the encoder neural network 104 to generate the archetype embedding.

The selection engine 320 can measure distances between embeddings and vertices in the latent space using any appropriate distance measure, e.g., a Euclidean distance or an $L_1$ distance.

In some cases, an embedding from the set of embeddings 314 may exactly match a vertex of the region, and the selection engine 320 can identify the embedding matching the vertex as being an archetype embedding. In some cases, none of the embeddings from the set of the embeddings 314 match a given vertex, and to identify the archetype embedding corresponding to the vertex, the selection engine 320 can compute a respective distance from the vertex to each embedding in the set of embeddings 314. The selection engine 320 can then identify an embedding having the minimum distance to the vertex from among the set of embeddings 314 as being the archetype embedding for the vertex.

The multi-modal data archetypes 322 generated by the archetype generation system 300B provide a way of interpreting the distribution of multi-modal data characterizing patients in the population of patients, and in particular, of efficiently capturing typical patterns expressed in the distribution of multi-modal data across the population of patients. More specifically, in the latent space, each embedding in the set of embeddings 314 can be represented as a combination (e.g., a linear combination) of the vertices of the region enclosing the set of embeddings 314, and each vertex can be represented (approximately or exactly) by an archetype embedding. Thus, the multi-modal data for each patient in the population of patients can be understood as a combination of multi-modal data archetypes corresponding to the archetype embeddings.

To facilitate interpretation of input multi-modal data characterizing a patient, the archetype generation system 300B can process the input multi-modal data using the encoder neural network 104 to generate an embedding of the input multi-modal data. The archetype generation system 300B can then determine a respective coefficient (i.e., numerical value) for each archetype embedding such that linearly combining the archetype embeddings in accordance with the coefficients yields the embedding of the input multi-modal data. The archetype generation system 300B can then provide an output that identifies: (i) each multi-modal data archetype 322, and (ii) for each multi-modal data archetype, the value of the coefficient of the corresponding archetype embedding in the latent space. The values of the coefficients can enable a user to interpret the contribution of each multi-modal data archetype to the input multi-modal data.

The multi-modal data archetypes 322 are generally high-dimensional collections of modality feature representations that can be challenging to visually interpret. To address this issue, the archetype generation system 300B uses the representation engine 306 to generate a respective archetype representation 324 for each multi-modal data archetype 322. Example techniques for generating archetype representations 324 using a representation engine 306 are described in more detail above with reference to FIG. 3A.

Figure 4C:
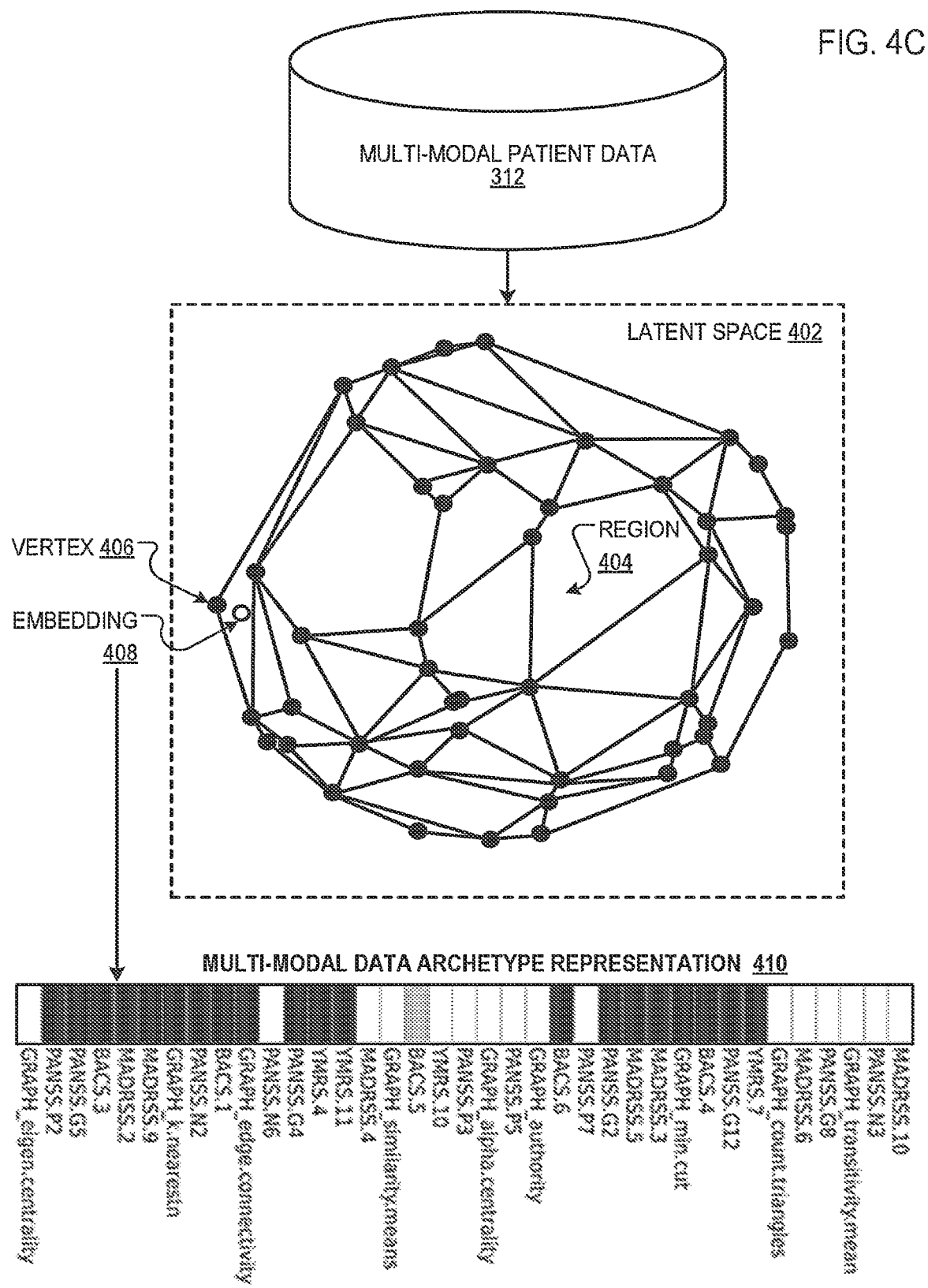

FIG. 4C illustrates an example of generating multi-modal data archetypes using the archetype generation system 300B described above with reference to FIG. 3B. For each patient in a population of patients, the archetype generation system 300B obtains multi-modal data 312 characterizing the patient, and processes the multi-modal data 312 characterizing the patient using an encoder neural network to generate a corresponding embedding in a latent space 402. The archetype generation system 300B thus generates a set of multi-modal data embeddings in the latent space, i.e., where the set of embeddings includes a respective multi-modal data embedding for each patient in the population of patients.

The archetype generation system 300B processes the set of embeddings to generate region parameters defining a region 404 of the latent space that encloses the set of embeddings, e.g., a convex hull of the set of embeddings. The archetype generation system 300B can identify a set of vertices of the region 404 (e.g., the vertex 406), and identify a respective "archetype" embedding corresponding to each vertex (e.g., the embedding 408), e.g., as the embedding that has minimum distance to the vertex (from among the embeddings in the set of embeddings). For each archetype embedding, the archetype generation system 300B can identify the multi-modal data represented by the archetype embedding as being a multi-modal data archetype. The archetype generation system 300B can generate a respective multi-modal data archetype representation 410 corresponding to each multi-modal data archetype, e.g., as an interpretable representation of the multi-modal data archetype, e.g., using the techniques described above with reference to FIG. 3A.

Figure 5:
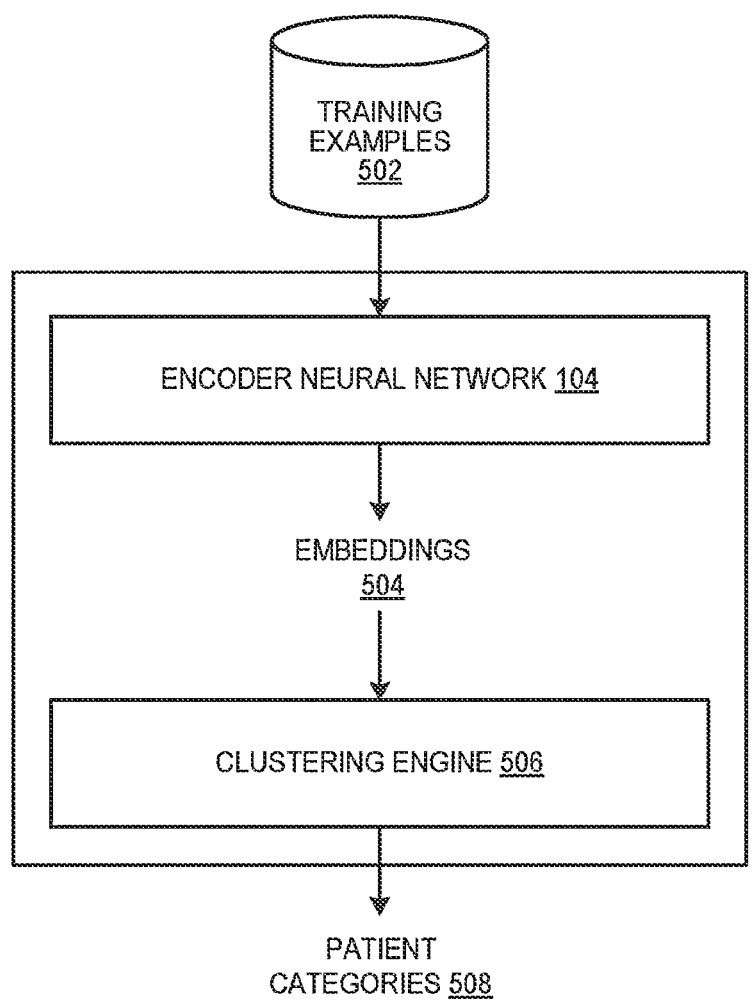
FIG. 5 shows an example patient clustering system.

FIG. 5 shows an example patient clustering system 500. The patient clustering system 500 is an example of a system implemented as computer programs on one or more computers in one or more locations in which the systems, components, and techniques described below are implemented.

The patient clustering system 500 processes a set of training examples 502 that each include multi-modal data characterizing a respective patient from a population of patients to determine a set of patient categories 508. The patient clustering system 500 also assigns each patient from the population of patients to a respective patient category 508.

The patient clustering system 500 determines the patient categories 508 and the assignment of patients to respective patient categories 508 using an encoder neural network 104 (as described with reference to FIG. 1 and FIG. 2) and a clustering engine 506. Prior to being used by the patient clustering system 500, the encoder neural network 104 is jointly trained, along with a decoder neural network, e.g., by the training system described with reference to FIG. 9. The clustering engine 506 will be described in more detail below.

The patient clustering system 500 processes the multi-modal data included in each training example using the encoder neural network 104 to generate an embedding 504 of the multi-modal data included in the training example 502.

The patient clustering system 500 then provides the embeddings 504 of the multi-modal data from the training examples 502 to the clustering engine 506. The clustering engine 506 performs a clustering operation on the embeddings 504 to generate a partition of the set of embeddings into multiple groups, referred to as "clusters," that each include multiple embeddings 504.

Generally, the clustering engine 506 performs a clustering operation that encourages the embeddings in the same cluster to be more similar (accordingly to some similarity measure in the latent space) than embeddings in different clusters. The clustering engine 506 can cluster the embeddings 504 using any appropriate clustering operation, e.g., a k-means clustering operation, an expectation maximization clustering operation, a hierarchical agglomerative clustering operation, or a spectral clustering operation. The numbers of clusters generated by the clustering engine 506 can be, e.g., a predefined hyper-parameter that is specified by a user of the patient clustering system, or determined dynamically by the clustering engine 506 during clustering.

In some implementations, prior to performing the clustering operation on the embeddings 504, the patient clustering system 500 can apply a projection operation to each embedding 504 to remove one or more specified dimensions of the embedding 504. Thus, in these implementations, the clustering engine 506 clusters projected embeddings 504 having fewer dimensions than the original embeddings 504 generated by the encoder neural network 104.

The dimensions to be removed from the embeddings 504 can be specified, e.g., by a user of the patient clustering system 500, through a user interface (e.g., a graphical user interface) made available to the user on a user device.

For example, the patient clustering system 500 can use the archetype generation system 300 described with reference to FIG. 3 to generate, for each dimension of the latent space, a respective multi-modal data archetype representing the dimension of the latent space. The patient clustering system 500 can provide the multi-modal data archetypes (and/or interpretable archetype representations of the multi-modal data archetypes, as described with reference to FIG. 3) to the user, through the user interface, for use by a user assessing which (if any) dimensions should be removed from the embeddings 504. A user may determine that a dimension of the embeddings should be removed, e.g., if the multi-modal data archetype for the dimension defines multi-modal data that the user identifies as being substantially irrelevant to a medical condition of interest. The user can provide an input, through the user interface, specifying one or more dimensions to be removed from the embeddings 504. In response to response to receiving the input from the user, the patient clustering system 500 can remove the specified dimensions from the embeddings 504.

In some implementations, the machine learning system can perform an automated process to determine that one or more dimensions can be removed from the embeddings 504 (and, more generally, the latent space). For instance, for each dimension of the latent space, the machine learning system process the multi-modal data archetype corresponding to the dimension of the latent space to determine whether a criterion for removal is satisfied. In response to determining that the criterion for removal is satisfied, the machine learning system can remove the dimension from the latent space, and in particular, can remove the dimension from each of the embeddings in the latent space. The machine learning system can implement any appropriate criterion for removal of a dimension of the latent space. For instance, the machine learning system can determine that a dimension satisfies a criterion for removal from the latent space if a feature dimension of the corresponding multi-modal data archetype satisfies a threshold. Generally, the machine learning system can implement appropriate criteria that result in the removal of dimensions of the latent space that are predicted to be substantially irrelevant to a medical condition. Removing a dimension from the latent space can refer to applying projection operations to remove the dimension from embeddings generated by the encoder neural network. Removing dimensions from the latent space can result in reduced consumption of computational resources, e.g., by reducing the memory requirements to store embeddings in the latent space, and by reducing compute requirements for clustering embeddings in the latent space.

Applying a projection operation to remove one or more specified dimensions of the embeddings 504 can reduce consumption of computational resources, e.g., memory and computing power, during clustering. Removing dimensions of the embeddings 504 corresponding to multi-modal data archetypes that are identified as being substantially irrelevant to a medical condition of interest can also increase the relevance of the clusters to the medical condition. For example, removing dimensions identified as being substantially irrelevant to a medical condition can increase the likelihood that embeddings in the same cluster correspond to patients that share characteristics relevant to the medical condition.

In some implementations, to cluster the embeddings 504, the clustering engine 506 can designate certain embeddings 504 as being "archetype" embeddings, where each archetype embedding represents a respective cluster. For each embedding 504, the clustering engine 506 can determine a respective distance between the embedding 504 and each archetype embedding, and then assign the embedding 504 to the cluster represented by the archetype embedding having minimum distance to the embedding 504. The clustering engine 506 can thus partition the set of embeddings 504 into a number of clusters equal to the number of archetype embeddings, where each archetype embedding represents a respective cluster, and where each embedding is assigned to the cluster represented by the archetype embedding having minimum distance from the embedding. The clustering engine 506 can measure distances between embeddings in the latent space using any appropriate distance measure, e.g., a Euclidean distance measure or an $L_1$ distance measure. The number of embeddings 504 designated as being archetype embeddings can be significantly smaller than the total number of embeddings 504, e.g., by one or more orders or magnitude.

The clustering engine 506 can determine that an embedding 504 should be designated as an archetype embedding using any appropriate criteria. An example process for identifying archetype embeddings is described in more detail with reference to FIG. 3B. Briefly, the clustering engine can identify a region of the latent space that encloses the set of embeddings (e.g., a convex hull of the set of embeddings), identify a set of vertices of the region, and determine a respective archetype embedding corresponding to each vertex of the region. For each vertex of the region, the clustering engine can identify the archetype embedding corresponding to the vertex as being an embedding 504 having minimum distance to the vertex, i.e., from among the set of embeddings 504.

Clustering the embeddings 504 with reference to a set of archetype embeddings, e.g., that are identified by the example process described with reference to FIG. 3B, can enable the clustering engine 506 to perform the clustering more efficiently than would otherwise be possible. In particular, clustering the embeddings 504 with reference to a set of archetype embeddings can be performed in a single parallelizable computational step, in contrast to clustering techniques that rely on performing a large number of serial clustering iterations.

The patient clustering system 500 identifies each cluster of embeddings 504 generated by the clustering engine 506 as representing a respective patient category 508. The patient clustering system 500 further identifies each patient in the population of patients as being included in the patient category represented by the cluster that includes the embedding of the multi-modal data characterizing the patient.

The patient clustering system 500 can provide the patient categories 508 for use by a cluster analysis system, as will be described in more detail with reference to FIG. 6, and a patient classification system, as will be described in more detail with reference to FIG. 7A.

Figure 6:
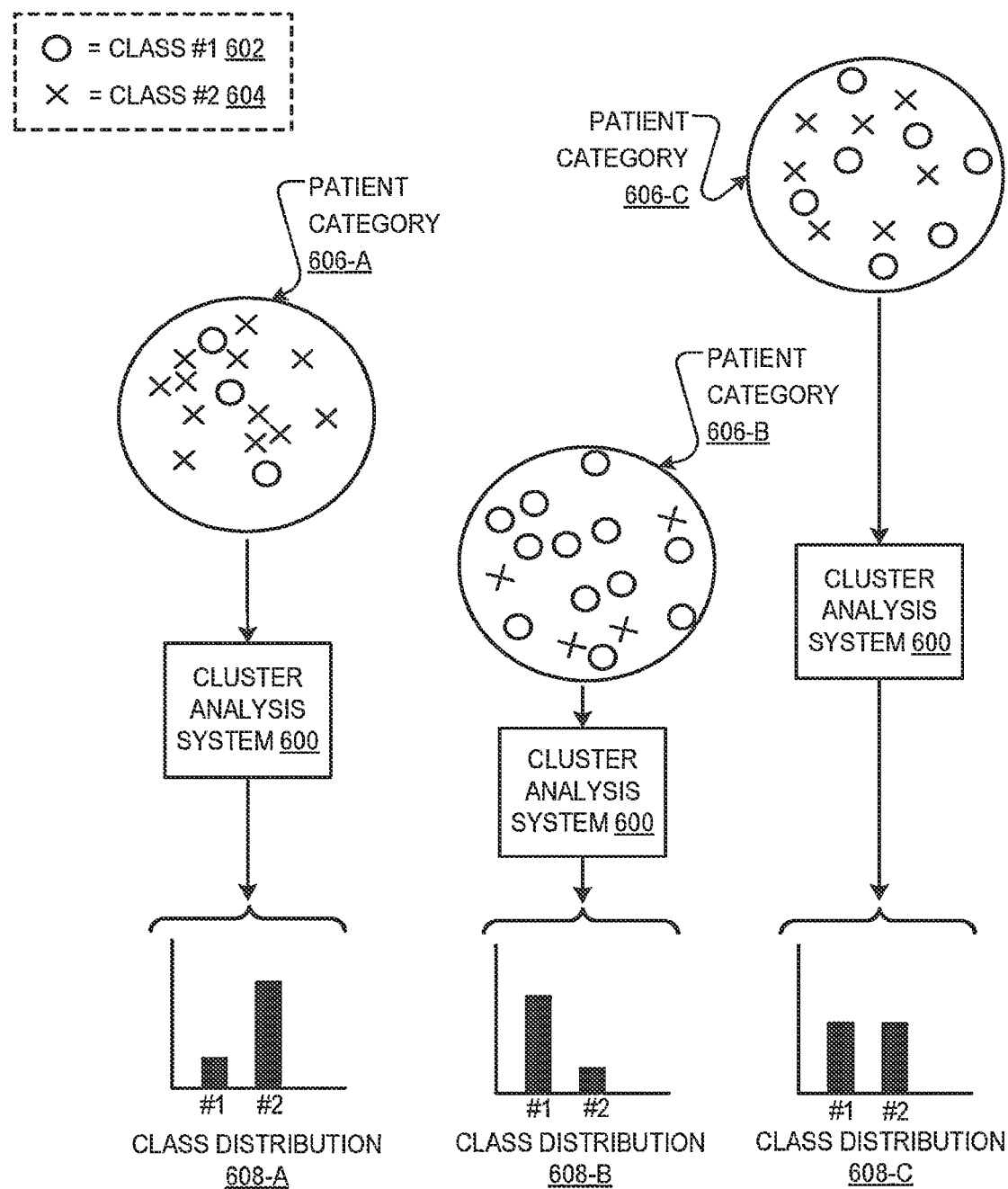
FIG. 6 shows an example cluster analysis system.

FIG. 6 shows an example cluster analysis system 600. The cluster analysis system 600 is an example of a system implemented as computer programs on one or more computers in one or more locations in which the systems, components, and techniques described below are implemented.

The cluster analysis system 600 receives, from the patient clustering system 500 described with reference to FIG. 5, data defining a set of patient categories. Each patient category represents a respective cluster of embeddings in a latent space, where each embedding represents multi-modal data characterizing a patient included in the patient category.

Each patient included in each patient category can be associated with a class from a set of classes. A few examples of possible classes are described next.

In one example, the set of classes can include one class indicating that a patient is classified as having responded to a medical treatment, and another class indicating that a patient is classified as having not responded to the medical treatment. The medical treatment can involve, e.g., administering a drug to a patient. A patient can be said to have "responded" to a medical treatment, e.g., if applying the medical treatment to the patient caused at least a predefined threshold level of improvement in the medical condition of the patient.

As another example, the set of classes can include one class indicating that a patient is classified as having experienced significant side effects after receiving a medical treatment, and another class indicating that a patient is classified as having not experienced significant side effects after receiving the medical treatment.

As another example, the set of classes can include one class indicating that a patient has been diagnosed with a medical condition, and another class indicating that a patient has not been diagnosed with the medical condition. The medical condition can be, e.g., a psychiatric condition, e.g., depression or schizophrenia.

FIG. 6 provides an illustration of patient categories 606-A, 606-B, and 606-C that each represent a respective cluster of embeddings in the latent space. In the illustration, each embedding in a first class ("class #1" 602) is represented by an O token, and each embedding in a second class ("class #2" 604) is represented by an X token.

The cluster analysis system 600 generates a respective class distribution corresponding to each patient category. The class distribution for a patient category defines, for each class, a respective fraction of the patients included in the patient category that are associated with the class.

In the example illustrated in FIG. 6, the cluster analysis system 600 generates class distribution 608-A for patient category 606-A, class distribution 608-B for patient category 606-B, and class distribution 608-C for patient category 606-C. It can be appreciated that patients included in patient category 606-A are predominately associated with class #2, patients included in patient category 606-B are predominately associated with class #1, and patients included in patient category 606-C are evenly spread between class #1 and class #2.

The class distributions generated by the cluster analysis system 600 can be used in conjunction with a patient classification system as a basis for making inferences about patients and for making clinical decisions related to patient care, as will be described in more detail with reference to FIG. 8.

Figure 7A:
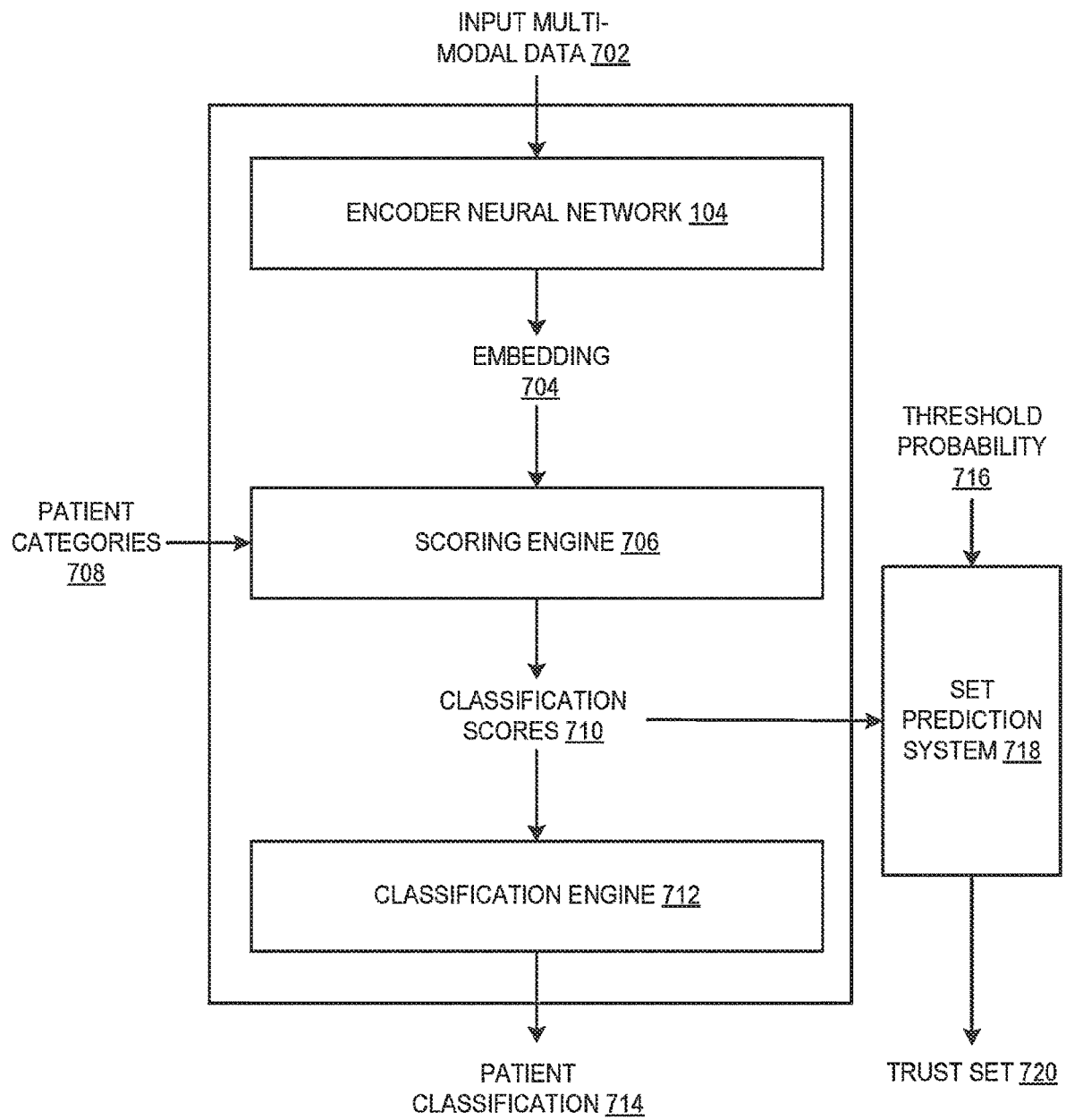
FIG. 7A shows an example patient classification system.

FIG. 7A shows an example patient classification system 700. The patient classification system 700 is an example of a system implemented as computer programs on one or more computers in one or more locations in which the systems, components, and techniques described below are implemented.

The patient classification system 700 processes input multi-modal data 702 characterizing a patient to generate a patient classification 714 that classifies the patient as being included in a patient category from a set of patient categories 708.

The set of patient categories 708 can be determined by the patient clustering system 500 described with reference to FIG. 5. Each patient category 708 represents a cluster of embeddings in the latent space, where each embedding represents multi-modal data characterizing a respective patient from a population of patients, referred to as "training" patients for convenience, as described above.

The patient classification system 700 generates the patient classification 714 using an encoder neural network 104 (e.g., as described with reference to FIG. 1 and FIG. 2), a scoring engine 706, and a classification engine 712. Prior to being used by the patient classification system 700, the encoder neural network 104 is jointly trained, along with a decoder neural network, e.g., by the training system described with reference to FIG. 9. The scoring engine 706 and the classification engine 712 will be described in more detail below.

The encoder neural network processes the input multi-modal data 702 to generate an embedding 704 of the input multi-modal data 702 in the latent space.

The scoring engine 706 determines, for each patient category 708, a respective classification score 710 for the patient category 708 based on the embedding 704 of the input multi-modal data 702. The scoring engine 706 can determine the classification scores 710 in any of a variety of possible ways. A few example techniques for determining the classification scores 710 are described in more detail next.

In some implementations, to determine the classification score 710 for a patient category 708, the scoring engine 706 determines a "centroid" embedding for the patient category, e.g., by averaging (or otherwise combining) the embeddings included in the cluster of embeddings represented by the patient category. The scoring engine 706 then determines the classification score 710 for the patient category 708 by computing a similarity measure between: (i) the embedding 704 of the input multi-modal data 702, and (ii) the centroid embedding for the patient category 708. The similarity measure can be, e.g., a $L_2$ similarity measure, a cosine similarity measure, or any other appropriate similarity measure.

In some implementations, to determine the classification score 710 for a patient category 708, the scoring engine 706 fits the parameters of a probability distribution to the embeddings included in the cluster of embeddings represented by the patient category. For example, the probability distribution can be a Normal distribution, the parameters of the probability distribution can be the mean and covariance parameters of the Normal distribution, and the scoring engine 706 can fit the mean and covariance parameters of the Normal distribution using any appropriate fitting technique, for example, a maximum likelihood estimation (MLE) technique. The scoring engine 706 then determines the classification score 710 for the patient category by computing the likelihood of the embedding 704 of the input multi-modal data 702 under the probability distribution.

In some implementations, the scoring engine 706 generates the classification scores 710 using a classification machine learning model that is configured to receive an embedding from the latent space, and to process the embedding to generate a set of classification score 710 for each patient category 708. The classification score 710 for a patient category can represent a likelihood that the patient is included in the patient category.

The classification machine learning model can be appropriate machine learning model, e.g., a neural network model, a random forest model, or a support vector machine (SVM) model. For example, the classification machine learning model can be a neural network model that includes any appropriate types of neural network layers (e.g., fully-connected layers, convolutional layers, or attention layers) in any appropriate numbers (e.g., 1 layer, 5 layers, or 10 layers) and connected in any appropriate configuration (e.g., as a linear sequence of layers).

The patient classification system 700 can train the classification machine learning model on a set of training data that includes multiple training examples. Each training example corresponds to a respective training patient and specifies: (i) the embedding, generated by the encoder neural network 104, of the multi-modal data characterizing the training patient, and (ii) a label identifying the patient category 708 of the training patient. As described above, the patient category of a training patient identifies the cluster of embeddings (e.g., as generated by the patient clustering system described with reference to FIG. 5) that includes the embedding of the multi-modal data characterizing the training patient.

The patient classification system 700 can train the classification machine learning model on the training data using any appropriate machine learning training technique. For example, if the classification machine learning model is a neural network model, then the patient classification system 700 can train the neural network model on the training data using a stochastic gradient descent training technique to optimize a cross-entropy objective function (or any other appropriate objective function). Generally, the patient classification system 700 trains the classification machine learning model to, for each training example, increase the classification score generated by the classification machine learning model (i.e., as result of processing the embedding of the training patient) for the patient category that includes the training patient.

The classification engine 712 classifies the patient as being included in a corresponding patient category 708 based on the classification scores 710. For example, the scoring engine 706 can classify the patient as being included in the patient category associated with the highest classification score 710.

Optionally, in combination with or as an alternative to generating the patient classification 714, the patent classification system 700 can provide the classification scores 710 to a set prediction system 718. The set prediction system 718 can process the classification scores 710 to generate a trust set 720 for the patient. The trust set 720 specifies one or more patient categories that collectively form a proper subset of the full set of patient categories, such that the patient is predicted to be include in a patient category within the trust set 720 with at least a threshold probability 716. The threshold probability 716 can be any appropriate probability, e.g., 50%, 75%, 90%, 95%, or 99%.

In contrast to the point estimate defined by the patient classification 714, i.e., which defines a single "best guess" for the patient category of the patient, the trust set 720 can include multiple patient categories. The trust set 720 can thus account for uncertainty in the classification of the patient into a patient category. For example, if a patient classification is more uncertain, the trust set 720 can reflect the uncertainty by including a larger number of patient categories. Uncertainty in patient classification can arise from, e.g., errors and noise in the input multi-modal data, as well as ambiguity inherent in mapping complex, high-dimensional multi-modal data characterizing a patient to a discrete set of patient categories.

The trust set 720 encodes information that is complementary to the patient classification 714, and both the trust set 720 and the patient classification 714 can be used to generate clinical recommendations, as will be described in more detail below with reference to FIG. 8.

Figure 7B:
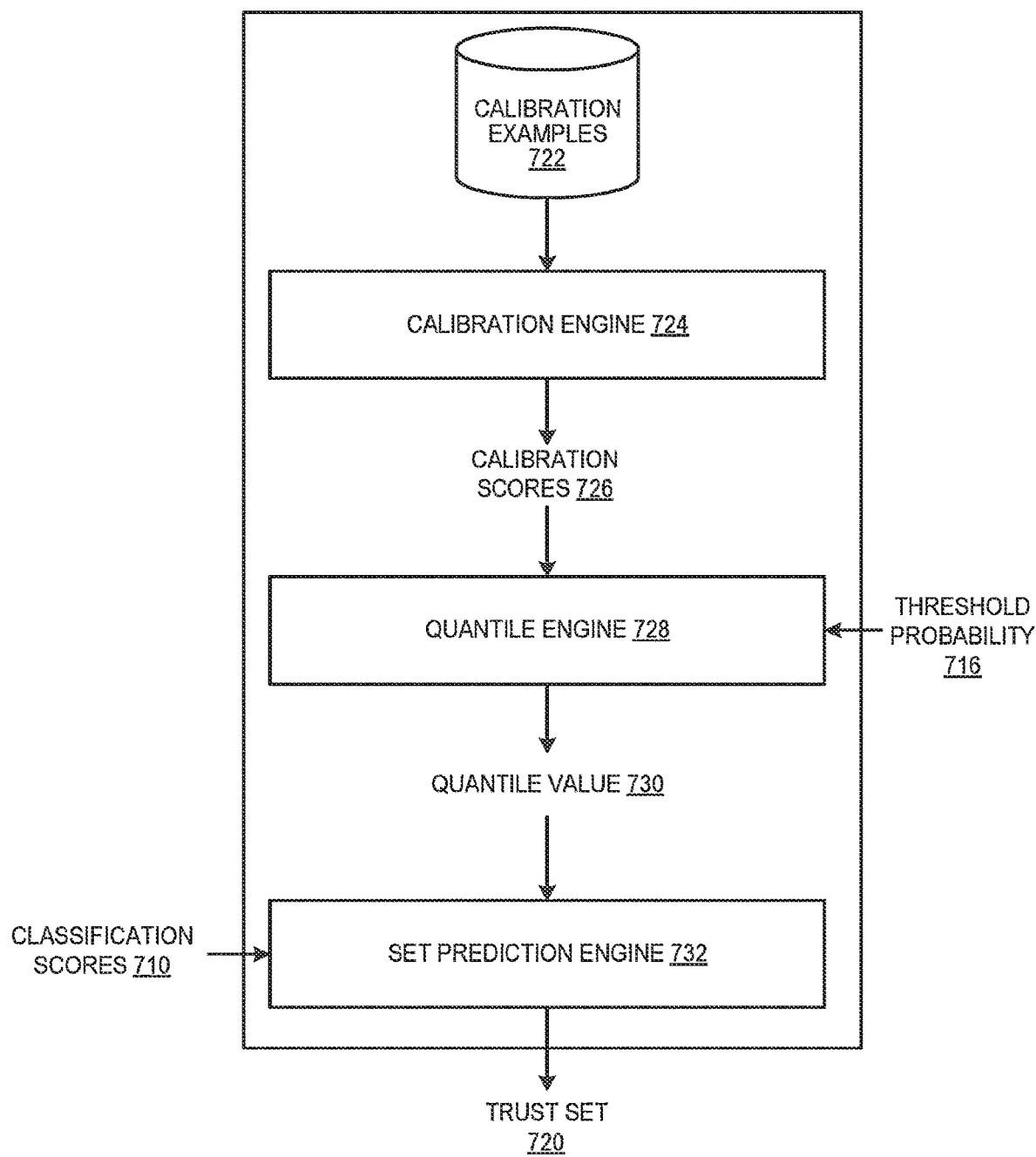
FIG. 7B shows an example set prediction system.

FIG. 7B shows an example set prediction system 718. The set prediction system 718 is an example of a system implemented as computer programs on one or more computers in one or more locations in which the systems, components, and techniques described below are implemented.

The set prediction system 718 is configured to process a set of classification scores 710 for a patient to generate a trust set 720 for the patient. The classification scores 710 for the patient include a respective score for each patient category in a set of patient categories, and can be generated, e.g., by the patient classification system 700 described with reference to FIG. 7A, or by any other appropriate system. The trust set 720 specifies a proper subset of the set of patient categories such that the patient is predicted to be include in a patient category within the trust set 720 with at least a threshold probability 716.

The set prediction system 718 generates the trust set 720 using a set of calibration examples 722, a calibration engine 724, a quantile engine 728, and a set prediction engine 732, which are each described in more detail next.

The set of calibration examples 722 is a subset of the set of training examples that are processed by the patient clustering system 500, described with reference to FIG. 5, to generate the patient categories. More specifically, the patient clustering system 500 receives a set of training examples that each correspond to a respective patient and include multi-modal data characterizing the patient. The patient clustering system 500 processes the multi-modal data from each training example to generate a corresponding embedding in a latent space, and then clusters the embeddings in the latent space to identify a set of clusters of embeddings. Each cluster defines a respective patient category, and each patient is defined as being included in the patient category represented by the cluster that includes the embedding of the multi-modal data characterizing the patient. Each calibration example 722 thus includes a set of multi-modal data characterizing a patient and is associated with a "target" patient category, i.e., determined by the patient clustering system 500.

In implementations where the patient classification system 700 generates classification scores 710 using a classification machine learning model (as described with reference to FIG. 7A), the calibration examples 722 are held-out from the training of the classification machine learning model. That is, the calibration examples 722 are not used to train the classification machine learning model.

The calibration engine 724 generates a respective calibration score 726 for each calibration example 722. To generate a calibration score 726 for a calibration example 722, the calibration engine 724 can process the multi-modal data included in the calibration example 722 to generate classification scores for the calibration example 722, e.g., using the patient classification system 700 described with reference to FIG. 7A. The calibration engine 724 can then generate the calibration score 726 for the calibration example 722 based on the classification scores for the calibration example using a scoring function that measures an error between: (i) a set of classification scores, and (ii) a patient category. In particular, the calibration engine 724 can generate the calibration score 726 for a training example by using the scoring function to measure an error between: (i) the classification scores for the calibration example, and (ii) the target patient category of the calibration example. A few examples of possible scoring functions are described next.

In one example, the scoring function s(•,•) may be given by:

$$s(f(X), y) = 1 - f(X)|_y \quad (4)$$

where f(X) are classification scores, y is a patient category, and $f(X)|_y$ is the classification score for patient category y.

In another example, the scoring function s(•,•) may be given by:

$$s(f(X), y) = \sum_{j=1}^{k} f(X)|_{\pi_j}, \text{ where } y = \pi_k \quad (5)$$

where f(X) are classification scores, y is a patient category, and $(\pi_j)_{j=1}^{K}$ is a permutation of {1, ..., K} that sorts the K classification scores from highest to lowest.

The quantile engine 728 processes the set of calibration scores 726 and the threshold probability 716 to generate a quantile value 730 as a quantile of the set of calibration scores. For example, the quantile engine 728 can generate the quantile value 730 as the a-th quantile of the set of calibration scores, where a is given by:

$$a = \frac{\lceil (n+1) \cdot p \rceil}{n} \quad (6)$$

where n is the number of calibration examples 722, [•] denotes a ceiling function, and p is the threshold probability 716.

The set prediction engine 732 processes: (i) the classification scores 710 for the patient, and (ii) the quantile value 730, to generate the trust set 720 for the patient. To determine whether a patient category is included in the trust set 720, the set prediction engine 732 can use the scoring function (as described above with reference to the calibration engine 724) to generate a "test" score for each patient category. More specifically, the set prediction engine 732 can generate a test score for a patient category by processing: (i) the classification scores 710 for the patient, and (ii) data identifying the patient category, using the scoring function. The set prediction engine 732 can then determine that each patient category is included in the trust set 720 if the test score for the patient category does not exceed the quantile value 730.

For example, if the scoring function is provided by equation (4), then the set prediction engine 732 can generate the trust set 720 as:

$$\{y : f(X)|_y \geq 1 - q\} \quad (7)$$

where y denotes patient categories, $f(X)|_y$ denotes the classification score for patient category y, and q denotes the quantile value 730.

As another example, if the scoring function is provided by equation (5), then the set prediction engine 732 can generate the trust set as:

$$\{\pi_1, \ldots, \pi_k\}, \text{ where } k = \inf\left\{k : \sum_{j=1}^{k} f(x)|_{\pi_j} \geq q\right\} \quad (8)$$

where $(\pi_j)_{j=1}^{K}$ is a permutation of {1, ..., K} that sorts the K classification scores from highest to lowest, $\{\pi_1, \ldots, \pi_k\}$ are the indices of the patient categories included in the trust set 720, $f(X)|_{\pi_j}$ is the classification score for the patient category indexed by $\pi_j$, inf{•} is the infimum operator, and q is the quantile value 730.

Generating the trust set 720 using the procedure described above can result in the patient being included in a patient category within the trust set with at least the threshold probability, irrespective of the accuracy of the patient classification system used to generate the classification scores 710.

The trust set 720 for a patient is adapted to the difficulty and uncertainty of the patient classification. For example, a trust set with a larger number of patient categories can reflect a more uncertain patient classification, while a trust set with a smaller number of patient categories can reflect a more certain classification.

Generally, the set prediction system 718 is not required to re-compute the quantile value 730 associated with a threshold probability 716 each time the set prediction system 718 generates a trust set 720 for a patient. Rather, the set prediction system 718 can compute the quantile value 730 associated with a threshold probability once, and thereafter store and reuse the quantile value 730 each time the set prediction system 718 is called upon to generate a trust set 720 based on the threshold probability 716.

Figure 8:
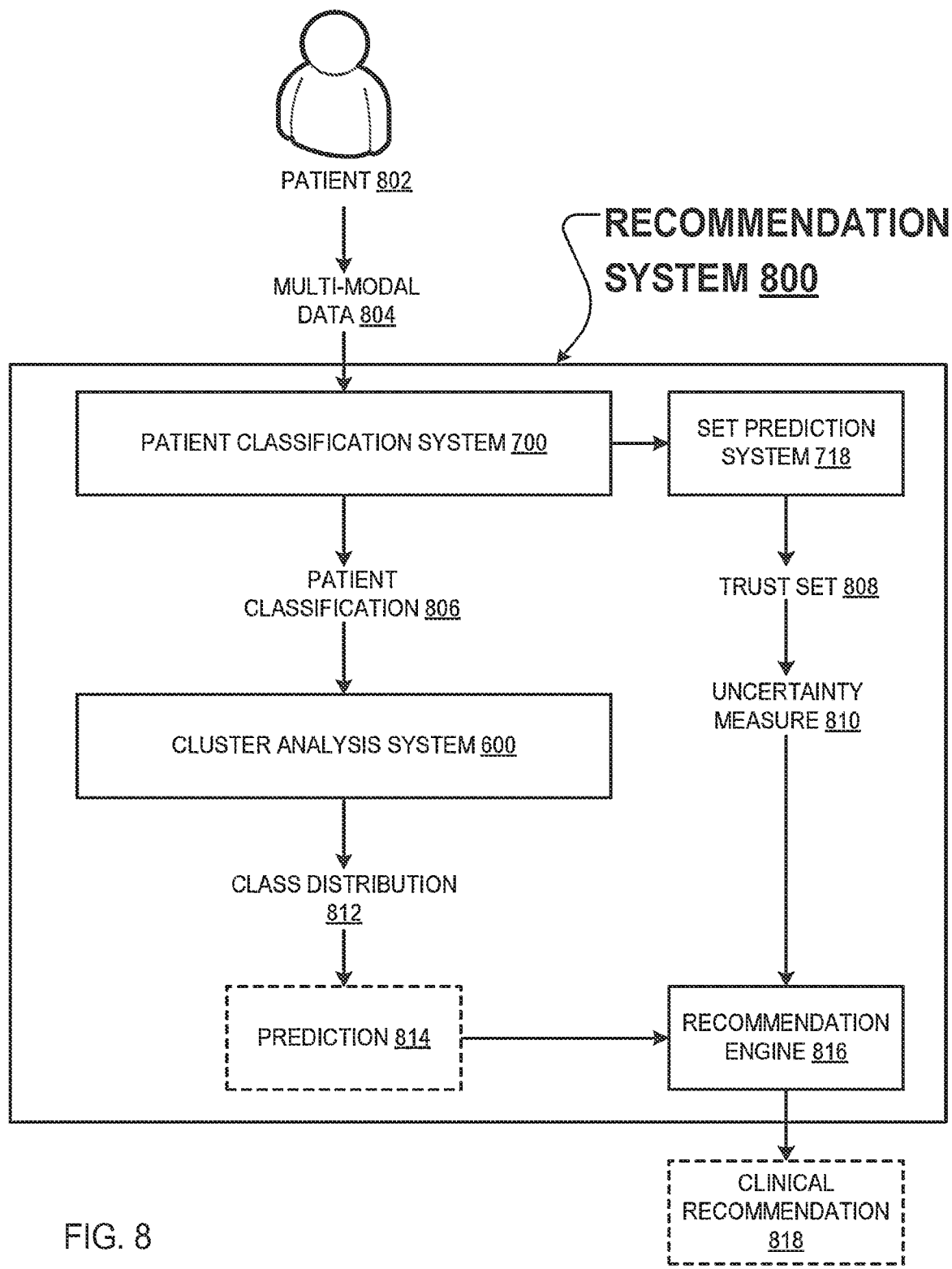
FIG. 8 illustrates an example workflow for using a patient classification system to generate predictions characterizing a patient and to make clinical decisions related to the patient.

FIG. 8 shows an example recommendation system 800. The recommendation system 800 is an example of a system implemented as computer programs on one or more computers in one or more locations in which the systems, components, and techniques described below are implemented.

The recommendation system 800 uses the patient classification system 700 (as described with reference to FIG. 7A), the cluster analysis system 600 (as described with reference to FIG. 6), the set recommendation system 800 (as described with reference to FIG. 8), and a recommendation engine 816 to generate a clinical recommendation 818 for a patient 802. The clinical recommendation 818 can be, e.g., a recommendation related to medical treatment of the patient.

In particular, the patient classification system 700 processes multi-modal data 804 characterizing the patient 802 to generate a patient classification 714 that classifies the patient as being included in a patient category from a set of patient categories.

The cluster analysis system 600 processes data identifying the patient category of the patient 802 to generate a class distribution 812. The class distribution 812 defines, for each class in a set of classes, a fraction of patients included in the patient category that are associated with the class (as described above with reference to FIG. 6).

Optionally, in combination with or as an alternative to generating the class distribution 812 based on the patient classification 714, the cluster analysis system 600 can generate a "combined" class distribution 812 using the set of classification scores generated by the patient classification system 700. In particular, as part of generating the patient classification 714, the patient classification system 700 generates a set of classification scores that includes a respective classification score for each patient category in the set of patient categories. The cluster analysis system 600 can generate a combined class distribution based on, for each patient category: (i) the classification score for the patient category, and (ii) the class distribution of the patient category.

In particular, the cluster analysis system 600 can generate the combined class distribution as a linear combination of the respective class distribution corresponding to each patient category, where the class distribution corresponding to each patient category is weighted in the linear combination by the corresponding classification score. More specifically, the combined class distribution can define a respective likelihood score for each class in a set of classes based on, for each patient category: (i) the classification score for the patient category, and (ii) the fraction of patients included in the patient category that are associated with the class. For example, the combined class distribution can define a likelihood score $L_c$ associated with each class c as:

$$L_c = \sum_{p=1}^{P} CS_p \cdot F_{p,c} \quad (9)$$

where p indexes the patient categories, P is the number of patient categories, $CS_p$ is the classification score for patient category p, and $F_{p,c}$ is the fraction of patients included in patient category p associated with class c.

In some implementations, the cluster analysis system 600 can generate the combined class distribution with reference to only a proper subset of the patient categories in the set of patient categories. For example, the cluster analysis system 600 can generate the combined class distribution with reference only to patient categories included a trust set 720 generated by the set prediction system 718, as will be described in more detail below.

The recommendation system 800 generates one or more predictions 814 characterizing the patient 802 based on the class distribution 812. A few examples of possible predictions 814 are described next.

In one example, the set of classes can include one class for patients that are classified as having responded to a medical treatment, and another class for patients that are classified as having not responded to the medical treatment. In this example, the recommendation system 800 can process the class distribution 812 for the patient category to generate a prediction 814 for a likelihood that the patient 802 will respond to the medical treatment. For example, the recommendation system 800 can determine the likelihood that the patient 802 will respond to the medical treatment as being the fraction of patients included in the patient category that responded to the medical treatment. As another example, if the class distribution is a combined class distribution (as described above), the recommendation system 800 can determine the likelihood that the patient 802 will respond to the medical treatment as being the likelihood assigned to the corresponding class by the combined class distribution.

In another example, the set of classes can include one class for patients that have been classified as having experienced significant side effects from receiving a medical treatment, and another class for patients that are classified as having not experienced significant side effects from receiving the medical treatment. In this example, the recommendation system 800 can process the class distribution 812 for the patient category to generate a prediction 814 for a likelihood that the patient 802 will experience significant side effects from receiving the medical treatment. For example, the recommendation system can determine the likelihood that the patient 802 will experience significant side effects from receiving the medical treatment as being the fraction of patients included in the patient category that experienced significant side effects from receiving the medical treatment. As another example, if the class distribution is a combined class distribution (as described above), the recommendation system 800 can determine the likelihood that the patient 802 will experience significant side effects as being the likelihood assigned to the corresponding class by the combined class distribution.

In another example, the set of classes can include one class for patients that have been diagnosed with a medical condition, and a second class for patients that have not been diagnosed with the medical condition. In this example, the recommendation system 800 can process the class distribution 812 for the patient category to generate a prediction 814 for a likelihood of the patient 802 having the medical condition. For example, the recommendation system 800 can determine the likelihood that the patient has the medical condition as being the fraction of patients included in the patient category that have been diagnosed with the medical condition. As another example, if the class distribution is a combined class distribution (as described above), the recommendation system 800 can determine the likelihood that the patient 802 has the medical condition as being the likelihood assigned to the corresponding class by the combined class distribution.

In addition to generating the prediction 814 characterizing the patient 802, the recommendation system 800 can use the set recommendation system 800 to generate a trust set 720 for the patient 802. More specifically, the set recommendation system 800 can process a set of classification scores generated by the patient classification system 700, i.e., including a respective classification score for each patient category in the set of patient categories, to generate the trust set 720. The trust set 720 specifies a proper subset of the set of patient categories such that the patient is predicted to be include in a patient category within the trust set 720 with at least a threshold probability.

The recommendation system 800 can process the trust set 720 to derive an uncertainty measure 810, i.e., a numerical value that measures an uncertainty in the patient classification 714 generated by the patient classification system 700. For example, the uncertainty measure 810 can represent a number of patient categories that are included in the trust set 720. Generally, a larger number of patient categories being included in the trust set 720 indicates a higher uncertainty in the patient classification 714.

The recommendation engine 816 can generate the clinical recommendation 818 based on: (i) the prediction 814 characterizing the patient 802, and (ii) the uncertainty measure 810 characterizing uncertainty in the patient classification 714.

More specifically, to generate the clinical recommendation 818, the recommendation engine 816 can evaluate a confidence criterion based at least in part on the uncertainty measure 810. In response to determining that the confidence criterion is satisfied, the recommendation engine 816 can map the prediction 814 characterizing the patient onto a corresponding clinical decision, and generate a clinical recommendation 818 that includes the clinical decision. (Examples of mapping a prediction 814 onto a corresponding clinical decision are described in more detail below). In response to determining that the confidence criterion is not satisfied, the recommendation engine 816 can generate a "null" clinical recommendation 818, e.g., indicating that the recommendation system 800 lacks a required level of confidence to generate a clinical recommendation 818.

The recommendation engine 816 can evaluate whether the confidence criterion is satisfied based on the uncertainty measure 810, and optionally, based on other factors as well, e.g., a number of patients included in the patient category. Generally, a larger number of patients being included in a patient category can decrease the uncertainty of a prediction 814 generated based on the inclusion of a patient in the patient category. For example, a larger number of patients being included in a patient category can decrease the effect of statistical fluctuations on the class distribution of the patient category.

A few example techniques by which the recommendation engine 816 can evaluate whether the confidence criterion is satisfied are described next.

In one example, the recommendation engine 816 can determine the confidence criterion is satisfied if the uncertainty measure 810 satisfies a threshold. For example, the recommendation engine 816 can determine that the confidence criterion is satisfied if the uncertainty measure is less than N, where N can be, e.g., 2, 3, 5, or any other appropriate positive integer value.

In another example, the recommendation engine 816 can determine the confidence criterion is satisfied only if both: (i) the uncertainty measure satisfies an uncertainty threshold, and (ii) the number of patients included in the patient category satisfies (e.g., exceeds) a threshold. The threshold number of patients can be any appropriate number of patients, e.g., 10, 100, or 1000 patients.

If the recommendation engine 816 determines that the confidence criterion is satisfied, then the recommendation engine 816 can map the prediction 814 characterizing the patient onto a corresponding clinical decision and generate a clinical recommendation 818 that includes the clinical decision, as described above. A few examples of clinical decisions corresponding to predictions 814 are described next.

In one example, a prediction 814 that the patient will respond to a medical treatment with at least a threshold likelihood (e.g., 75%, 90%, 95%, or any other appropriate threshold likelihood) can be mapped onto a clinical decision to apply the medical treatment to the patient. Conversely, a prediction 814 that the patient will respond to a medical treatment with less than the threshold likelihood can be mapped onto a clinical decision not to apply the medical treatment to the patient. (Applying the medical treatment to the patient can include, e.g., administering a drug to the patient). In some cases, the clinical decision can be implemented in practice, e.g., by applying the medical treatment to the patient.

In another example, a prediction 814 that the patient will experience significant side effects from a medical treatment with at least a threshold likelihood (e.g., 75%, 90%, 95%, or any other appropriate threshold likelihood) can be mapped onto a clinical decision not to apply the medical treatment to the patient. Conversely, a prediction 814 that the patient will experience significant side effects from the medical treatment with less than the threshold likelihood can be mapped onto a clinical decision to apply the medical treatment to the patient. In some cases, the clinical decision can be implemented in practice, e.g., by applying the medical treatment to the patient.

In another example, a prediction 814 that the patient has a medical condition with at least a threshold likelihood (e.g., 75%, 90%, 95%, or any other appropriate threshold likelihood) can be mapped onto a clinical decision to diagnose the patient with the medical condition. Conversely, a prediction 814 that the patient has the medical condition with less than the threshold likelihood can be mapped onto a clinical decision not to diagnose the patient with the medical condition.

After generating the clinical recommendation 818, the recommendation system 800 can output the clinical recommendation 818, e.g., by providing the clinical recommendation 818 to a user of the system, e.g., by way of a user interface made available to the user.

As described above, the recommendation system 800 can process multi-modal data 804 for patients 802 to generate corresponding predictions 814 and/or clinical recommendations 818, in relation to whether a patient will respond to a medical treatment, will experience significant side effects from a medical treatment, or should be diagnosed with a medical condition. In certain cases, particular combinations of multi-modal data modalities may be particularly effective for generating predictions and clinical recommendations for certain medical conditions. A few examples of possible combinations of data modalities that can be processed by the recommendation system to generate predictions and/or clinical recommendations for certain medical conditions are described next. It will be appreciated that these examples are provided for illustrative purposes only and do not limit the potential use cases or applications of the techniques described in this specification.

In some implementations, the recommendation system 800 processes gene expression data, or clinical scale data (characterizing ALS severity, or respiratory function, or both), or both to generate a prediction for whether a patient with ALS will respond to a medical treatment, or a prediction for whether a patient with ALS will experience significant side effects from a medical treatment.

In some implementations, the recommendation system 800 processes a combination of one or more of: clinical scale data (e.g., obtained from clinical interviews with the patient), EEG data, gene expression data, or neuroimaging data (e.g., fMRI data, or PET data, or both), to generate a prediction for whether a patient with schizophrenia will respond to a medical treatment, or a prediction for whether a patient with schizophrenia will experience significant side effects from a medical treatment, or a prediction for whether a patient has schizophrenia.

In some implementations, the recommendation system 800 processes a combination of one or more of: clinical scale data (e.g., obtained from clinical interviews with the patient), gene expression data, neuroimaging data (e.g., fMRI data, or PET data, or both), or protein expression data, to generate a prediction for whether a patient with Parkinson's disease will respond to a medical treatment, or a prediction for whether a patient with Parkinson's disease will experience significant side effects from a medical treatment, or a prediction for whether a patient has Parkinson's disease.

In some implementations, the recommendation system 800 processes a combination of one or more of: MRI data, EEG, data, or clinical scales data (e.g., obtained from clinical interviews with the patient), to generate a prediction for whether a patient with major depressive disorder (MDD) will respond to a medical treatment, or to generate a prediction for whether a patient with MDD will experience significant side effects from a medical treatment, or a prediction for whether a patient has MDD.

Figure 9:
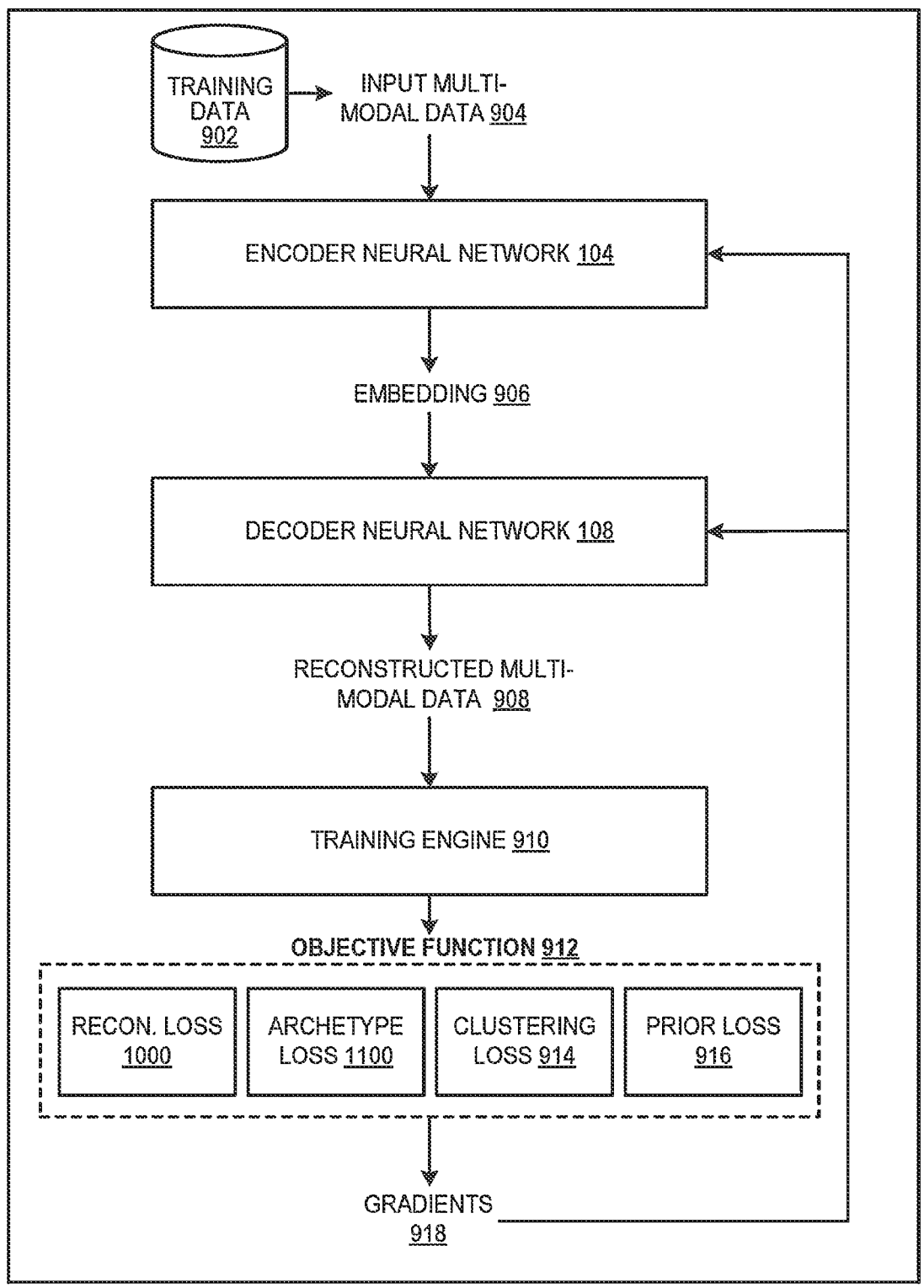
FIG. 9 shows an example training system.

FIG. 9 shows an example training system 900. The training system 900 is an example of a system implemented as computer programs on one or more computers in one or more locations in which the systems, components, and techniques described below are implemented.

The training system 900 jointly trains the encoder neural network 104 and the decoder neural network 108 (as described with reference to FIG. 1 and FIG. 2) on a set of training data 902 that includes multiple training examples. Each training example corresponds to a respective patient and includes multi-modal data characterizing the patient.

The encoder neural network 104 is configured to process input multi-modal data characterizing a patient to generate an embedding of the input multi-modal data in a latent space. For example, the encoder neural network can process the input multi-modal data to generate parameters of a posterior probability distribution over the latent space, e.g., mean and covariance parameters of a Normal distribution over the latent space. The encoder neural network 104 can then sample an embedding from the latent space in accordance with the posterior probability distribution over the latent space.

The decoder neural network 108 is configured to process an embedding from the latent space to generate output multi-modal data.

To jointly train the encoder neural network 104 and the decoder neural network 108 on the training data 902, the training system 900 samples a batch (i.e., set) of training examples from the training data 902. The training system 900 then jointly trains the encoder neural network 104 and the decoder neural network 108 on each training example from the batch.

To jointly train the encoder neural network 104 and the decoder neural network 108 on a training example from the batch, the training system 900 processes the input multi-modal data 904 from the training example using the encoder neural network 104, in accordance with values of a set of encoder neural network parameters, to generate an embedding 906 of the input multi-modal data 904. The training system 900 then processes the embedding 906 of the input multi-modal data 904 using the decoder neural network 108, in accordance with values of a set of decoder neural network parameters, to generate "reconstructed" multi-modal data 908 that defines a reconstruction (i.e., an estimate) of the input multi-modal data 904 from the training example.

A training engine 910 then determines gradients 918 of an objective function 912 that depends on the reconstructed multi-modal data 908, and uses the gradients 918 to update the current parameter values of the encoder neural network 104 and the decoder neural network 108. The training engine 910 can determine gradients of the objective function 912 with respect to the current parameter values of the encoder neural network 104 and the decoder neural network 108, e.g., using backpropagation. The training engine 910 can update the current parameter values of the encoder neural network 104 and the decoder neural network 108 using any appropriate gradient descent optimization technique, e.g., RMSprop or Adam.

The objective function 912 includes a reconstruction loss 1000, and optionally, one or more of: an archetype loss 1100, a clustering loss 914, or a prior loss 916, which are each described in more detail below. For example, the objective function $\mathcal{L}$ can be given by:

$$\mathcal{L} = \alpha_1 \cdot \mathcal{L}_r + \alpha_2 \cdot \mathcal{L}_a + \alpha_3 \cdot \mathcal{L}_c + \alpha_4 \cdot \mathcal{L}_p \qquad (10)$$

where $(\alpha_i)_{i=1}^{4}$ are scalar coefficients, $\mathcal{L}_r$ denotes the reconstruction loss 1000, $\mathcal{L}_a$ denotes the archetype loss 1100, $\mathcal{L}_c$ denotes the clustering loss 914, and $\mathcal{L}_p$ denotes the prior loss 916. In some cases, one or more of the $(\alpha_i)_{i=1}^{4}$ scalar coefficients have value zero at one or more training iterations, thereby removing corresponding terms from the objective function at the training iteration.

The reconstruction loss 1000 measures an error in the reconstructed multi-modal data 908, i.e., the reconstruction loss 1000 measures an error between: (i) the input multi-modal data 904 from the training example, and (ii) the reconstructed multi-modal data 908 generated by the decoder neural network 108. Training the encoder neural network 104 and the decoder neural network 108 using the reconstruction loss 1000 encourages the encoder neural network 104 to generate embeddings of multi-modal data that encode information characterizing properties of the multi-modal data that enable accurate reconstruction of the multi-modal data from the embeddings.

The reconstruction loss 1000 can include multiple scaling factors that each scale a respective term in the reconstruction loss 1000 that measures an error in a corresponding proper subset of the feature dimensions of the reconstructed multi-modal data 908. (As described above, the features representing multi-modal data, including reconstructed multi-modal data 908, can be understood as being organized into a set of feature dimensions.) Thus each scaling factor controls the relative importance of the error in a corresponding proper subset of the feature dimensions of the reconstructed multi-modal data 908 to the calculation of the overall error in the reconstructed multi-modal data 908.

As an example, the reconstruction loss $\mathcal{L}_r$ can have the form:

$$\mathcal{L}_r = \sum_{i=1}^{n} \beta_i \cdot \mathcal{L}_r(A_i) \qquad (11)$$

where for each $i \in \{1, \ldots, n\}$: $A_i$ designates a respective proper subset of the feature dimensions of the multi-modal data, $\mathcal{L}_r(A_i)$ denotes an error in the proper subset $A_i$ of the feature dimensions in the reconstructed multi-modal data 908, and $\beta_i$ is a scaling factor corresponding to the proper subset $A_i$ of the feature dimensions of the multi-modal data. Generally, each of the scaling factors $(\beta_i)_{i=1}^{n}$ have different values. The error $\mathcal{L}_r(A_i)$ in a proper subset $A_i$ of the feature dimensions in the reconstructed multi-modal data measures an error between: (i) the proper subset $A_i$ of the feature dimensions in the input multi-modal data 904 from the training example, and (ii) the proper subset $A_i$ of the feature dimensions in the reconstructed multi-modal data 908 generated by the decoder neural network 108. The error between can be measured, e.g., using an $L_1$ similarity measure, an $L_2$ similarity measure, a cosine similarity measure, or any other appropriate measure.

The value of each scaling factor in the reconstruction loss 1000 can be set based on a relevance of the corresponding proper subset of the feature dimensions of the multi-modal data to a particular medical condition. In particular, scaling factors corresponding to proper subsets of the feature dimensions of the multi-modal data that are more relevant to the medical condition can be set to higher values than scaling factors corresponding to less relevant proper subsets of the feature dimensions of the multi-modal data.

The values of the scaling factors in the reconstruction loss 1000 can be determined with reference to any appropriate medical condition, e.g., a psychiatric condition, e.g., depression or schizophrenia.

A few example techniques for determining the values of the scaling factors in the reconstruction loss 1000 are described in more detail next.

In some implementations, the relevance of a feature dimension of the multi-modal data to a medical condition is based on a relevance of the feature dimension to a treatment for the medical condition. A few example techniques for determining the relevance of feature dimensions of the multi-modal data to a treatment for a medical condition are described next.

In one example, the training system 900 determines the relevance of certain feature dimensions of the multi-modal data to a treatment for a medical condition using a "pre/post dataset." The pre/post dataset includes, for each of one or more "reference" patients, a respective "pre-" value and a respective "post-" value for each feature in a set of "reference" features characterizing the reference patient. The pre-value of each reference feature is measured prior to the reference patient receiving the medical treatment. The post-value of each reference feature is measured after the reference patient receives the medical treatment.

The pre/post dataset can include pre- and post-values for any appropriate references features, in particular, for reference features of any appropriate modality. In one example, the reference features in the pre/post dataset can include fMRI features, e.g., features representing a functional connectivity matrix, features representing a projection of a functional connectivity matrix onto a vector, or features representing graph statistics characterizing a graph derived from a functional connectivity matrix, as described above. In another example, the reference features in the pre/post dataset can include EEG features, e.g., features representing a Fourier transform of an EEG voltage waveform. In another example, the reference features can be clinical scale features, e.g., characterizing patient mood and personality.

The training system 900 can determine a respective scaling factor for each reference feature that characterizes a relevance of the reference feature to the medical conditioned based on, for each reference patient, a difference between the pre- and post-values of the reference feature for the reference patient. For example, the training system 900 can determine a respective scaling factor in the reconstruction loss for each feature dimension that corresponds to a reference feature based on a measure of central tendency (e.g., average or median) of the difference between the pre- and post-values of the reference feature for the reference patients. As part of determining the scaling factor in the reconstruction loss for a reference feature, the training system 900 can apply one or more transformation operations to the measure of central tendency of the difference between the pre- and post-values of the reference feature for the reference patients. For example, the training system 900 can apply an absolute value transformation to the measure of central tendency of the difference between the pre- and post-values of the reference feature, e.g., to ensure that the resulting scaling factor is non-negative.

A change in the value of a reference feature after a medical treatment is applied to a patient can, in some cases, be at least partially attributed to the effect of the medical treatment. For example, applying a drug to patient to treat a psychiatric condition (e.g., psychosis or schizophrenia) may affect patterns of neural activity in the brain of the brain of the patient, and these changes may be reflected in fMRI features. In particular, fMRI features that change significantly as a result of applying the drug to the patient may measure properties of the brain of the patient that are affected by the application of the drug. Thus the training system 900 can use the pre/post dataset to determine scaling factors for reference fMRI features (or, more generally, for any appropriate features) that reflect the relevance of those features to the drug.

The pre/post dataset can measure values of reference features for any appropriate set of reference patients. The number of reference patients included in the pre/post dataset can be, e.g., one patient, 10 patients, 1000 patients, or any other appropriate number of patients. The set of reference patients can be non-overlapping or only partially overlapping with the set of "training" patient that provide multi-modal data included in the training data 902 used for training the encoder neural network 104 and the decoder neural network 108. Determining scaling factors in the reconstruction loss using the pre/post dataset thus provides a way for the training system 900 to incorporate relevant information encoded in the pre- and post-feature value measurements for the reference patients into the training by way of the reconstruction loss.

In another example, the training system 900 determines the relevance of certain feature dimensions of the multi-modal data to a drug that can applied to treat a medical condition using positron emission tomography (PET) imaging. In particular, prior to administering the drug to a reference patient, the drug can be labeled (i.e., tagged) with a radioactive tracer element (e.g., technetium-99m). After the drug is administered, one or more PET images of the reference patient can be captured, where the intensity of a voxel in a PET image can be correlated with the presence of the radioactive tracer (and, by extension, the drug) at a corresponding location in the reference patient. In some cases, the PET images can show the brain of the reference patient, and thus characterize the spatial distribution of the drug in the brain of the reference patient.

The training system 900 can process the PET images to determine scaling factors in the reconstruction loss. For example, the training system 900 can process the PET images to generate a "penetration score" for each brain region in a set of brain regions that collectively define a parcellation of the brain of the reference patient. The penetration score for a brain region characterizes the concentration of the drug in the brain region. The training system 900 can generate the penetration score for a brain region, e.g., by computing a measure of central tendency (e.g., an average or median) of the intensities of the voxels included in the brain region in the PET images.

The penetration score (i.e., as determined from PET images) for a brain region can provide a scaling factor in the reconstruction loss for feature dimensions (i.e., in multi-modal data for a patient) that characterize the brain region. A few examples of using penetration scores as scaling factors in the reconstruction loss are described next.

For example, the training system 900 can determine the scaling factor in the reconstruction loss for a feature dimension that represents entry (i, j) in a functional connectivity matrix (i.e., representing the correlation between blood flow curves for brain region i and brain region j in a parcellation) as a product of: (i) the penetration score for brain region i, and (ii) the penetration score for brain region j. As another example, the training system 900 can determine the scaling factor for a multi-modal feature dimension that represents entry a sum of the entries in row i or column i in a functional connectivity matrix as the penetration score for brain region i. Thus, in these examples, the training system 900 uses PET imaging to determining scaling factors in the reconstruction loss for feature dimensions corresponding to fMRI features.

As another example, the training system 900 can determine the scaling factor in the reconstruction loss for a feature dimension that represents water diffusion in a brain region (e.g., as measured from diffusion tensor imaging (DTI)) as the penetration score for the brain region.

In some implementations, the training system 900 determines the relevance of certain feature dimensions of the multi-modal data to a medical condition based on a correlation between: (i) the value of the feature dimension, and (ii) diagnosis with the medical condition, for a set of reference patients. In particular, the training system 900 can set the value of the scaling factor for each corresponding feature dimension in the reconstruction loss based on the correlation between the value of the feature dimension and diagnosis with the medical condition in the reference patients. A few examples of determining scaling factors in the reconstruction loss in this manner are described next.

In one example, each reference patient may be associated with: (i) genomic data that defines a respective expression level (i.e., in the reference patient) of each gene in a set of genes, and (ii) a label indicating whether the reference patient has been diagnosed with the medical condition. The training system 900 can determine, for each gene, a correlation between the expression level of the gene and diagnosis with the medical condition in the reference patients. The training system 900 can then set the value of the scaling factor for each multi-modal feature dimension that measures the expression level of a gene based on the determined correlation between the expression level of the gene and diagnosis with the medical condition in the reference patients.

In another example, each reference patient may be associated with: (i) proteomic data that defines a respective expression level (i.e., in the reference patient) of each protein in a set of proteins, and (ii) a label indicating whether the reference patient has been diagnosed with the medical condition. The training system 900 can determine, for each protein, a correlation between the expression level of the protein and diagnosis with the medical condition in the reference patients. The training system 900 can then set the value of the scaling factor for each multi-modal feature dimension that measures the expression level of a protein based on the determined correlation between the expression level of the protein and diagnosis with the medical condition in the reference patients.

The scaling factors in the reconstruction loss 1000 can be associated with any appropriate proper subsets of the feature dimensions of the multi-modal data that jointly form a partition of the feature dimensions of the multi-modal data. In some implementations, each modality in the multi-modal data is associated with a respective scaling factor in the reconstruction loss, i.e., such that each feature dimension of the multi-modal data corresponding to the same modality is associated with the same scaling factor. In other implementations, feature dimensions of the multi-modal data corresponding to the same modality can be associated with different scaling factors.

Figure 10:
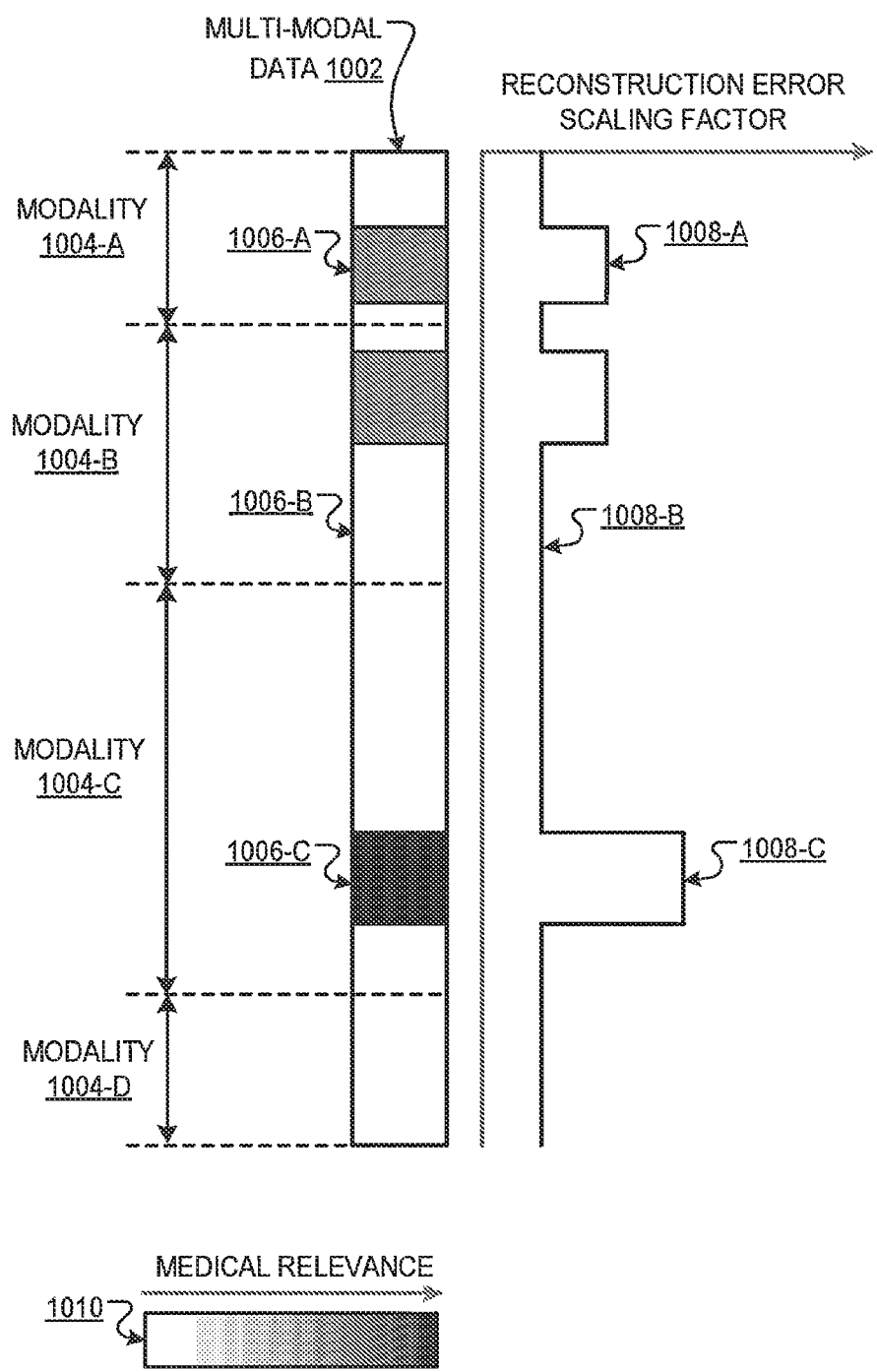
FIG. 10 illustrates an example of a reconstruction loss.

FIG. 10 illustrates an example of a reconstruction loss 1000 for a set of multi-modal data 1002. In this example, the multi-modal data 1002 includes respective feature dimensions corresponding to modalities 1004-A-1004-D. The relevance of respective subsets of the multi-modal data 1002 to a particular medical condition are illustrated by the shade, where darker shades indicate higher relevance (as illustrated by the color bar 1010). The relevance of feature dimensions of multi-modal data to a medical condition can be determined, e.g., based on their relevance to diagnosing the medical condition, as described above.

FIG. 10 further illustrates the values of scaling factors in the reconstruction loss 1000 corresponding to each feature dimension of the multi-modal data 1002. For example, the proper subset 1006-A of the feature dimensions of the multi-modal data is associated with scaling factor value 1008A-A, the proper subset 1006-B of the feature dimensions of the multi-modal data is associated with scaling factor value 1008-B, and the proper subset 1006-C of the feature dimensions of the multi-modal data is associated with scaling factor value 1008-C. It can be appreciated that feature dimensions of the multi-modal data that are more relevant to the medical condition are associated with higher scaling factor values in the reconstruction loss 1000.

The scaling factors in the reconstruction loss encourage the multi-modal data embeddings generated by the encoder neural network to efficiently represent information relevant to the medical condition, thus increasing the relevance of the embeddings to the medical condition. The scaling factors in the reconstruction loss can thus enable the patient clustering system (described with reference to FIG. 5) to determine patient categories that are more relevant to the medical condition. The scaling factors in the reconstruction loss can thereby increase the utility and accuracy of predictions and clinical decisions based on classifying patients into patient categories (as described with reference to FIG. 8).

In some implementations, rather than using the reconstruction loss 1000 described above, the training system 900 can implement a reconstruction loss 1000 without scaling factors, e.g., a reconstruction loss that measures reconstruction errors uniformly across each feature dimension of the multi-modal data. For example, the training system 900 can use a reconstruction loss 1000 that measures the error between: (i) reconstructed multi-modal data, and (ii) input multi-modal data, using an $L_1$ similarity measure, an $L_2$ similarity measure, or any other appropriate similarity measure.

The archetype loss 1100 is defined with reference to one or more "target" multi-modal data archetypes. Each target multi-modal data archetype represents multi-modal data of the same form (i.e., having the same feature dimensions) as that provided as an input to the encoder neural network 104 and generated as an output by the decoder neural network 108. Each target multi-modal data archetype is associated with a corresponding dimension of the latent space and represents a target (i.e., desired) output to be generated by the decoder neural network 108 by processing an embedding representing the dimension of the latent space.

Generally, each dimension of the latent space can be represented by a basis embedding from a set of basis embeddings in the latent space that provide a basis of the latent space, as described above with reference to FIG. 3. For instance, the set of basis embeddings can be given by the set of unit embeddings in the latent space, where a unit embedding refers to an embedding where one position in the embedding has value 1 and the other positions in the embedding have value 0.

For convenience, a dimension of the latent space that is associated with a corresponding target multi-modal data archetype is sometimes referred to as an "anchored" dimension of the latent space. Generally, only a proper subset of the dimensions of the latent space are anchored dimensions.

To evaluate the archetype loss 1100, the training engine 910 generates, for each anchored dimension of the latent space, a "predicted" multi-modal data archetype for the anchored dimension by processing an embedding representing the anchored dimension using the decoder neural network 108. The archetype loss 1100 then measures, for each anchored dimension of the latent space, an error between: (i) the target multi-modal data archetype for the anchored dimension, and (ii) the predicted multi-modal data archetype for the anchored dimension.

Optionally, to evaluate the archetype loss 1100, the training engine 910 can further process the respective target multi-modal data archetype for each anchored dimension of the latent space to generate an embedding of the target multi-modal data archetype. The archetype loss then also measures, for each anchored dimension of the latent space, an error between: (i) a basis embedding (e.g., unit embedding) representing the anchored dimension of the latent space, and (ii) the embedding of the target multi-modal data archetype for the anchored dimension.

For example, the archetype loss $\mathcal{L}_a$ can have the form:

$$\mathcal{L}_a = \sum_{d=1}^{D} \alpha_i \cdot \mathcal{L}_a^D(d) + \beta_i \cdot \mathcal{L}_a^E(d) \tag{12}$$

where d indexes the anchored dimensions of the latent space, D is the number of anchored dimensions in the latent space, $(\alpha_i)_{i=1}^D$ and $(\beta_i)_{i=1}^D$ are scalar coefficients, $\mathcal{L}_a^D(d)$ denotes the error between: (i) the target multi-modal data archetype for anchored dimension d, and (ii) the predicted multi-modal data archetype for anchored dimension d, and $\mathcal{L}_a^E(d)$ denotes the error between: (i) the embedding of the target multi-modal data archetype for anchored dimension d, and (ii) the basis embedding (e.g., unit embedding) representing anchored dimension d in the latent space. In some cases, the $(\alpha_i)_{i=1}^D$ coefficients all have value zero and the $(\beta_i)_{i=1}^D$ coefficients all have non-zero values. In other cases, the $(\beta_i)_{i=1}^D$ coefficients all have value zero and $(\alpha_i)_{i=1}^D$ coefficients all have non-zero values. In other cases, one or more of the $(\alpha_i)_{i=1}^D$ coefficients have non-zero values and one or more of the $(\beta_i)_{i=1}^D$ coefficients have non-zero values.

The training engine 910 can measure the error between a target multi-modal data archetype and a predicted multi-modal data archetype in any appropriate way. A few example techniques for measuring the error between a target multi-modal data archetype and a predicted multi-modal data archetype are described next.

In some implementations, the training engine 910 can measure the error between a target multi-modal data archetype and a predicted multi-modal data archetype using an error measure that is analogous to the reconstruction loss described above, e.g., with reference to equation (11). That is, the predicted multi-modal data archetype can be understood as a "reconstruction" of the target multi-modal data archetype, and the training engine 910 can measure the error between the target multi-modal data archetype and the predicted multi-modal data archetype using the reconstruction loss described above. More specifically, the error measure can include multiple scaling factors that each scale a respective term in the error measure that measures an error between the target multi-modal data archetype and the predicted multi-modal data archetype along a proper subset of the multi-modal feature dimensions. The value of each scaling factor in the error measure can be set based on a relevance of the corresponding proper subset of the feature dimensions to a particular medical condition, as described above.

For example, training engine 910 can measure the error E(T, P) between a target multi-modal data archetype T and a predicted multi-modal data archetype P as:

$$E(T, P) = \sum_{i=1}^{n} \beta_i \cdot E(T_{A_i}, P_{A_i}) \tag{13}$$

where for each i∈ {1, . . . , n}: $A_i$ designates a respective proper subset of the feature dimensions of the multi-modal data, $\beta_i$ is a scaling factor corresponding to the proper subset $A_i$ of the multi-modal feature dimensions, and $E(T_{A_i}, P_{A_i})$ measures an error between: (i) the proper subset $A_i$ of the feature dimensions in the target multi-modal data archetype T, and (ii) the proper subset $A_i$ of the feature dimensions in the predicted multi-modal data archetype P. The error $E(T_{A_i}, P_{A_i})$ between can be measured, e.g., using an $L_1$ similarity measure, an $L_2$ similarity measure, a cosine similarity measure, or any other appropriate measure. Generally, the scaling factors $(\beta_i)_{i=1}^4$ each have different values.

In some implementations, the training system 900 can measure the error between a target multi-modal data archetype and a predicted multi-modal data archetype using an error measure without scaling factors. For example, the training system 900 can measure the error between a target multi-modal data archetype and a predicted multi-modal data archetype using an $L_1$ similarity measure, $L_2$ similarity measure, cosine similarity measure, or any other appropriate similarity measure.

The training engine 910 can measure the error between: (i) an embedding of a target multi-modal data archetype for an anchored dimension, and (ii) a basis embedding representing the anchored dimension, in any appropriate way, e.g., as an $L_2$ error.

The anchored dimensions of the latent space and the target archetypes for the anchored dimensions, can be determined in a variety of possible ways. A few example techniques for determining the anchored dimensions of the latent space and the target archetypes for the anchored dimensions are described next.

In some implementations, the training system 900 can initially train the encoder neural network 104 and the decoder neural network 108 for a predefined number of training iterations using an objective function 912 that does not include the archetype loss 1100. The training system 900 can then generate a respective multi-modal data archetype corresponding to each dimension of the latent space, i.e., by processing a respective embedding representing each dimension of the latent space using the decoder neural network 108. The training system 900 can optionally generate an archetype representation for each generated multi-modal data archetype, as described with reference to FIG. 3.

The training system 900 can provide the multi-modal data archetypes (and, optionally, the archetype representations) to a user, e.g., through a user interface on a user device. The user can provide an input, e.g., through the user interface on the user device, indicating that one or more of the multi-modal data archetypes should be designated as target multi-modal data archetypes (and, by extension, that the corresponding dimensions of the latent space should be anchored dimensions). The training system 900 can then resume training of the encoder neural network 104 and the decoder neural network 108 using an objective function 912 that includes an archetype loss 1100 corresponding to the target multi-modal data archetypes specified by the user.

Thus the first stage of training, i.e., without the archetype loss 1100, can be used to generate a set of "candidate" multi-modal data archetypes from which a user can select (e.g., by way of a user interface on a user device) target multi-modal data archetypes for use in the second stage of training, i.e., with the archetype loss 1100.

In some implementations, a user can directly specify (e.g., through a user interface on a user device) one or more target multi-modal data archetypes, e.g., from a predefined set of multi-modal data archetypes.

Generally, a user can select target multi-modal data archetypes using any appropriate criteria, and selecting target multi-modal data archetypes enables a user to control how the encoder neural network represents multi-modal data in the latent space. This provides a significant advantage over training paradigms that treat the encoder and decoder neural networks as uninterpretable "black boxes" that can a user can control only indirectly, e.g., through the choice of training data.

Moreover, users can select target multi-modal data archetypes that represent clinically meaningful patterns in multi-modal data characterizing patients. In particular, users can select target multi-modal data archetypes that are relevant to a particular medical condition, e.g., that include multi-modal features that typically co-occur in patients having the medical condition. Thus the archetype loss can encourage the multi-modal data embeddings generated by the encoder neural network to efficiently represent information relevant to the medical condition. The archetype loss can thus enable the patient clustering system (described with reference to FIG. 5) to determine patient categories that are more relevant to the medical condition. The archetype loss can thereby increase the utility and accuracy of predictions and clinical decisions based on classifying patients into patient categories (as described with reference to FIG. 8).

Figure 11:
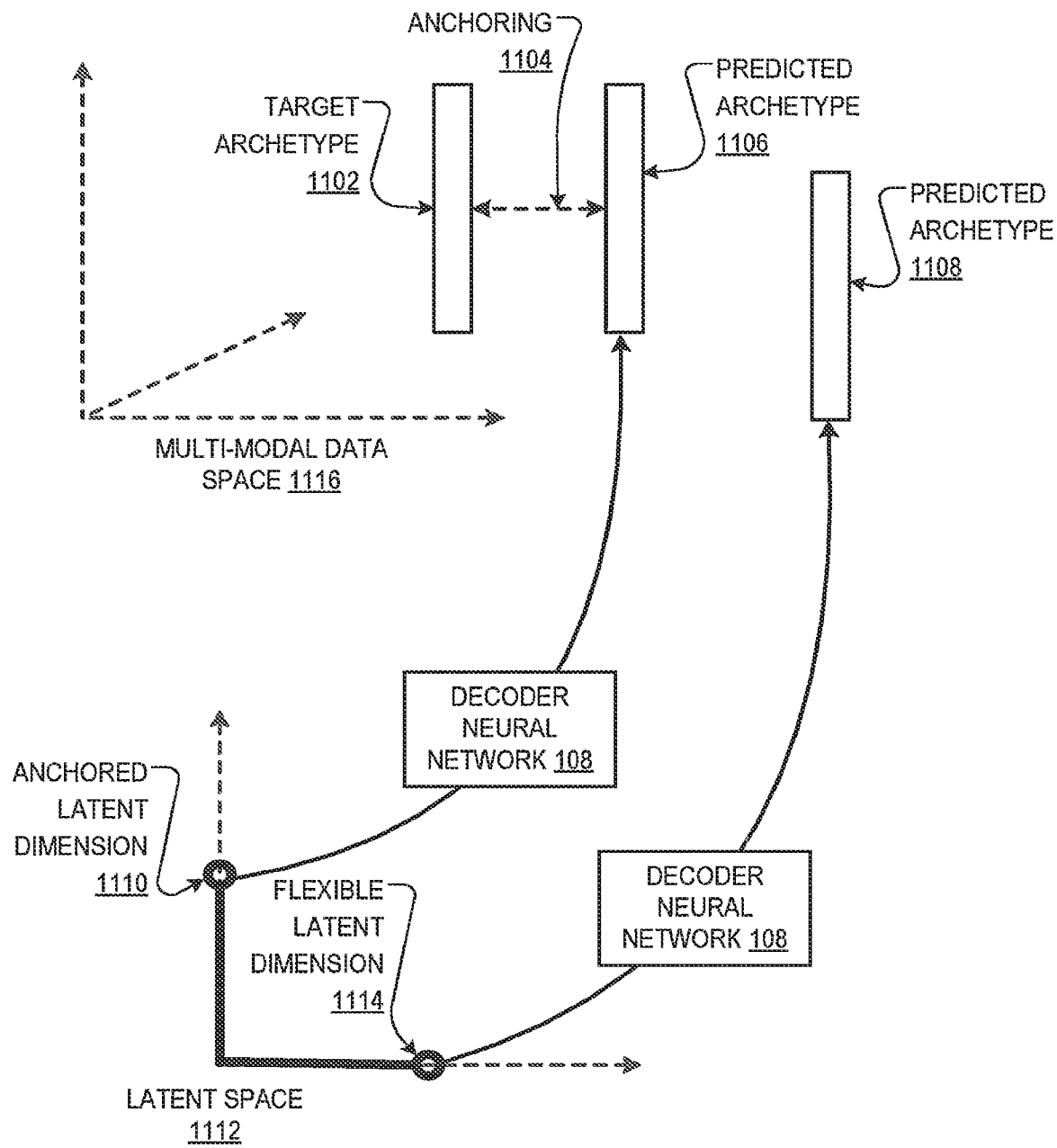
FIG. 11 illustrates an example of an archetype loss.

FIG. 11 illustrates an example of an archetype loss 1100. In this example, the latent space 1112 includes one "anchored" latent dimension 1110, i.e., that is associated with a target multi-modal data archetype 1102 in the multi-modal data space 1116, and one "flexible" (i.e. unanchored) latent dimension 1114, i.e., that is not associated with a target multi-modal data archetype. The decoder neural network 108 maps the anchored latent dimension 1110 to the predicted multi-modal data archetype 1106, and the decoder neural network 108 maps the flexible latent dimension 1114 to the predicted multi-modal data archetype 1108.

During training, the parameter values of the decoder neural network 108 are iteratively adjusted, which causes the predicted archetypes corresponding to the latent dimensions of the latent space to iteratively change over the course of training. The archetype loss 1100 "anchors" 1104 the predicted archetype 1106 to the target archetype 1102, i.e., by penalizing deviations of the predicted archetype 1106 for the anchored latent dimension 1110 from the corresponding target archetype 1102. In contrast, the archetype loss 1100 does not anchor predicted archetype 1108 corresponding to the flexible dimension of the latent space, instead allowing its position in the multi-modal data space 1116 to vary flexibly over the course of training.

The clustering loss 914 at a training iteration is computed based on a clustering, in the latent space, of the embeddings 906 of the multi-modal data 904 from the training examples in the current batch of training examples. The clustering loss 914 can encourage the embeddings 906 to separate into clusters in the latent space, and can reduce any dependence of the clusters on "confounding" features, e.g., features that are designated as being substantially irrelevant, e.g., to a medical condition or to a treatment for a medical condition. The clustering loss 914 can be generated by a cluster hardening system, as will be described in more detail with reference to FIG. 12.

The prior loss 916 measures, for each training example, an error between: (i) the posterior probability distribution over the latent space generated by the encoder neural network 104 for the training example, and (ii) a predefined "prior" probability distribution over the latent space. The prior probability distribution can be, e.g., a standard Normal probability distribution, i.e., with a mean vector of zeros and a covariance matrix given by the identity matrix. The training engine 910 can measure the error between the posterior probability distribution and the prior probability distribution, e.g., using a Kullback-Leibler divergence measure.

Figure 12:
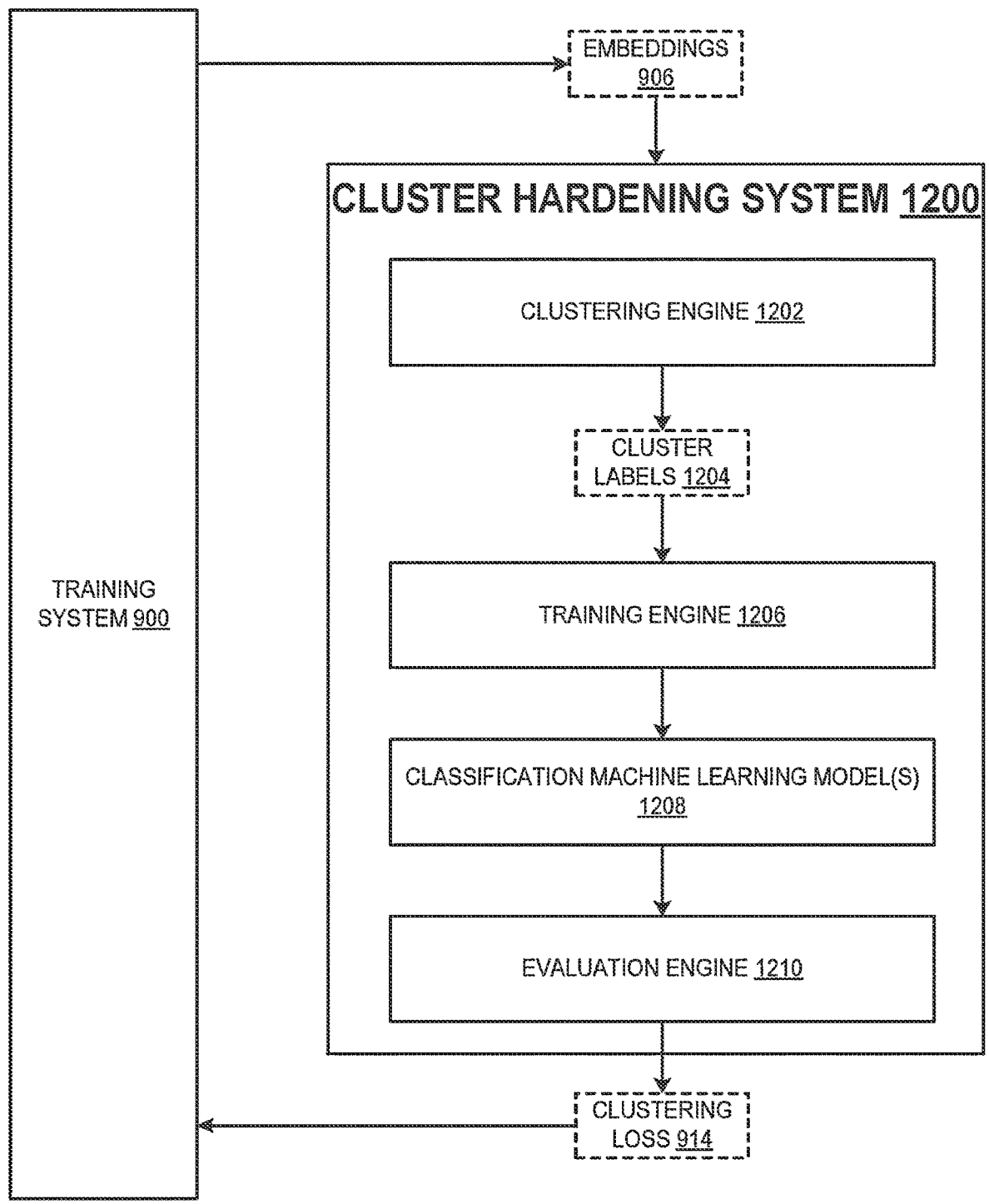
FIG. 12 shows an example cluster hardening system.

FIG. 12 shows an example cluster hardening system 1200. The cluster hardening system 1200 is an example of a system implemented as computer programs on one or more computers in one or more locations in which the systems, components, and techniques described below are implemented.

The cluster hardening system 1200 operates in conjunction with the training system 900, described in more detail with reference to FIG. 9, that jointly trains an encoder neural network and a decoder neural network. The encoder neural network is configured to process multi-modal data characterizing a subject to generate an embedding of the multi-modal data in a latent space. The decoder neural network is configured to process the embedding of the multi-modal data in the latent space to generate a reconstruction of the original multi-modal data.

The training system 900 can jointly train the encoder neural network and the decoder neural network over multiple training iterations to optimize an objective function. The objective function can include a variety of terms, e.g., a reconstruction loss, an archetype loss, and a prior loss, which are each described in more detail with reference to FIG. 9. In particular, at one or more training iterations, the objective function can include a "clustering loss" 914, which will be described in more detail next.

The cluster hardening system 1200 can generate the clustering loss 914 at one or more training iterations during the joint training of the encoder neural network and the decoder neural network by the training system 900. The training system 900 receives the clustering loss 914 from the cluster hardening system 1200, and includes the clustering loss 914 as a term in the objective function, e.g., as described above with reference to equation (10).

At each training iteration, the training system 900 samples a current batch (set) of training examples (e.g., from a pool of training examples), where each training example corresponds to a respective subject and includes multi-modal data that characterizes the subject. The training system 900 then processes the multi-modal data from each training example using the encoder neural network to generate a respective embedding 906 of the multi-modal data from each training example in the latent space. That is, the training system 900 generates a set of embeddings 906, including a respective embedding 906 corresponding to each training example in the current batch of training examples.

The cluster hardening system 1200 is configured to receive a set of embeddings 906 generated by the training system 900 at a training iteration, and to process the set of embeddings 906 to generate a clustering loss 914 for the training iteration. The cluster hardening system 1200 includes a clustering engine 1202, a training engine 1206, one or more classification machine learning models 1208, and an evaluation engine 1210, which are each described in more detail next.

Figure 13:
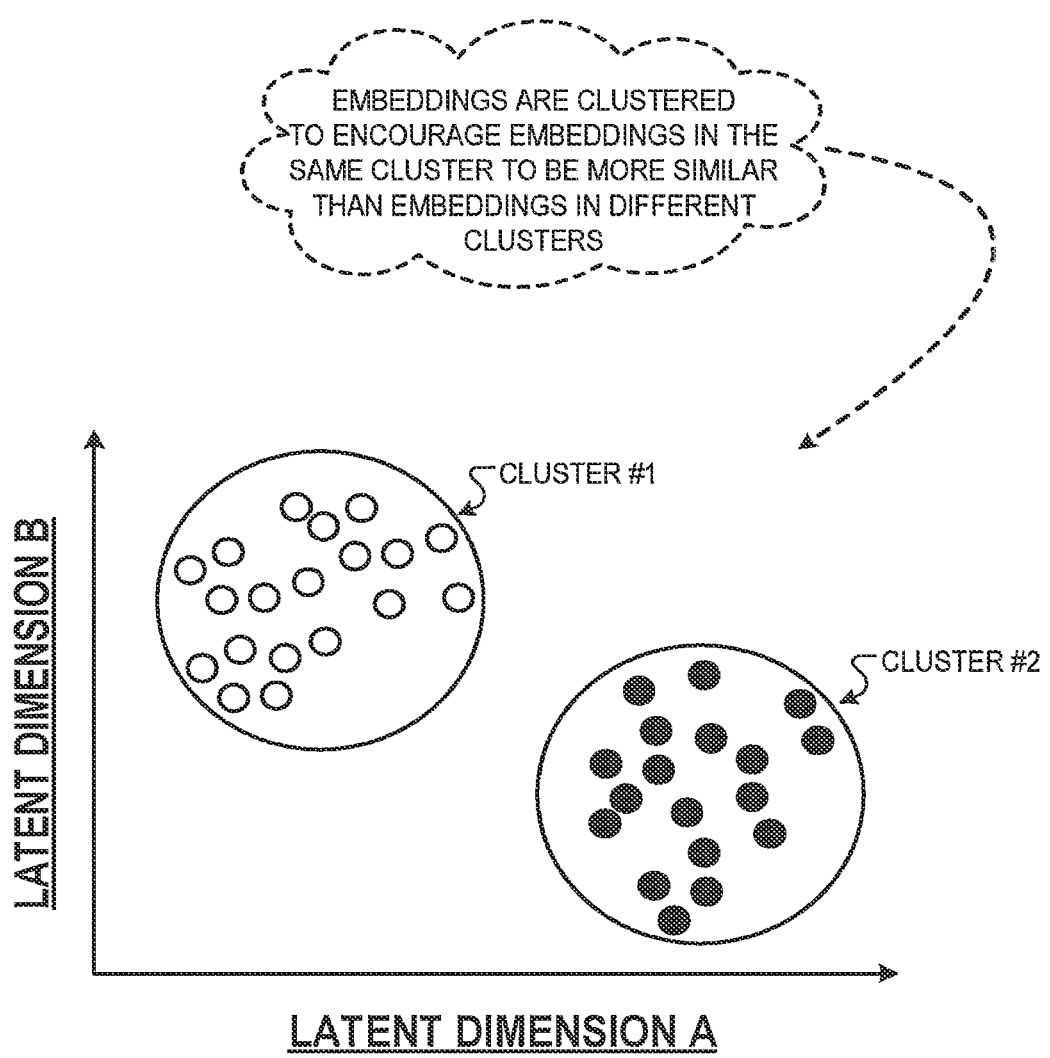
FIG. 13 provides a visual illustration of applying a clustering operation to a set of embeddings.

The clustering engine 1202 receives the set of embeddings 906, and applies a clustering operation to the set of embeddings 906 to generate a partition of the set of embeddings 906 into multiple groups, referred to as "clusters," that each include multiple embeddings 906. Generally, the clustering operation partitions the set of embeddings into clusters such that embeddings in the same cluster tend to be more similar (accordingly to a similarity measure in the latent space) than embeddings in different clusters. FIG. 13, which will be described in more detail below, provides a visual illustration of applying a clustering operation to a set of embeddings.

As a result of the clustering, each embedding 906 is designated as belonging to a respective cluster in a set of clusters. Thus each embedding 906 can understood as being associated with a "cluster label" 1204 that identifies the respective cluster that includes the embedding.

The clustering engine 1202 can cluster the set of embeddings 906 using any appropriate clustering operation, e.g., a k-means clustering operation, an expectation maximization clustering operation, a hierarchical agglomerative clustering operation, or a spectral clustering operation. The numbers of clusters generated by the clustering engine 1202 can be, e.g., a predefined hyper-parameter, or determined dynamically by the clustering engine 1202 during clustering.

The training engine 1206 trains one or more classification machine learning models 1208 using the cluster labels 1204 associated with the embeddings 906. A few example techniques by which the training engine 1206 can train a classification machine learning model 1208 are described next.

In some implementations, the training engine 1206 trains a classification machine learning model 1208 to process an embedding 906 to generate a classification output that predicts the cluster label 1204 of the embedding 906. For example, the classification output can include a respective score for each cluster label that defines a likelihood that the embedding is associated with the cluster label. For convenience, a classification machine learning model 1208 that is trained to process an embedding 906 to predict the cluster label 1204 of the embedding 906 may be referred to herein as a "cluster classification model."

In some implementations, the training engine 1206 trains a classification machine learning model 1208 to process a set of "confounding" features associated with a subject to generate a classification output that predicts the cluster label 1204 of the embedding 906 of the multi-modal data characterizing the subject. A confounding feature can refer to a feature that has been designated as being substantially irrelevant, e.g., to a medical condition, or to a treatment for a medical condition. That is, confounding features measure variation between subjects that, for the purpose of generating predictions related to a medical condition or a treatment to a medical condition, represent "noise" rather than features representing biological characteristics relevant to the predictions. For convenience, a classification machine learning model 1208 that is trained to process a set of confounding features associated with a subject to predict the cluster label 1204 of the embedding 906 of the multi-modal data characterizing the subject may be referred to herein as an "adversarial classification model."

A few examples of possible confounding features are described next.

In one example, multi-modal data characterizing a subject includes sensor data captured by a sensor, and the set of confounding features associated with the subject can include one or more features of the sensor. For example, the sensor can be a medical imaging sensor, e.g., a magnetic resonance imaging (MRI) machine or a computed tomography (CT) machine, and the confounding features can characterize the manufacturer of the medical imaging sensor, hardware included in the medical imaging sensor, software included in the medical imaging sensor, or calibration parameters of the medical imaging sensor.

In another example, the set of confounding features associated with a subject can include one or more features characterizing an acquisition protocol used to acquire parts of the multi-modal data characterizing the subject. For example, the multi-modal data can include genomic data, and the confounding features can characterize the acquisition protocol used to generate the genomic data, e.g., a number of chimeric reads, an average length of a read, a number of reads mapped to multiple loci, a fraction of reads aligning to the mitochondrial genome, area under coverage for all alignments, or a combination thereof.

In another example, the set of confounding features associated with a subject can include one or more of: an education level of the subject, a home address of the subject, identities of physicians that previously interacted with the subject, an employment history of the subject, a familial history of the subject (e.g., characterizing medical history, or relationship history, or both), a medical history of the subject, or a combination thereof.

It can be appreciated that the examples of possible confounding features provided above are not exhaustive, and that the selection of appropriate confounding features may depend on the context of a particular application, e.g., on a particular medical condition or treatment of interest. The designation of certain features as confounding features may be specified, e.g., by a user of the training system 900. Generally, the set of confounding features associated with a subject are not included in the set of multi-modal data characterizing the subject, i.e., that is processed by the encoder neural network to generate the embedding 906 corresponding to the subject.

In some implementations, the training engine 1206 trains both: (i) a cluster classification model (i.e., that processes embeddings 906), and (ii) an adversarial classification model (i.e., that processes confounding features).

As part of training a classification machine learning model 1208, the training engine 1206 can partition the set of embeddings 906 into: (i) a set of "training" embeddings, and (ii) a set of "validation" embeddings. The training engine 1206 trains the classification machine learning model 1208 to predict the cluster labels associated with the training embeddings, but refrains from the training the classification machine learning model 1208 to predict the cluster labels associated with the validation embeddings. That is, the validation embeddings and their associated cluster labels are "held out" from the training of the classification machine learning model 1208.

The training engine 1206 can partition the set of embeddings 906 into a set of training embeddings and a set of validation embeddings in any appropriate way. For example, the training engine 1206 can randomly select a predefined fraction (e.g., 90%, or any other appropriate fraction) of the embeddings in the set of embeddings as training embeddings, and designate the remaining embeddings as being validation embeddings.

Each classification machine learning model 1208 can be any appropriate type of machine learning model, e.g., a neural network model, a random forest model, or a support vector machine model, and can have any appropriate machine learning model architecture. For example, in implementations where a classification machine learning model is a neural network model, the neural network model can include any appropriate types of neural network layers (e.g., fully connected layers, convolutional layers, or attention layers) in any appropriate numbers (e.g., 2 layers, 5 layers, or 10 layers) and connected in any appropriate configuration (e.g., as a linear sequence of layers).

The training engine 1206 can train each classification machine learning model 1208, using any appropriate machine learning training technique, to optimize a classification loss. For example, if a classification machine learning model 1208 is implemented as a neural network model, then the training engine 1206 can train the classification machine learning model 1208 using a stochastic gradient descent training technique. The classification loss measures an accuracy of the classification outputs generated by a classification machine learning model, e.g., the classification loss can be a cross-entropy loss.

After the training engine 1206 trains each classification machine learning model 1208, the evaluation engine 1210 measures the respective classification accuracy of each classification machine learning model 1208, and determines the clustering loss 914 based on the respective classification accuracies of the classification machine learning models 1208.

More specifically, the evaluation engine 1210 can measure the classification accuracy of a classification machine learning model 1208 with reference to the cluster labels associated with the embeddings 906 designated as validation embeddings (as described above). The evaluation engine 1210 generally excludes the cluster labels associated with the embeddings designated as training embeddings from the evaluation of the classification accuracy of the classification machine learning model 1208.

To measure the classification accuracy of a classification machine learning model 1208 on the validation embeddings, the evaluation engine 1210 uses the classification machine learning model to generate a respective classification output for each validation embedding that defines a prediction for the cluster label of the validation embedding. For example, if the classification machine learning model 1208 is a cluster classification model, then the evaluation engine 1210 processes each respective validation embedding to generate a respective classification output for the validation embedding. As another example, if the classification machine learning model 1208 is an adversarial classification model, then the evaluation engine 1210 processes a respective set of confounding features corresponding to each validation embedding to generate a respective classification output for the validation embedding.

After generating a classification output for each validation embedding, the evaluation engine 1210 can measure a respective classification error (e.g., cross-entropy error) between: (i) the classification output, and (ii) the cluster label, for each validation embedding. The evaluation engine 1210 can then determine the overall classification error for the classification machine learning model 1208 based on the respective classification error of the classification machine learning model 1208 for each validation embedding. For example, the evaluation engine 1210 can determine the overall classification error for the classification machine learning model as a measure of central tendency (e.g., a mean, median, or mode) of the classification errors of the classification machine learning model 1208 for the validation embeddings.

The evaluation engine 1210 can determine the clustering loss 914 based on (e.g., as a function of) the respective overall classification error of each classification machine learning model 1208. For example, the evaluation engine 1210 can define the clustering loss 914 as:

$$\mathcal{L}_c = \gamma_1 \cdot \mathcal{L}_{cluster} - \gamma_2 \cdot \mathcal{L}_{adversarial} \quad (14)$$

where $\mathcal{L}_{cluster}$ denotes the overall classification error of the cluster classifier model, $\mathcal{L}_{adversarial}$ denotes the overall classification error of the adversarial classifier model, and $(\gamma_i)_{i=1}^2$ are positive scalar weighting factors. In some cases, the clustering loss 914 includes only the overall classification error of the cluster classifier model and excludes the overall classification error of the adversarial classification model (i.e., such that $\gamma_1 > 0$ and $\gamma_2 = 0$). In some cases, the clustering loss 914 includes only the overall classification error of the adversarial classifier model and excludes the overall classifier error of the cluster classification model (i.e., such that $\gamma_1 = 0$ and $\gamma_2 > 0$).

Figure 14:
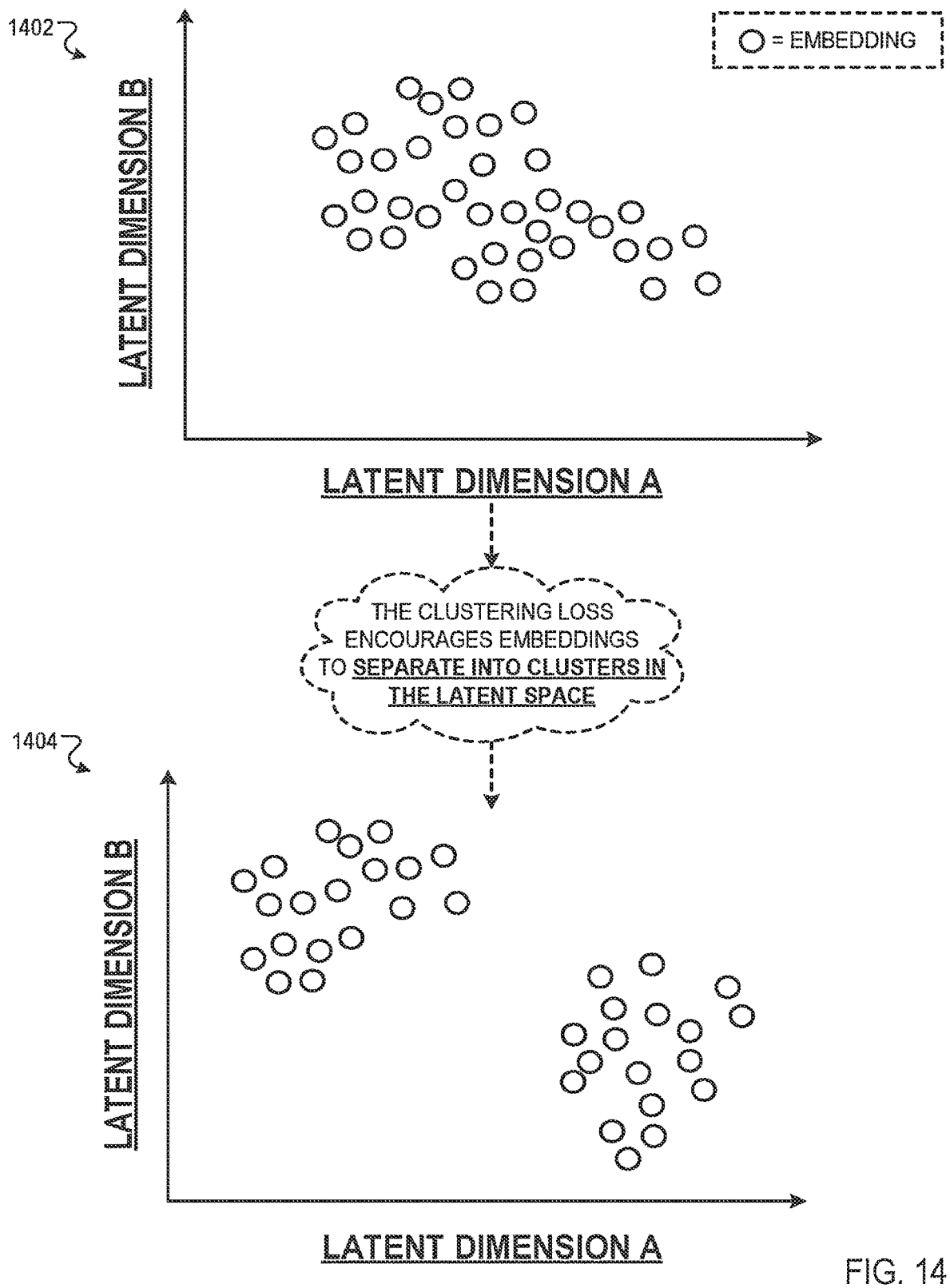
FIG. 14 provides a visual illustration of the clustering loss encouraging embeddings to separate into clusters in the latent space.

In some implementations, the clustering loss 914 is based at least in part on the overall classification error of the cluster classifier model. In these implementations, optimizing the clustering loss 914, e.g., as part of optimizing the objective function used to jointly train the encoder and decoder neural networks, encourages an increase in the overall classification accuracy of the cluster classification model. The overall classification accuracy of the cluster classification model would be enhanced if the embeddings are distributed in clusters (i.e., spatially separated groupings of embeddings) in the latent space, e.g., as opposed to being uniformly distributed through the latent space. Thus, optimizing the clustering loss 914 encourages the embeddings 906 to separate into clusters in the latent space. FIG. 14, which will be described in more detail below, provides a visual illustration of the clustering loss encouraging the embeddings 906 to separate into clusters in the latent space.

By encouraging the embeddings 906 to separate into clusters in the latent space, the clustering loss 914 can increase the likelihood that embeddings in the latent space can be unambiguously assigned to corresponding clusters of embeddings. In particular, the clustering loss 914 can encourage greater similarity between embeddings in the same cluster, and greater difference between embeddings in different clusters.

The patient classification system, described with reference to FIG. 7A, can define each cluster as a patient category, where a subject is included in a patient category if an embedding of multi-modal data characterizing the subject is included in a cluster representing the patient category. In particular, the patient classification system can generate predictions for a subject (e.g., for whether the subject has a medical condition, or will respond to a treatment for a medical condition) based on the patient category of the subject. Thus by encouraging embeddings to separate into clusters in the latent space, the clustering loss 914 can enable the patent classification system to unambiguously assign a patient to a corresponding patient category and generate predictions characterizing the subject (i.e., based on the patient category of the subject) with higher accuracy.

In some implementations, the clustering loss 914 is based at least in part on the overall classification error of the adversarial classifier model. In these implementations, optimizing the clustering loss 914, e.g., as part of optimizing the objective function used to jointly train the encoder and decoder neural networks, encourages a decrease in the overall classification accuracy of the adversarial classification model. For example, with reference to equation (14), the overall classification error of the adversarial classification model ($\mathcal{L}_{adversarial}$) may be scaled by a negative factor in the clustering loss ($-\gamma_2$), such that minimizing the clustering loss encourages maximizing the overall classification error of the adversarial classifier model.

Figure 15:
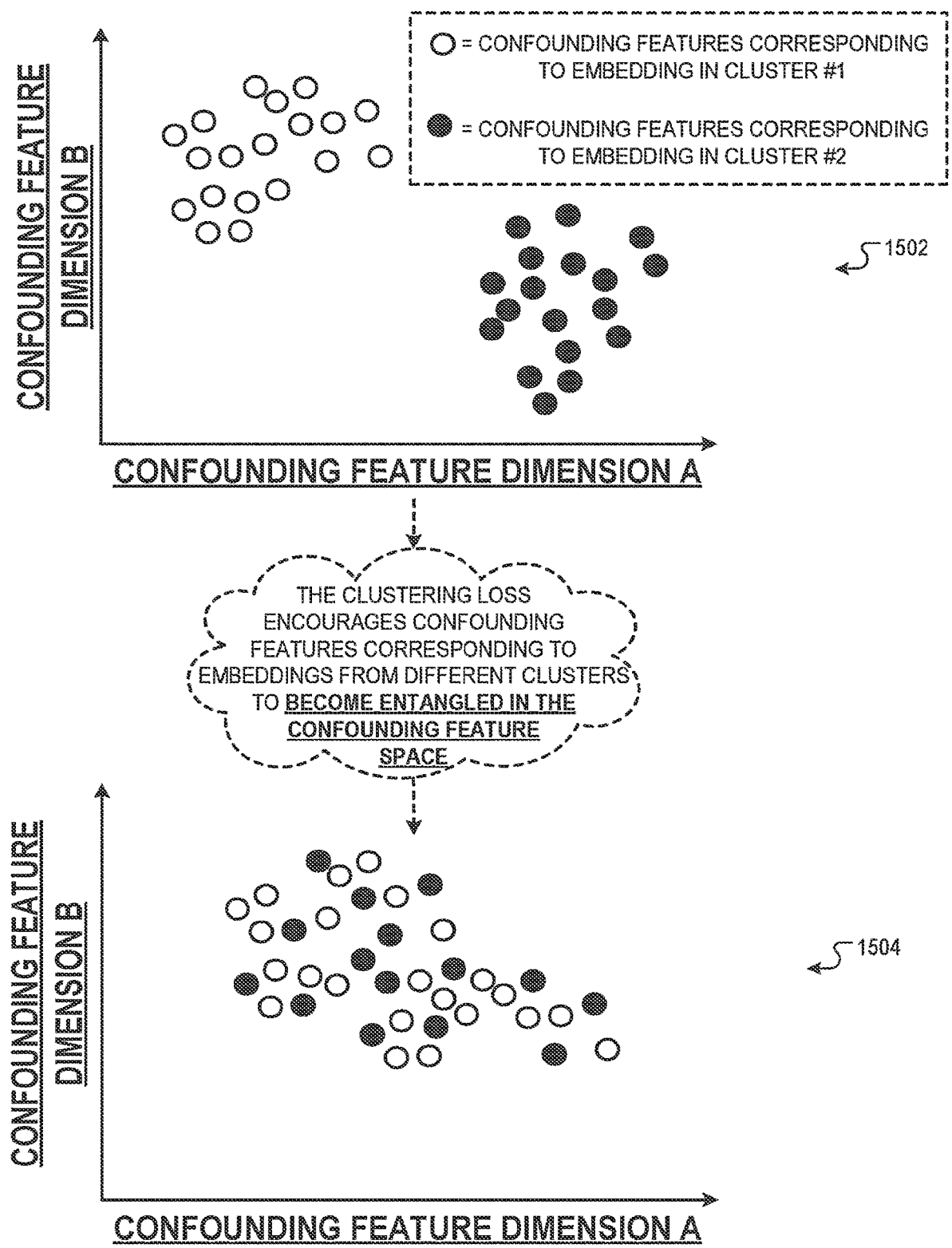
FIG. 15 provides a visual illustration of the clustering loss encouraging confounding features corresponding to embeddings with different cluster labels to become more entangled in the confounding feature space.

Thus, optimizing the clustering loss 914 can encourage confounding features corresponding to embeddings with different cluster labels to become more "entangled" in the confounding feature space. That is, optimizing the clustering loss 914 can encourage an increase in the similarity, measured in the confounding feature space, between confounding features corresponding to embeddings with different cluster labels relative to confounding features corresponding to embeddings with the same cluster label. FIG. 15, which will be described in more detail below, provides a visual illustration of the clustering loss encouraging confounding features corresponding to embeddings 906 with different cluster labels with become more entangled in the confounding feature space.

By encouraging confounding features corresponding to embeddings 906 with different cluster labels 1204 to become entangled in the confounding feature space, the clustering loss 914 can increase the relevance of the clusters, e.g., to a medical condition or to a treatment for a medical condition. In particular, confounding features are, are described above, features that have been designated as being substantially irrelevant, e.g., to a medical condition or to a treatment for a medical condition. Therefore causing confounding features corresponding to embeddings 906 with different cluster labels 1204 to become entangled in the confounding feature space can reduce any dependence of the clusters on the confounding features. In particular, increased entanglement in the confounding feature space reduces the likelihood that clusters in the latent space can be delineated or distinguished on the basis of confounding features.

In some implementations, a cluster classification model that the cluster hardening system 1200 trains to optimize the clustering loss 914 can be provided for use in classifying new patients into patient categories. For instance, the patient classification system 700, described with reference to FIG. 7A, can use a cluster classification model trained to optimize the clustering loss 914 to implementing the scoring engine 706 for classifying new patients into patient categories.

FIG. 13 provides a visual illustration of applying a clustering operation to a set of embeddings. Each embedding is represented by a circle. Embeddings included in "cluster #1" are shown as light colored circles, and embeddings included in "cluster #2" are shown as dark colored circles. For convenience, the embeddings are shown with reference to two dimensions of the latent space (i.e., "latent dimension A" and "latent dimension B"), but in some cases the latent space includes more than two dimensions. It can be appreciated that embeddings in the same cluster tend to be more similar, in the latent space, than embeddings in different clusters.

FIG. 14 provides a visual illustration of the clustering loss encouraging embeddings to separate into clusters in the latent space. Diagram 1402 shows the distribution of the embeddings in the latent space at a first training iteration, and diagram 1404 shows the distribution of the embeddings in the latent space at a subsequent training iteration. The clustering loss has been included in the objective function being optimized during the joint training of the encoder and decoder neural networks at one or more intervening training iterations between the first training iteration and the subsequent training iteration. Each embedding is represented as a circle. For convenience, the embeddings are shown with reference to two dimensions of the latent space (i.e., "latent dimension A" and "latent dimension B"), but in some cases the latent space includes more than two dimensions. It can be appreciated that the clustering loss encourages the embeddings to separate into clusters in the latent space.

FIG. 15 provides a visual illustration of the clustering loss encouraging confounding features corresponding to embeddings with different cluster labels to become more entangled in the confounding feature space. Diagram 1502 shows the distribution of confounding features corresponds to embeddings at a first training iteration, and diagram 1504 shows the distribution of confounding features corresponding to embeddings at a subsequent training iteration. The clustering loss has been included in the objective function being optimized during the joint training of the encoder and decoder neural networks at one or more intervening training iterations between the first training iteration and the subsequent training iteration.

Confounding features corresponding to embeddings in a first cluster are shown as light colored circles, and confounding features corresponding to embeddings in a second cluster are shown as dark colored circles. For convenience, the confounding features are shown with reference to two dimensions of the confounding feature space (i.e., dimensions corresponding to "confounding feature dimension A" and "confounding feature dimension B"), but in some cases the confounding feature space in includes more than two dimensions.

It can be appreciated that the clustering loss encourages confounding features corresponding to embeddings in different clusters to become more entangled in the confounding feature space.

Figure 16:
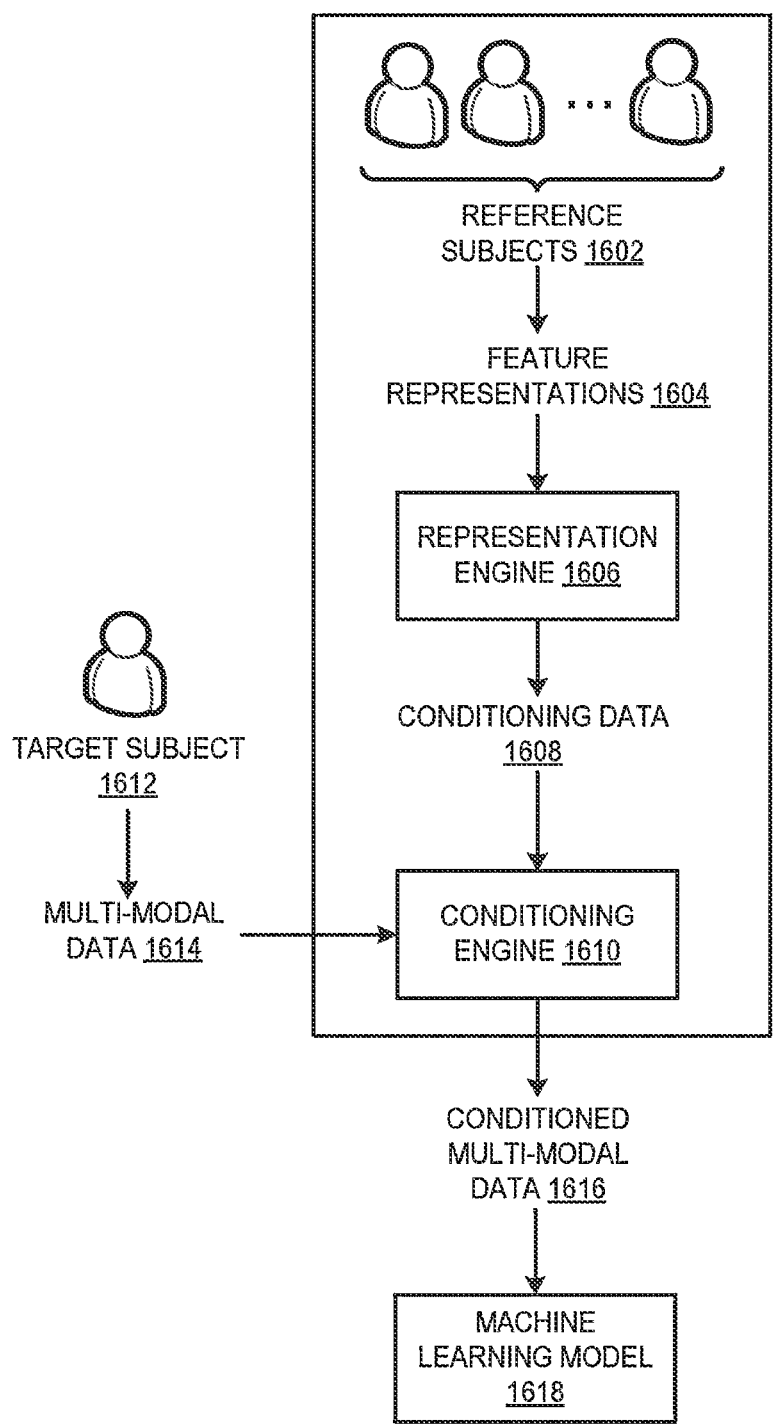
FIG. 16 shows an example conditioning system.

FIG. 16 shows an example conditioning system 1600. The conditioning system 1600 is an example of a system implemented as computer programs on one or more computers in one or more locations in which the systems, components, and techniques described below are implemented.

The conditioning system 1600 is configured to receive multi-modal data 1614 characterizing a "target" subject 1612. The multi-modal data 1614 includes a respective feature representation for each modality in a set of modalities, where a feature representation for a modality refers to a collection of features that collectively represent data from the modality, as described above.

The conditioning system 1600 conditions the multi-modal data 1614 characterizing the target subject 1612 based on conditioning data, derived from a population of "reference" subjects 1602, to generate conditioned multi-modal data 1616. (A "population" of subjects refers to a set of one or more subjects, and can include any appropriate number of subjects, e.g., 10, 100, or 1000 subjects). The conditioning system 1600 thus enriches the multi-modal data 1614 characterizing the target subject 1612 with conditioning data derived from the population of reference subjects 1602, as will be described in more detail below.

Conditioned multi-modal data 1616 generated by the conditioning system 1600 can be used in any of a variety of applications. For example, conditioned multi-modal data 1616 generated by the conditioning system 1600 for a target subject 1612 can be provided as an input to a machine learning model 1618. The machine learning model 1618 can process the conditioned multi-modal data 1616 to generate a machine learning model output characterizing the target subject 1612.

The machine learning model 1618 (i.e., that processes the conditioned multi-modal data 1616) can have any appropriate machine learning model architecture (e.g., a neural network architecture, a random forest architecture, or a support vector machine architecture), and can be configured to generate any appropriate machine learning model output. For example, the machine learning model output can be a prediction characterizing the target subject 1612, e.g., a prediction for whether the target subject 1612 has a particular medical condition, a prediction for whether the target subject 1612 would respond to a particular medical treatment, or a prediction for a prognosis of the target subject

1612. As another example, the machine learning model output can be an embedding representing the target subject 1612.

In particular, the conditioning system 1600 can be used to pre-process multi-modal data provided to the machine learning system 100 described with reference to FIG. 1. For example, the conditioning system 1600 can pre-process multi-modal data used by the training system 900, described with reference to FIG. 9, for training the encoder neural network and the decoder neural network of the machine learning system 100. As another example, the conditioning system 1600 can pre-process multi-modal data characterizing a subject that is processed by the machine learning system 100 to classify the subject as being included in patient category, e.g., as described with reference to FIG. 7A.

Conditioning multi-modal data 1614 characterizing a target subject 1612 prior to processing the multi-modal data 1614 using a machine learning model can enable the machine learning model to operate more effectively. For example, the machine learning model can leverage the enhanced information content of the conditioned multi-modal data 1616 to generate predictions with higher accuracy, or to generate richer feature embeddings characterizing the target subject 1612.

The conditioning system 1600 can condition multi-modal data 1614 characterizing a target subject 1612 based on a population of reference subjects 1602 using a representation engine 1606 and a conditioning engine 1610, which are each described in more detail next.

The representation engine 1606 is configured to obtain one or more feature representations 1604, corresponding to a reference modality, for each reference subject 1602. The reference modality can be any appropriate modality, e.g., an fMRI modality, a PET modality, a genomic data modality, or a proteomic data modality. The representation engine 1606 can obtain the feature representations 1604 of the reference subjects, e.g., by retrieving the feature representations 1604 of the reference subjects 1602 from a data store, e.g., a physical data storage device or a logical data storage area.

In some cases, the conditioning system 1600 obtains, for each reference subject 1602, a "pre-treatment" feature representation of the reference subject 1602 and a "post-treatment" feature representation of the reference subject 1602. The pre-treatment feature representation of the reference subject may have been captured before a medical treatment (e.g., a drug) was administered to the reference subject (e.g., one hour or one day before the medical treatment was administered). The post-treatment feature representation of the reference subject may have been captured after the medical treatment was administered to the reference subject (e.g., one hour or one day after the medical treatment was administered).

The representation engine 1606 processes the feature representations 1604 of the reference subjects 1602 to generate conditioning data 1608, i.e., for use in conditioning the multi-modal data 1614 characterizing the target subject 1612. Generally, the conditioning data 1608 can be represented as an ordered collection of numerical values, e.g., a vector, matrix, or other tensor of numerical values. For convenience, the collection of numerical values representing the conditioning data 1608 can be understood as being organized into a set of feature dimensions.

A few example techniques by which the representation engine 1606 can generate the conditioning data 1608 based on the feature representations 1604 of the reference subjects 1602 are described next.

In some implementations, each feature representation 1604 of each reference subject 1602 has a set of feature dimensions, and the representation engine 1606 generates conditioning data 1608 that includes a respective correlation coefficient for each pair of feature dimensions. The correlation coefficient for a pair of feature dimensions (i, j) can represent a correlation, across the population of reference subjects 1602, between the value of feature dimension i and the value of feature dimension j. The correlation coefficient can be any appropriate correlation coefficient, e.g., a Pearson correlation coefficient, or a Spearman correlation coefficient, or a Kendall correlation coefficient. In these implementations, the conditioning data 1608 can be represented, e.g., as an N×N matrix, where N is the number of feature dimensions in the feature representations 1604 of the reference subjects 1602 and entry (i, j) of the matrix represents the correlation coefficient for the pair of feature dimensions (i, j).

A few examples of generating conditioning data as a collection of correlation coefficients are described next.

In one example, the feature representation 1604 of each reference subject 1602 can include proteomic data that defines, for each protein in a predefined set of proteins, an expression level of the protein in the reference subject 1602. In this example, the representation engine 1606 can generate conditioning data that defines a respective correlation coefficient for each pair of proteins from the set of proteins. The correlation coefficient for a pair of proteins measures a correlation in the expression levels of the pair of proteins across the population of reference subjects 1602.

In another example, the feature representation 1604 of each reference subject can include genomic data that defines, for each gene in a predefined set of genes, an expression level of the gene in the genome of the reference subject 1602. In this example, the representation engine 1606 can generate conditioning data 1608 that defines a respective correlation coefficient for each pair of genes in the set of genes. The correlation coefficient for a pair of genes measures a correlation in the expression levels of the pair of genes across the population of reference subjects 1602.

In some implementations, to generate the conditioning data 1608, the representation engine 1606 computes a "differential" feature representation for each reference subject 1602 as a difference between a post-treatment feature representation and a pre-treatment feature representation of the reference subject 1602. For example, the representation engine 1606 can compute the differential feature representation for each reference subject 1602 by subtracting the pre-treatment feature representation of the reference subject 1602 from the post-treatment feature representation 1604 of the reference subject 1602. The representation engine 1606 can then generate the conditioning data 1608 by combining the differential feature representations of the reference subjects. For example, the representation engine 1606 can compute the value of each feature dimension of the conditioning data as a measure of central tendency of the values of a corresponding feature dimension in the differential feature representations of the reference subjects 1602. The measure of central tendency can be, e.g., a mean, a median, or a mode.

A few examples of generating conditioning data 1608 using pre-treatment and post-treatment feature representations of the reference subjects 1602 are described next.

In one example, for each reference subject 1602, the pre-treatment and the post-treatment feature representations of the reference subject 1602 are derived from PET imaging of the brain of the reference subject 1602.

In particular, the pre-treatment feature representation of the reference subject can be derived from a PET image captured prior to a drug being administered to the reference subject. For example, the pre-treatment feature representation of the reference subject can define, for each brain region in a parcellation of the brain of the reference subject, an average of the intensity values of the voxels in the brain region in the pre-treatment PET image.

The post-treatment feature representation of the reference subject can be derived from a PET image captured after the drug (which is labeled with a tracer element) is administered to the patient. For example, the post-treatment feature representation of the reference subject can define, for each brain region in the parcellation of the brain of the reference subject, an average of the intensity values of the voxels in the brain region of the post-treatment PET image.

In this example, the conditioning data 1608 may represent, for each brain region in the brain parcellation, a measure of penetration by the drug into the brain region across the population of reference subjects. The conditioning data 1608 can be represented, e.g., as an N×1 vector of numerical values, where N is the number of brain regions in the brain parcellation, and the value of each entry i in the vector represents penetration of the drug into brain region i.

In another example, for each reference subject 1602, the pre-treatment and the post-treatment feature representations of the reference subject 1602 are each derived from fMRI imaging of the brain of the reference subject 1602.

In particular, the pre-treatment feature representation of the reference subject can be derived from fMRI imaging of the reference subject 1602 prior to a drug being administered to the reference subject. For example, the pre-treatment feature representation of the reference subject can be a functional connectivity matrix representing correlations between blood flow curves in brain regions of the reference subject prior to the drug being administered.

The post-treatment feature representation of the reference subject can be derived from fMRI imaging of the reference subject after the drug is administered to the reference subject. For example, the post-treatment feature representation can be a functional connectivity matrix representing correlations between blood flow curves in brain regions of the reference subject after the drug is administered.

In this example, the conditioning data 1608 can represent, for each pair of brain regions in a brain parcellation, a measure of change in functional connectivity between the pair of brain regions (i.e., measured across the population of reference patients) as a result of administration of the drug. The conditioning data 1608 can be represented, e.g., as an N×N matrix of numerical values, where N is the number of brain regions in the brain parcellation and the value of each entry (i, j) in the matrix represents a change in the functional connectivity between the pair of brain regions (i, j).

In some implementations, to generate the conditioning data 1608, the representation engine 1606 obtains both: (i) a feature representation, and (ii) a label, for each reference subject 1602. The label can define, e.g., whether the reference subject 1602 has a medical condition, or whether the reference subject responded successfully to a treatment for a medical condition. The label for a reference patient can generally be represented as a numerical value, e.g., a binary 0/1 numerical value. In these implementations, the representation engine 1606 can generate conditioning data 1608 that includes a respective correlation coefficient for each feature dimension in the feature representations 1604 of the reference subjects 1602. The correlation coefficient for a feature dimension can represent a correlation, across the population of reference subjects 1602, between: (i) the value of the feature dimension in the feature representations 1604 of the reference subjects 1602, and (ii) the labels of the reference subjects 1602. The correlation coefficient can be any appropriate correlation coefficient, e.g., a Pearson correlation coefficient, or a Spearman correlation coefficient, or a Kendall correlation coefficient. In these implementations, the conditioning data 1608 can be represented, e.g., as an N×1 vector, where N is the number of feature dimensions in the feature representations 1604 of the reference subjects 1602 and entry i of the vector represents the correlation coefficient for feature dimension i.

Optionally, the conditioning system 1600 can normalize the conditioning data 1608, e.g., by applying a soft-max function or a sigmoid function to the conditioning data 1608.

Generally, the conditioning system 1600 can generate the conditioning data 1608 once, and thereafter maintain the conditioning data 1608 for use in conditioning respective multi-modal data 1614 characterizing any appropriate number of target subjects 1612. That is, the conditioning system 1600 is not required to regenerate the conditioning data 1608 from the feature representations 1604 of the reference subjects 1602 each time the conditioning system 1600 conditions multi-modal data 1614 characterizing a target subject 1612. In particular, after generating the conditioning data 1608, the conditioning system 1600 can store the conditioning data 1608 in a data store, and then retrieve the conditioning data 1608 from the data store each time the conditioning system 1600 conditions multi-modal data 1614 characterizing a target subject 1612.

The conditioning engine 1610 is configured to apply the conditioning data 1608 to the multi-modal data 1614 characterizing the target subject 1612 to generate conditioned multi-modal data 1616. In particular, for each modality in a predefined set of one or more "target" modalities, the conditioning engine 1610 applies the conditioning data 1608 to a set of feature dimensions of the multi-modal data corresponding to the target modality.

The set of target modalities that are conditioned using the conditioning data 1608 can be a proper subset the full set of modalities included in the multi-modal data 1614. Thus, certain feature dimensions of the multi-modal data 1614 may be unaffected by the application of the conditioning data 1608 to the multi-modal data 1614.

In some cases, the conditioning engine 1610 implements a cross-modal conditioning operation by using the conditioning data 1608 to condition target modalities in the multi-modal data 1614 which are different than the reference modality used to generate the conditioning data 1608. For example, as will be described in more detail below, the conditioning engine 1610 can use conditioning data 1608 derived from PET imaging showing penetration of a drug in the brains of the reference subjects to condition fMRI data characterizing the brain of the target subject 1612.

The conditioning engine 1610 can apply the conditioning data 1608 to a set of feature dimensions of the multi-modal data 1614 in any of a variety of possible ways. A few example techniques for applying the conditioning data to a set of feature dimensions of the multi-modal data 1614 are described next.

In some implementations, the conditioning data 1608 can be represented as an N×1 vector, and the conditioning engine 1610 can apply the conditioning data 1608 to a set of N corresponding feature dimensions of the multi-modal data 1614. For example, the conditioning engine can add the conditioning data 1608 to the corresponding feature dimensions of the multi-modal data 1614. As another example, the conditioning engine 1610 can pointwise multiply the conditioning data 1608 by the corresponding feature dimensions of the multi-modal data 1614. A few examples of applying conditioning data 1608 represented as an N×1 vector to a set of N corresponding feature dimensions of the multi-modal data 1614 are described next.

In one example, the conditioning data 1608 can be an N×1 vector of numerical values representing penetration of a drug into each of N brain regions in a brain parcellation. In this example, the conditioning data 1608 can be applied to a set of N feature dimensions of the multi-modal data representing features of the N brain regions in the brain of the target subject 1612. For example, the conditioning data 1608 can be applied to a set of N feature dimensions of the multi-modal data representing activations of the N brain regions measured in the brain of the target subject 1612 by fMRI. (The "activation" of a brain region, as measured by fMRI, can refer to, e.g., an average or a maximum value of an average blood flow curve for the brain region). As another example, the conditioning data 1608 can be applied to a set of N feature dimensions of the multi-modal data representing electrical activity of the N brain regions measured in the brain of the target subject 1612 by EEG probes.

In another example, the conditioning data 1608 can be an N×1 vector of correlation coefficients representing correlations between: (i) values of feature dimensions in the feature representations of the reference subjects 1602, and (ii) labels of the reference subjects. In this example, the N×1 conditioning vector can be pointwise multiplied by N corresponding feature dimensions of the multi-modal data 1614, e.g., N feature dimensions of the multi-modal data corresponding to the same modality as the feature representations 1604 of the reference subjects 1602.

In some implementations, the conditioning data 1608 can be represented as an N×N matrix, and the conditioning engine 1610 can apply the conditioning data 1608 to a set of N or $N^2$ corresponding feature dimensions of the multi-modal data 1614. (The "corresponding feature dimensions of the multi-modal data" refer to, e.g., a set of feature dimensions of the multi-modal data that are designated, by the conditioning system, to be conditioned using the conditioning data). For example, the conditioning engine 1610 can add or pointwise multiply the elements of the N×N conditioning matrix by $N^2$ corresponding feature dimensions of the multi-modal data 1614. As another example, the conditioning engine 1610 can matrix multiply the N×N conditioning matrix by N corresponding feature dimensions of the multi-modal data 1614 (e.g., represented as an N×1 vector) or by $N^2$ corresponding feature dimensions of the multi-modal data 1614 (e.g., represented as an N×N matrix).

More specifically, for example, the conditioning data 1608 can be an N×N matrix, derived from fMRI data characterizing the reference patients, that measures changes in functional connectivity between pairs of brain regions across the population of reference patients as a result of administration of a drug, as described above. In this example, N can represent the number of brain regions in a brain parcellation. The N×N conditioning matrix can be added to, pointwise multiplied by, or matrix multiplied by $N^2$ corresponding feature dimensions of the multi-modal data 1614, e.g., that represent a functional connectivity matrix derived from fMRI imaging of the target subject 1612. The N×N can also be matrix multiplied by N corresponding feature dimensions of the multi-modal data 1614, e.g., that represent activations of the N brain regions measured in the brain of the target subject 1612 by fMRI.

As another example, the conditioning data 1608 can be an N×N matrix of correlation coefficients representing correlations, across the population of reference subjects 1602, between expression levels of proteins in a predefined set of N proteins. In this example, the N×N conditioning matrix can be matrix multiplied by N corresponding feature dimensions of the multi-modal data 1614, e.g., that represent expression levels of each of the N proteins in the target subject 1612.

As another example, the conditioning data 1608 can be an N×N matrix of correlation coefficients representing correlations, measured across the population of reference subjects 1602, between expression levels of genes in a predefined set of N genes. In this example, the N×N conditioning matrix can be matrix multiplied by N corresponding feature dimensions of the multi-modal data 1614, e.g., that represent expression levels of each of the N genes in the genome of the target subject 1612.

The description above references generating conditioning data 1608 derived from feature representations of the reference subjects 1602 corresponding to a particular reference modality. However, it can be appreciated that the conditioning system 1600 can obtain feature representations of the reference subjects 1602 corresponding to each of multiple reference modalities, and generate respective conditioning data 1608 based on each reference modality. The conditioning system 1600 can then condition multi-modal data 1614 characterizing a target subject 1612 using the respective conditioning data 1608 derived from each of the multiple reference modalities.

Figure 17:
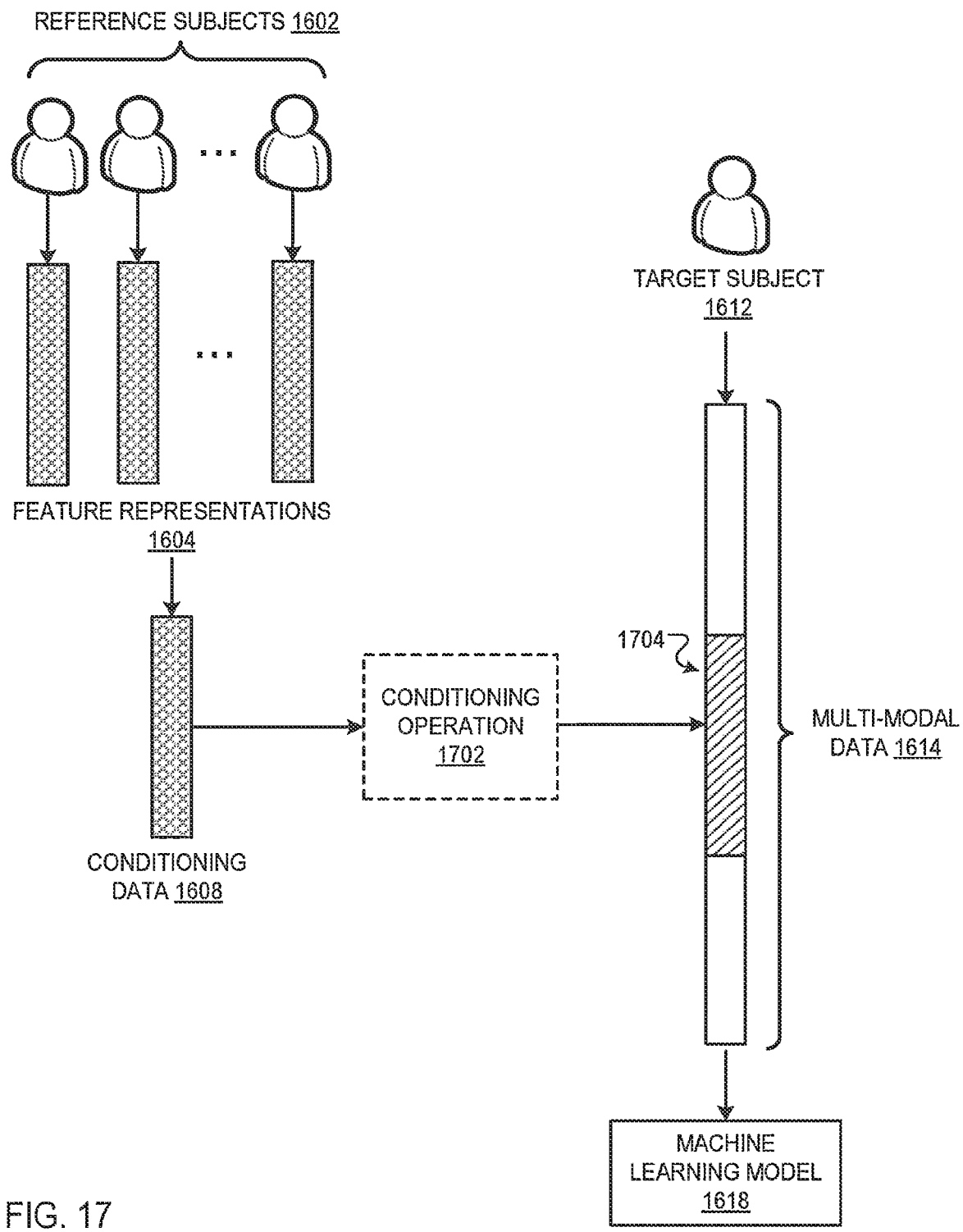
FIG. 17 illustrates an example of operations performed by a conditioning system.

FIG. 17 illustrates an example of the operations performed by the conditioning system 1600 described with reference to FIG. 16. The conditioning system obtains a respective feature representation, corresponding to a reference feature modality, for each reference subject 1602 in a population of reference subjects 1602. The conditioning system 1600 processes the feature representations 1604 of the reference subjects 1602 to generate conditioning data 1608. The conditioning system 1600 applies the conditioning data 1608 to one or more feature dimensions 1704 of a set of multi-modal data 1614 characterizing a target subject 1612 by way of a conditioning operation 1702. The conditioning operation 1702 can be, e.g., an pointwise addition, pointwise multiplication, or matrix multiplication operation. The conditioned multi-modal data 1616 can then be provided as an input to a machine learning model 1618, e.g., the encoder neural network of the machine learning system described with reference to FIG. 1.

Figure 18:
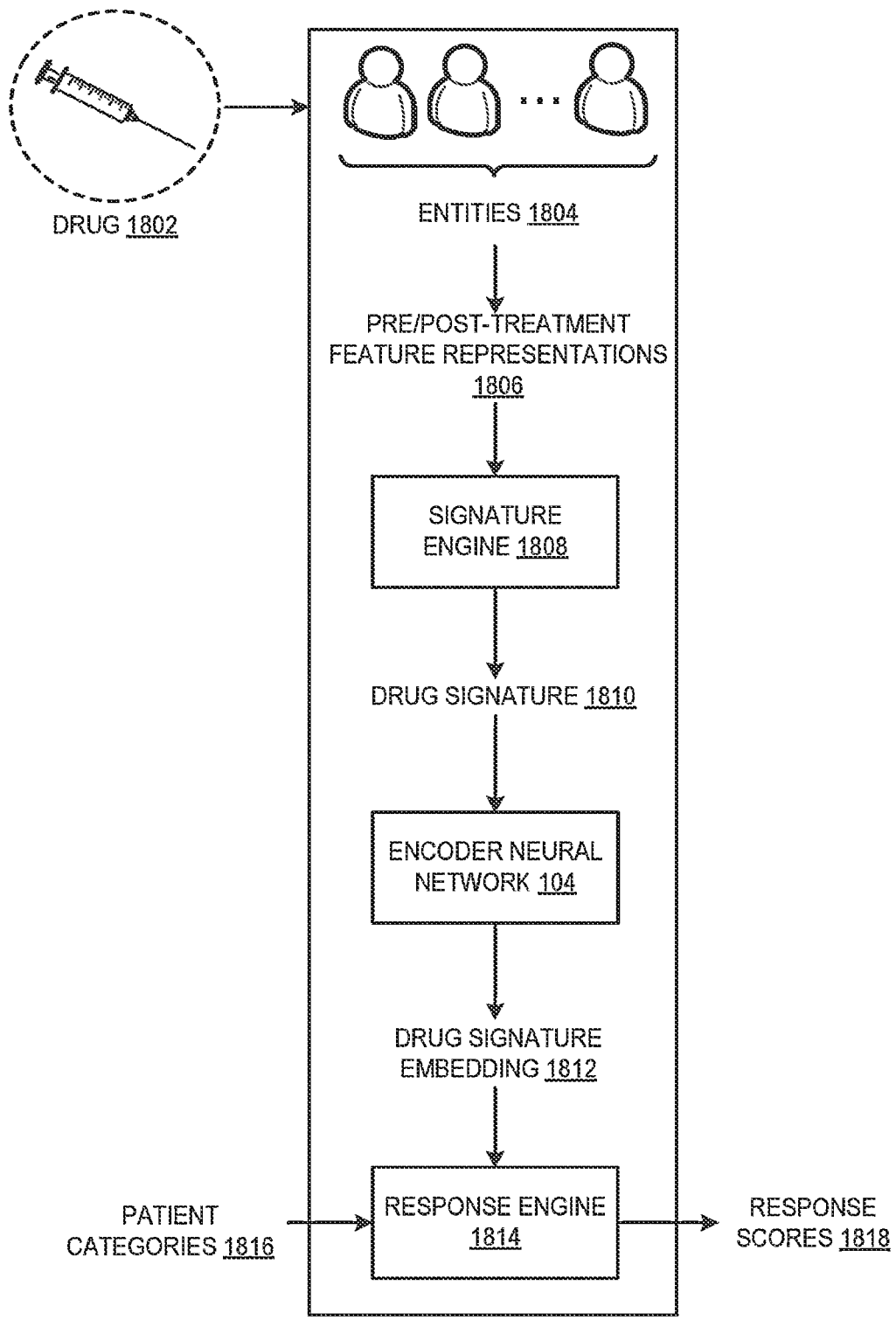
FIG. 18 shows an example response estimation system.

FIG. 18 shows an example response estimation system 1800. The response estimation system 1800 is an example of a system implemented as computer programs on one or more computers in one or more locations in which the systems, components, and techniques described below are implemented.

The response estimation system 1800 is configured to generate a respective response score 1818, relative to a drug 1802, for each patient category in a set of patient categories 1816. The response score 1818 for a patient category 1816 can characterize a predicted response of patients included the patient category to receiving the drug 1802.

The drug 1802 can be any appropriate substance that can be introduced into the body of a patient to achieve a desired physiological effect, e.g., the effect of treating one or more medical conditions in the patient, e.g., a psychiatric condition (e.g., depression, psychosis, or schizophrenia), cancer, diabetes, etc.

The "response" of a patient to receiving a drug can refer to any of a variety of changes in the condition of the patient as a result of receiving the drug. For example, the response of a patient to receiving a drug can characterize an amount of improvement in one or more symptoms of a medical condition in the patient that are achieved by administering the drug to the patient. As another example, the response of a patient to receiving a drug can characterize a level of side effects induced in the patient by the drug.

A response score 1818 for a patient category 1816 can (implicitly or explicitly) characterize any appropriate aspect of a predicted response of patients included in the patient category 1816 to receiving the drug. A few example applications of response scores 1818 generated by the response estimation system 1800 are described in more detail below.

A patient category 1816 can refer to a classification of patient, e.g., such that any patient can be classified as being included in a respective patient category from the set of patient categories 1816. For instance, a patient can be classified as being included in a patient category based on a set of multi-modal data characterizing the patient. Patients included in the same patient category may share similar features and characteristics. An example process for generating patient categories is described in detail with reference to FIG. 5, and an example process for classifying patients into patent categories is described in more detail with reference to FIG. 7A.

The response estimation system 1800 generates the response scores 1818 using a signature engine 1808, an encoder neural network 104, and a response engine 1814, which are each described in more detail next.

The signature engine 1808 is configured to receive, for each entity 1804 in a population of entities: (i) a respective "pre-treatment" feature representation 1806 of the entity 1804, and (ii) a respective "post-treatment" feature representation 1806 of the entity 1804.

Each entity 1804 can be, e.g., a cell, a collection of cells, or a patient. The population of entities can include any appropriate number of entities, e.g., one entity, 1,000 entities, or 10,000 entities. In some cases, the population of entities can cells corresponding to different tissue types, e.g., liver tissue, kidney tissue, brain tissue, etc.

Generally, a feature representation 1806 of an entity (e.g., a pre-treatment feature representation or a post-treatment feature representation) refers to a collection of features characterizing the entity that collectively represent data from one or more modalities. A feature representation 1806 of an entity 1804 can represent data from any appropriate modalities, e.g., an fMRI modality, a PET modality, a genomic data modality, a proteomic data modality, etc.

A feature representation 1806 of an entity can be represented, e.g., as an ordered collection of numerical values, e.g., a vector, matrix, or other tensor of numerical values. For convenience, the features in a feature representation 1806 for an entity can be understood as being indexed by a set of feature dimensions, where each feature dimension of the feature representation 1806 is associated with a value of a respective feature of the entity.

A pre-treatment feature representation 1806 of an entity refers to a representation of the entity that was captured (e.g., by one or more sensors) prior to the drug 1802 being administered to the entity. Conversely, a post-treatment feature representation 1806 of an entity refers to a representation of the entity that was captured (e.g., by one or more sensors) after the drug was applied to the entity (e.g., one minute, one hour, or one day after the drug was applied to the entity).

In some cases, for each entity 1804, the pre-treatment feature representation 1806 of the entity includes the same features as the post-treatment feature representation 1806 of the entity. However, the value of any given feature may differ between the pre-treatment feature representation 1806 and the post-treatment feature representation 1806 of an entity, e.g., at least in part because of the impact of the drug 1802 on the entity.

The drug 1802 can be administered to entities 1804 in the population of entities 1804 in any appropriate manner. In some cases, the entities are patients; a drug can be administered to a patient, e.g., by an injection, rectally, orally, or topically. In some cases, the entities are cells or collections of cells; a drug can be administered to a cell or a collection of cells, e.g., by introducing the drug into the environment of the cells, e.g., in vivo (e.g., in a biological environment) or in vitro (e.g., in an artificial environment, e.g., in a test tube or petri dish).

The signature engine 1808 is configured to process the pre-treatment and post-treatment feature representations 1806 of the entities 1804 in the population of entities to generate a drug signature 1810. The drug signature 1810 includes a respective impact score for each feature included in the feature representations 1806. The impact score for a feature characterizes an impact, caused by administering the drug 1802 to the entities 1804, on the value of feature measured for the entities 1804. For instance, the impact score for a first feature being higher than the impact score for a second feature can indicate that administering the drug has a higher impact on the value of the first feature than on the value of the second feature.

The drug signature 1810 can be represented as an ordered collection of numerical values (in particular, impact scores), e.g., as a vector, matrix, or other tensor of numerical values. The impact scores in the drug signature can be indexed by the same set of feature dimensions as the feature representations 1806; in particular, the impact score indexed by a feature dimension represents the impact score for the feature corresponding to the feature dimension.

The signature engine 1808 can process the pre-treatment and post-treatment feature representations 1806 to generate the drug signature 1810 in any of a variety of ways. For instance, to generate the drug signature, the signature engine 1808 can generate a respective "differential" feature representation for each entity 1804, e.g., as a difference between the pre-treatment feature representation 1806 of the entity 1804 and the post-treatment feature representation 1806 of the entity 1804. That is, the signature engine 1808 can generate a differential feature representation for an entity by element-wise subtracting the post-treatment feature representation for the entity from the pre-treatment representation for the entity (or vice versa).

The signature engine 1808 can generate a respective entity-specific drug signature for each entity 1804 based on the differential feature representation 1806 of the entity. A few example techniques for generating an entity-specific drug signature for an entity based on the differential feature representation for the entity are described next.

In some implementations, the signature engine 1808 can generate an entity-specific drug signature for an entity by element-wise dividing the differential feature representation for the entity by the pre-treatment feature representation for the entity. Thus, in this example, the impact score for each feature represents a fractional change in the value of the feature between the pre-treatment feature representation and the post-treatment feature representation.

In some implementations, the signature engine 1808 can generate an entity-specific drug signature for an entity by applying a non-linear activation function to the differential feature representation for the entity. The non-linear activation function can be, e.g., a sigmoid activation function, a soft-max activation function, or any other appropriate activation function.

In some implementations, the signature engine 1808 can define an entity-specific drug signature for an entity as being the differential feature representation of the entity.

The signature engine 1808 can combine the entity-specific drug signatures for the entities 1804 in population of entities 1804 to generate the overall drug signature 1810. For example, for each feature represented in the feature representations 1806, the signature engine 1808 can generate the impact score for the feature in the overall drug signature 1810 as a measure of central tendency of the impact scores for the feature in the entity-specific drug signatures. The measure of central tendency can be, e.g., a mean, a median, or a mode. In some implementations, where the population of entities includes only a single entity, the signature engine 1808 can designate the entity-specific drug signature for the entity as being the overall drug signature 1810.

The impact factors in the drug signature 1810 can correspond to features measured using any appropriate modalities. A few examples of possible modalities associated with impact factors in the drug signature 1810 are described next.

In some implementations, one or more of the impact factors in the drug signature 1810 are each associated with a feature measuring an expression level of a respective gene. An impact factor associated with a feature measuring an expression level of a gene characterizes an impact, caused by administering the drug to the entities 1804, on the expression level of the gene in the entities 1804.

In some implementations, one or more of the impact factors in the drug signature 1810 are each associated with a feature measuring an expression level of a respective protein. An impact factor associated with a feature measuring an expression level of a protein characterizes an impact, caused by administering the drug to the entities 1804, on the expression level of the protein in the entities 1804.

In some implementations, one or more of the impact factors in the drug signature 1810 are each associated with a feature measuring an amount of a radiotracer (e.g., a radioactive substance tagged to a drug) in a respective brain region. An impact factor associated with a feature measuring an amount of a radiotracer in a brain region characterizes an impact, caused by administering the drug to the entities 1804, on the amount of the radiotracer in the brain region of the entities 1804. In these implementations, the drug administered to the entities can be tagged with the radiotracer. The amount of the radiotracer in a brain region in the brain of a patient can be measured, e.g., from PET imaging of the brain of the patient. For example, the amount of a radiotracer in a brain region can be determined as a combination (e.g., an average or sum) of the intensity values of voxels included in the brain region in a PET image of the brain.

In some implementations, one or more of the impact factors in the drug signature 1810 are each associated with a feature measuring an amount of blood flow in a respective brain region. An impact factor associated with a feature measuring an amount of blood flow in a brain region characterizes an impact, caused by administering the drug to the entities 1804, on the amount of blood flow in the brain region in the entities 1804. In these implementations, the amount of blood flow in a brain region of the brain of a patient can be measured, e.g., from fMRI imaging of the brain of the patient. For example, the amount of blood flow in a brain region can be determined as a combination (e.g., an average or sum) of the intensity values of voxels included in the brain region in an fMRI image of the brain.

The encoder neural network 104 is a neural network that has been trained to process multi-modal data characterizing a patient to generate an embedding of the multi-modal data in a latent space. An example architecture of the encoder neural network is described above with reference to FIG. 2. Prior to being used by the archetype generation system 300B, the encoder neural network 104 can be jointly trained, along with a decoder neural network 108, e.g., by the training system 900 described with reference to FIG. 9.

The response estimation system 1800 generates a network input to the encoder neural network 104 based on the drug signature 1810. More specifically, the network input to the encoder neural network 104 includes an ordered collection of features that is indexed by a set of feature dimensions, i.e., such that each feature in the network input is indexed by a unique feature dimension in the set of feature dimensions. To generate the network input to the encoder neural network 104, the response estimation system 1800 associates each impact score in the drug signature with a respective feature dimension of the network input. For each feature dimension of the network input that is associated with a respective impact score in the drug signature 1810, the response estimation system 1800 defines the value of the feature dimension of the network input as being the value of the corresponding impact score from the drug signature 1810.

The response estimation system 1800 can associate the impact scores in the drug signature 1810 with corresponding feature dimensions of the network input to the encoder neural network 104 in accordance with predefined rules. For instance, in some cases, an impact score in the drug signature 1810 can correspond to a feature that is included in the network input. In these cases, the response estimation system 1800 can associate the impact score with the feature dimension of the corresponding feature in the network input.

In some cases, one or more of the impact scores in the drug signature 1810 can correspond to features from modalities that are not included in the network input to the encoder neural network 104. In these cases, the response estimation system 1800 can perform a cross-modal assignment of impact scores from the drug signature to corresponding feature dimensions of the network input. In particular, the response estimation system 1800 can assign an impact score for a feature corresponding to one modality in the drug signature 1810 to a feature dimension corresponding to a different modality in the network input to the encoder neural network 104.

For example, the drug signature 1810 may include an impact score for a PET feature measuring an amount of radiotracer in a brain region, while the network input to the encoder neural network 104 may not include any PET features. In this example, the response estimation system 1800 may associate the impact score for the PET feature of the brain region in the drug signature 1810 with a feature dimension of the network input that corresponds to an fMRI feature measuring blood flow in the brain region. Thus the response estimation system 1800 can perform a cross-modal assignment of an impact score corresponding to a PET feature to a feature dimension corresponding to an fMRI feature in the network input to the encoder neural network 104.

In some implementations, the number of impact scores in the drug signature 1810 may be less than the number of feature dimensions of the network input to the encoder neural network 104. Put another way, certain feature dimensions of the network input to the encoder neural network 104 may be "undefined," i.e., as a result of not be associated with corresponding impact scores from the drug signature 1810.

The response estimation system 1800 can address the issue of undefined feature dimensions in the network input to the encoder neural network 104 in a variety of possible ways. For example, the response estimation system 1800 can set the undefined feature dimensions of the network input to default values, e.g., zero. As another example, the response estimation system can set the value of each undefined feature dimension of the network input to a measure of central tendency (e.g., a mean, median, or mode) of feature values corresponding to the feature dimension for entities (e.g., cells or subjects) in a population of entities. As another example, the architecture of the encoder neural network may explicitly account for the possibility that the values of one or more feature dimensions are undefined. For instance, the encoder neural network architecture described with reference to FIG. 2 includes a respective subnetwork corresponding to each of multiple modalities. If the features corresponding to a particular modality are undefined in the network input, the encoder neural network disables the operations of the subnetwork corresponding to the modality, as described above with reference to FIG. 2.

The encoder neural network 104 processes the network input based on the drug signature 1810, in accordance with values of the encoder neural network parameters, to generate an embedding 1812 of the drug signature in a latent space.

The response engine 1814 is configured to process: (i) the drug signature embedding 1812, and (ii) data defining the patient categories 1816, to generate a respective response score 1818 for each patient category 1816. The response score 1818 for a patient category 1816 characterizes a predicted response of patients included in the patient category to the drug 1802. (That is, the response score for a patient category can, in some cases, implicitly or explicitly encode information relevant to the response of patients in the patient category to the drug).

Each patient category 1816 can be represented by a cluster of patient embeddings in the latent space, where each patient embedding corresponds to a respective patient and is generated by processing multi-modal data characterizing the patient using the encoder neural network 104. An example process for generating patient categories is described in more detail with reference to The response engine 1814 can generate the response score 1818 for a patient category 1816 in any of a variety of possible ways. A few example techniques for generating a response score 1818 for a patient category 1816 are described next.

In some implementations, the response engine 1814 defines the response score 1818 for a patient category 1816 as being a result of evaluating a similarity measure between: (i) the drug signature embedding 1812, and (ii) an embedding representing the patient category 1816. The embedding representing the patient category 1816 can be, e.g., a centroid of the patient embeddings in the patient category 1816, an average of the patient embeddings in the patient category 1816, or an archetype embedding representing the patient category 1816 (as described above with reference to FIG. 3B). The similarity measure can be, e.g., a cosine similarity measure, an $L_1$ similarity measure, an $L_2$ similarity measure, or any other appropriate similarity measure.

In some implementations, to generate the response score 1818 for a patient category 1816, the response engine 1814 evaluates a respective similarity measure between: (i) the drug signature embedding 1812, and (ii) each patient embedding included in the patient category 1816. The response engine 1814 can then define the response score 1818 as being a measure of central tendency of the similarity measures between the drug signature embedding 1812 and the patient embeddings included in the patient category 1816. The measure of central tendency can be, e.g., a mean, a median, or a mode. The similarity measure can be, e.g., a cosine similarity measure, an $L_1$ similarity measure, an $L_2$ similarity measure, or any other appropriate similarity measure.

In some cases, the response estimation system 1800 generates the response scores 1818 for the patient categories 1816 using the drug signature 1810, without embedding the drug signature 1810 in the latent space. A few example techniques for generating a response score 1818 for a patient category 1816 without embedding the drug signature 1810 in the latent space are described next.

In some implementations, the response engine 1814 defines the response score 1818 for a patient category 1816 as being a result of evaluating a similarity measure between: (i) the drug signature 1810, and (ii) a set of multi-modal data representing the patient category 1816. The set of multi-modal data representing the patient category 1816 can be, e.g., a centroid of multi-modal data tensors for patients included in the patient category 1816, an average of multi-modal data tensors for patients included in the patient category 1816, or a multi-modal data tensor corresponding to an archetype embedding representing the patient category 1816 (as described above with reference to FIG. 3B). The similarity measure can be, e.g., a cosine similarity measure, an $L_1$ similarity measure, an $L_2$ similarity measure, or any other appropriate similarity measure.

In some implementations, to generate the response score 1818 for a patient category 1816, the response engine 1814 evaluates a respective similarity measure between: (i) the drug signature 1810, and (ii) a respective multi-modal data tensor for each patient included in the patient category 1816. The response engine 1814 can then define the response score 1818 as being a measure of central tendency of the similarity measures between the drug signature 1810 and the multi-modal data tensors for the patients included in the patient category 1816. The measure of central tendency can be, e.g., a mean, a median, or a mode. The similarity measure can be, e.g., a cosine similarity measure, an $L_1$ similarity measure, an $L_2$ similarity measure, or any other appropriate similarity measure.

The response estimation system 1800 can use the response scores 1818 for the patient categories 1816 in any of a variety of possible applications. A few examples of possible applications of the response scores 1818 are described next.

In some implementations, the response estimation system 1800 uses the response scores 1818 to generate a ranking of the patient categories 1816. For instance, the response estimation system 1800 can generate a ranking of the patient categories 1816 from highest response score to lowest response score, or from lowest response score to highest response score.

In some implementations, the response estimation system 1800 uses the response scores 1818 to define a treatment criterion for selecting a course of medical treatment for a patient. For example, the treatment criterion may be that a patient is included in a patient category with a corresponding response score 1818 that satisfies (e.g., exceeds, or does not exceed) a threshold. The response estimation system 1800 can generate a recommendation that a patient should receive the drug 1802 based at least in part on whether the treatment criterion is satisfied for the patient.

Optionally, as an alternative to or in combination with generating response scores 1818 for patient categories 1816, the response estimation system 1800 can generate response scores 1818 for individual patients ("patient-specific" response scores). The response estimation system 1800 can define a patient-specific response score for a patient, e.g., as a measure of similarity between: (i) the drug signature embedding 1812, and (ii) a patient embedding for the patient. (The response estimation system 1800 can generate the patient embedding for the patient, e.g., by processing multi-modal data characterizing the patient using the encoder neural network 104, as described above). A patient-specific response score for a patient can characterize a predicted response of the patient to the drug 1802. A patient-specific response score for a patient can be used to define a treatment criterion for selecting a course of medical treatment for the patient, e.g., as described above with reference to response scores 1818 for patient categories 1816.

The encoder neural network 104 can be jointly trained along with a decoder neural network by a training system, e.g., the training system described with reference to FIG. 9. The training system can incorporate the drug signature embedding 1812 into the training of the encoder and decoder neural networks, as will be described next.

As described with reference to FIG. 9, the training system can jointly train the encoder neural network and the decoder neural network to optimize an objective function that includes a reconstruction loss that measures errors in reconstructed multi-modal data generated by the decoder neural network. The reconstruction loss can include multiple scaling factors that each scale a respective term in the reconstruction loss that measures an error in a corresponding proper subset of the feature dimensions of the reconstructed multi-modal data generated by the decoder neural network. Thus each scaling factor controls the relative importance of the error in a corresponding proper subset of the feature dimensions of the reconstructed multi-modal data to the calculation of the overall error in the reconstructed multi-modal data. An example of a reconstruction loss is provided in equation (11), where the $\{\beta_i\}_{i=1}^n$ represent the scaling factors.

The value of each scaling factor in the reconstruction loss can be set based on a relevance of the corresponding proper subset of the feature dimensions of the multi-modal data to a particular medical condition, e.g., a medical condition that is treated by the drug 1802. The training system can use the drug signature embedding 1812 to dynamically adjust one or more of the scaling factors in the reconstruction loss function during training. For instance, the training system can uniformly increase the values of the scaling factors, e.g., to increase the relative importance of the reconstruction loss relative to other parts of the objective function, e.g., the archetype loss, the clustering loss, or the prior loss. As another example, the training system can increase the values of certain designated scaling factors relative to other scaling factors, e.g., to increase the relative importance of the errors in certain subsets of the reconstructed multi-modal data to the calculation of the overall error in the reconstructed multi-modal data.

For example, at each of one or more training iterations, the training system can use the drug signature embedding 1812 to generate an influence score, e.g., that characterizes an influence of the scaling factors in the reconstruction loss on the semantic structure of the latent space. The training system can then increase one or more of the scaling factors in the reconstruction loss, over a sequence of training iterations, until the influence score satisfies (e.g., exceeds) a threshold.

The training system can generate the influence score at a training iteration in any of a variety of ways. For instance, to generate the influence score, the training system can generate a current drug signature embedding, i.e., in accordance with the current values of the encoder neural network parameters at the training iteration. The training system can then determine a respective similarity measure between the drug signature embedding and each of multiple "reference" embeddings in the latent space. The training system can then define the influence score, e.g., as the maximum of the similarity measures between the drug signature embedding and the reference embeddings.

The reference embedding can be any appropriate embeddings in the latent space. For instance, the reference embeddings can include a respective embedding representing each patient category in the latent space as of the training iteration. An embedding representing a patient category can be, e.g., a centroid of the patient embeddings in the patient category, an average of the patient embeddings in the patient category, or an archetype embedding representing the patient category (as described above with reference to FIG. 3B).

Intuitively, as the scaling factors for the reconstruction loss increase during training, the semantic structure of the latent space will adapt to increasingly emphasize information relevant to the medical condition treated by the drug 1802. As the latent space increasingly adapts to emphasize information relevant to the medical condition treated by the drug 1802, the reference embeddings in the latent space may increasingly reorient toward the drug signature embedding 1812 (which itself encodes information relevant to the medical condition, in particular, the relative impact of a drug treating the medical condition on respective patient features). The similarity between the drug signature embedding and the reference embeddings provides a measure of the influence of the scaled reconstruction loss on the semantic structure of the latent space.

Figure 19:
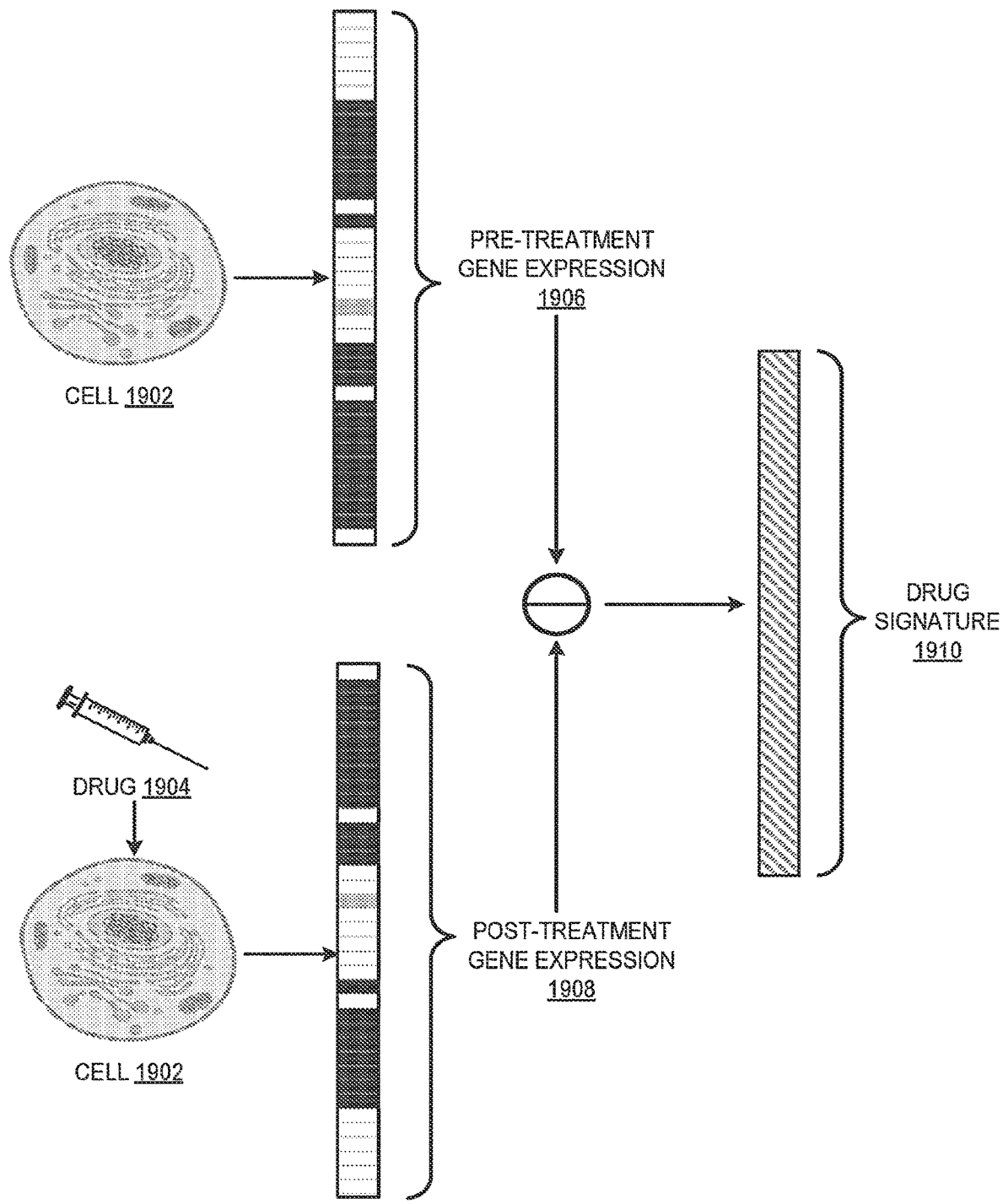
FIG. 19 illustrates an example of computing a drug signature based on gene expression in a cell.

FIG. 19 illustrates an example of computing a drug signature 1910 based on gene expression in a cell 1902. The pre-treatment feature representation of the cell 1902 includes the pre-treatment gene expression data 1906, e.g., that measures a respective level of expression of each of multiple genes in the cell prior the drug 1904 being applied to the cell 1902. The post-treatment feature representation of the cell 1902 includes the post-treatment gene expression data 1908, e.g., that measures a respective level of expression of multiple genes in the cell after the drug 1904 has been applied to the cell 1902. The drug signature 1910 for the drug 1904 can be based at least in part on a difference between the pre-treatment gene expression levels and the post-treatment gene expression levels, as described above in more detail with reference to FIG. 18.

Figure 20:
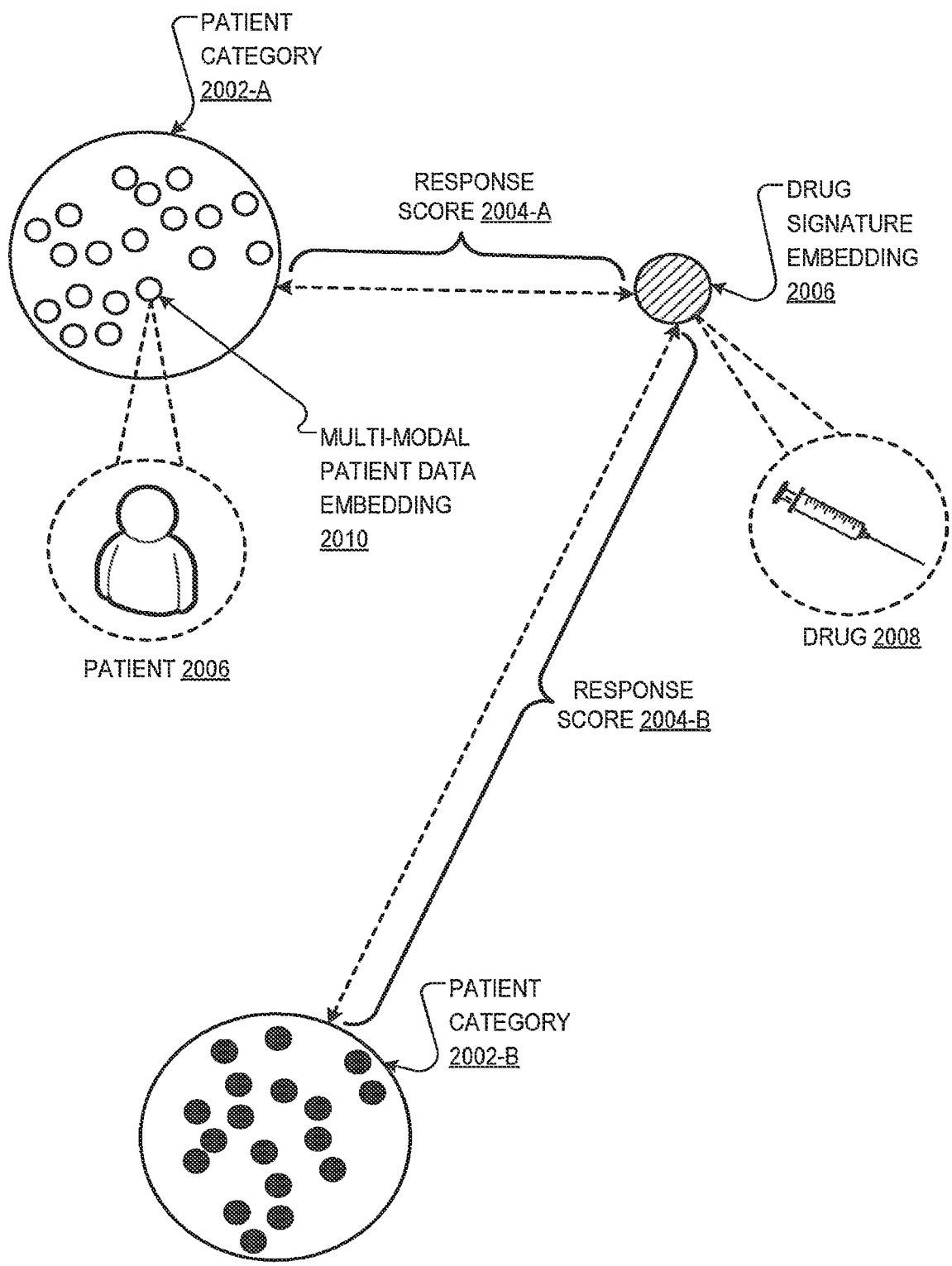
FIG. 20 illustrates examples of response scores for patient categories.

FIG. 20 illustrates examples of response scores for patient categories. In particular, FIG. 20 illustrates two patient categories 2002-A-B. Each patient category is represented by a respective cluster of patient embeddings in a latent space. Each patient embedding in the cluster of patient embeddings representing patient category 2002-A is represented by a light colored circle (e.g., 2010), and each patient embedding in the cluster of patient embeddings representing patient category 2002-B is represented by a dark colored circle. Each patient embedding corresponds to a respective patient and is generated by processing multi-modal data characterizing the patient using an encoder neural network. The drug signature embedding 2006 is an embedding of a drug signature for a drug 2008. The drug signature embedding 2006 is generated by processing a network input based on the drug signature using the encoder neural network. The drug signature embedding 2006 can be used to generate respective response scores 2004-A-B for the patient categories 2002-A-B. A response score for a patient category can characterize a predicted response of patients included in the patient category to the drug, as described in more detail above with reference to FIG. 18.

Figure 21:
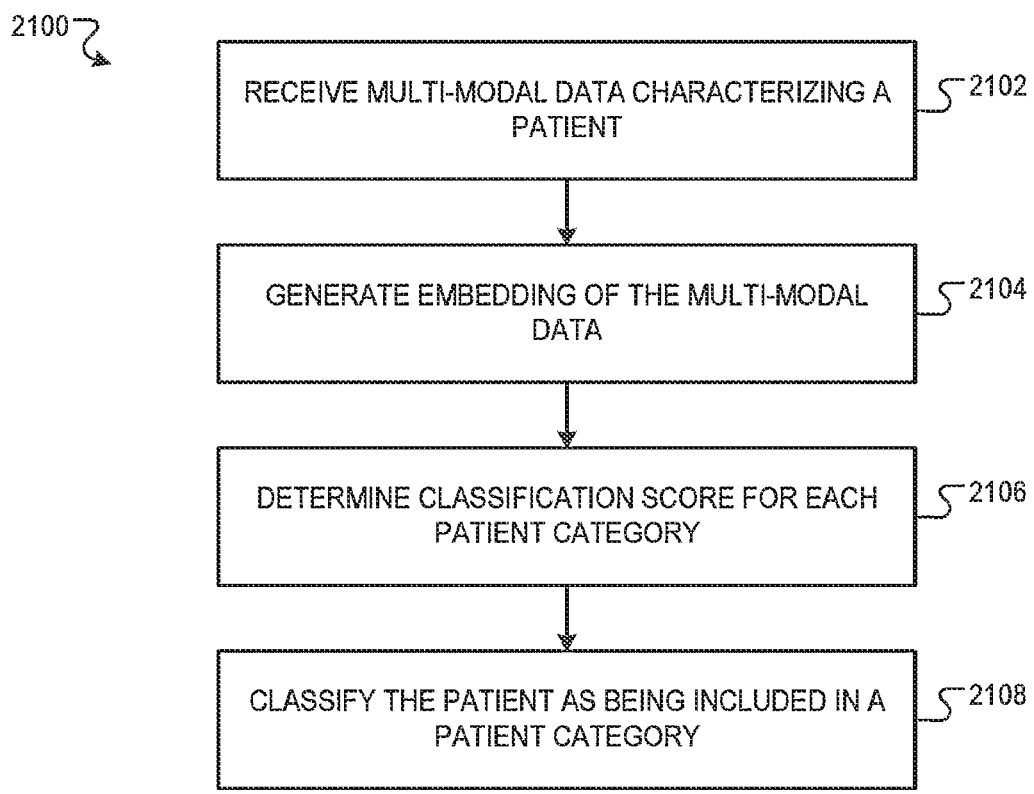
FIG. 21 is a flow diagram of an example process for classifying a patient as being included in a patient category.

FIG. 21 is a flow diagram of an example process 2100 for classifying a patient as being included in a patient category. For convenience, the process 2100 will be described as being performed by a system of one or more computers located in one or more locations. For example, a patient classification system, e.g., the patient classification system 700 of FIG. 7A, appropriately programmed in accordance with this specification, can perform the process 2100.

The system receives multi-modal data characterizing a patient (2102). The multi-modal data includes a respective feature representation for each of multiple modalities.

The system processes the multi-modal data characterizing the patient using an encoder neural network to generate an embedding of the multi-modal data characterizing the patient (2104). For example, the system can process the respective feature representation for each modality using a corresponding encoder subnetwork of the encoder neural network to generate a respective encoder subnetwork output. The system can then combine the encoder subnetwork outputs to generate the embedding of the multi-modal data characterizing the patient.

The system determines a respective classification score for each patient category in a set of patient categories based on the embedding of the multi-modal data characterizing the patient (2106). The set of patient categories can be determined by the patient clustering system, e.g., as described with reference to FIG. 5.

The system classifies the patient as being included in a corresponding patient category from the set of patient categories based on the classification scores (2108). For example, the system can classify the patient as being included in the patient category with the highest classification score.

Figure 22:
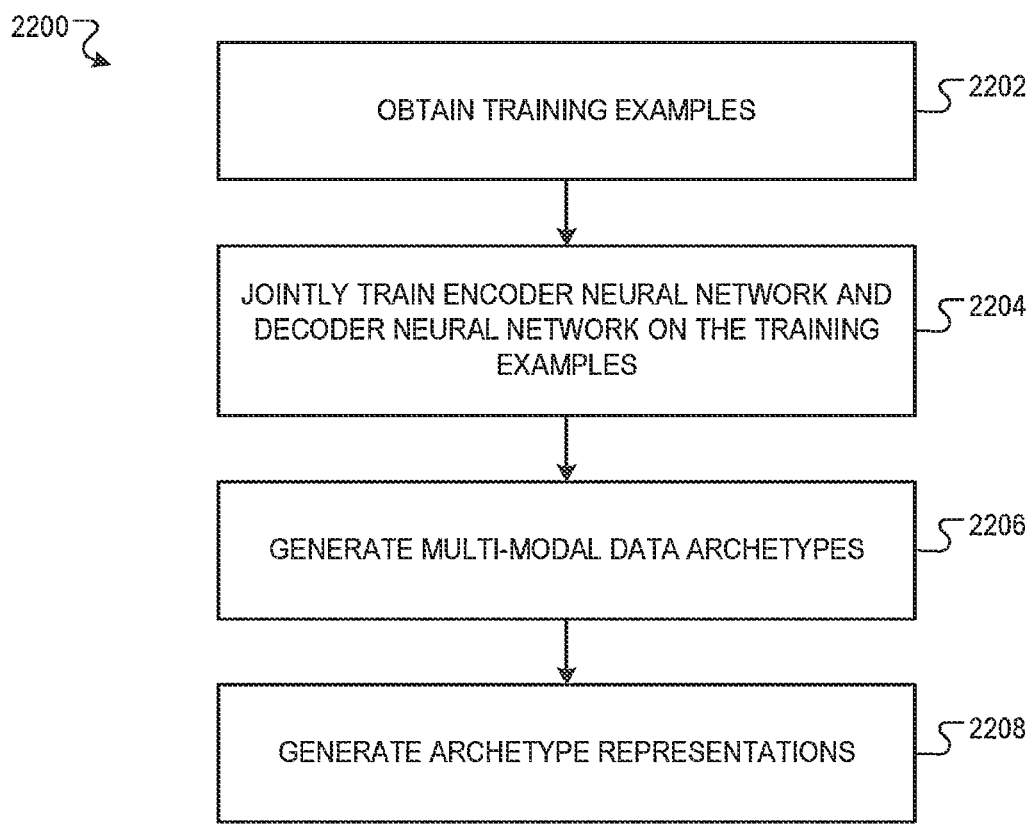
FIG. 22 is a flow diagram of an example process for generating a multi-modal data archetype and a corresponding archetype representation for each dimension of a latent space.

FIG. 22 is a flow diagram of an example process 2200 for generating a multi-modal data archetype and a corresponding archetype representation for each dimension of a latent space. For convenience, the process 2200 will be described as being performed by a system of one or more computers located in one or more locations. For example, an archetype generation system, e.g., the archetype generation systems 300A-B of FIG. 3, appropriately programmed in accordance with this specification, can perform the process 2200.

The system obtains a set of training examples (2202). Each training example corresponds to a respective patient and includes multi-modal data, having a set of feature dimensions, that characterizes the patient.

The system jointly trains an encoder neural network and a decoder neural network on the set of training examples (2204). The encoder neural network is configured to process input multi-modal data characterizing an input patient to generate an embedding of the input multi-modal data in a multi-dimensional latent space. The decoder neural network is configured to process the embedding of the input multi-modal data to generate a reconstruction of the input multi-modal data. An example process for training an encoder neural network and a decoder neural network on a set of training examples is described with reference to FIG. 23.

The system generates a set of multi-modal data archetypes (2206).

In some implementations, each multi-modal data archetype corresponds to a respective dimension of the latent space. In particular, for each dimension of the latent space, the system processes a predefined embedding that represents the dimension of the latent space using the decoder neural network to generate multi-modal data that defines the multi-modal data archetype for the dimension of the latent space.

In some implementations, the system processes the multi-modal training data from each training example using the encoder neural network to generate a set of multi-modal data embeddings in the latent space. The system processes the set of embeddings to generate a set of region parameters that define a region enclosing the set of embeddings in the latent space, e.g., the region can be a convex hull of the set of embeddings. The system then generates the set of multi-modal data archetypes based on: (i) the set of embeddings, and (ii) the region enclosing the set of embeddings in the latent space.

The system generates a respective archetype representation of each multi-modal data archetype (2208). To generate an archetype representation of a multi-modal data archetype, the system generates a respective intensity score for each feature dimension of the multi-modal data archetype based on: (i) a value of the feature dimension of the multi-modal data archetype, and (ii) a distribution defined by values of the feature dimension of multi-modal data included in the set of training examples. The archetype representation of the multi-modal data archetype includes the respective intensity score for each of the plurality of feature dimensions of the multi-modal data archetype.

Figure 23:
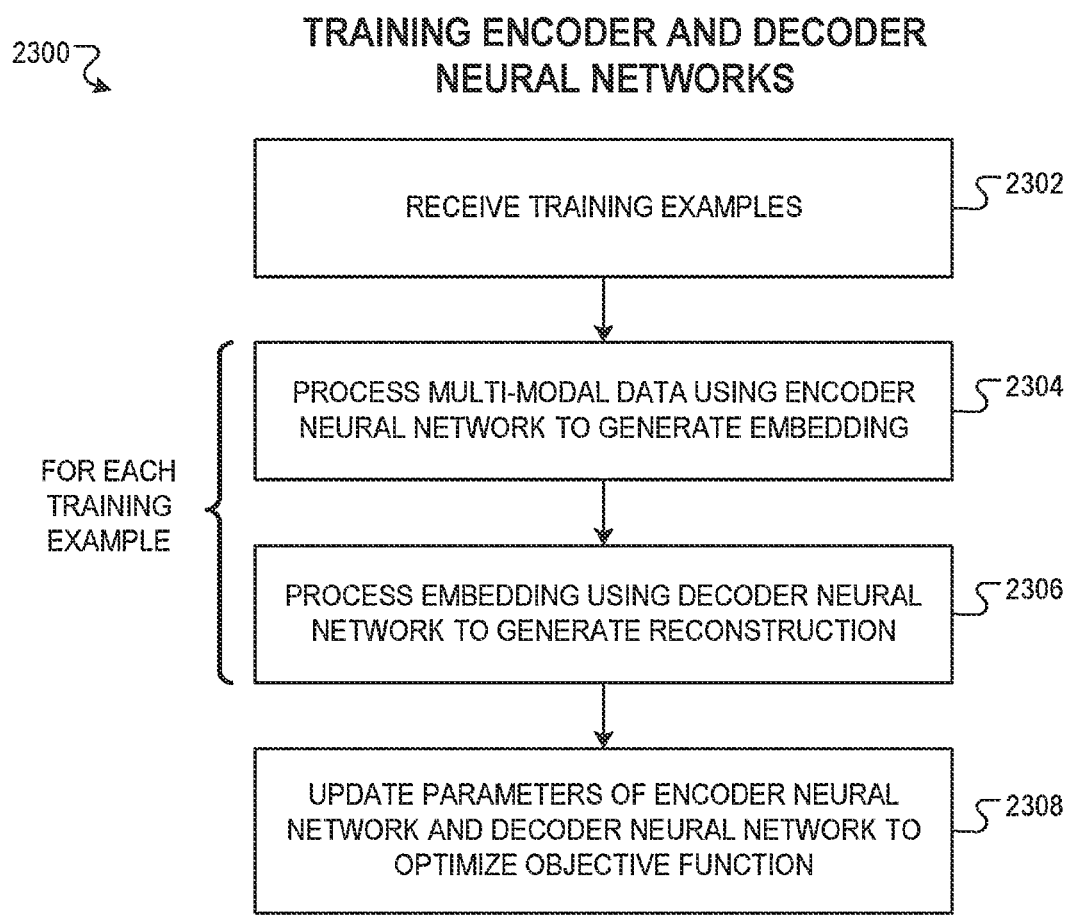
FIG. 23 is a flow diagram of an example process for jointly training an encoder neural network and a decoder neural network.

FIG. 23 is a flow diagram of an example process 2300 for jointly training an encoder neural network and a decoder neural network. For convenience, the process 2300 will be described as being performed by a system of one or more computers located in one or more locations. For example, a training system, e.g., the training system 900 of FIG. 9, appropriately programmed in accordance with this specification, can perform the process 2300.

The system receives a set of training examples (2302). For example, the system can sample the training examples from a set of training data that includes multiple training examples. Each training example corresponds to a respective patient and includes multi-modal data, having a set of feature dimensions, that characterizes the patient.

For each training example, the system processes the multi-modal data from the training example using the encoder neural network, in accordance with current values of the encoder parameters, to generate an embedding of the multi-modal data from the training example (2304).

For each training example, the system processes the embedding of the multi-modal data from the training example using the decoder neural network, in accordance with current values of the decoder parameters, to generate a reconstruction of the multi-modal data from the training example (2306).

The system updates the current values of the set of encoder parameters and the current values of the set of decoder parameters using gradients of an objective function (2308). The objective function includes a reconstruction loss function, and optionally one or more of: an archetype loss function, a clustering loss function, or a prior loss function.

The reconstruction loss function measures, for each training example, an error in the reconstruction of the multimodal data from the training example. In particular, the reconstruction loss function includes a set of scaling factors that each scale a respective term in the reconstruction loss function that measures an error in the reconstruction of a corresponding proper subset of the feature dimensions of the multi-modal data from the training example. Each of the scaling factors has a respective value that is based on a relevance of the corresponding proper subset of the feature dimensions of the multi-modal data from the training example to a particular medical condition. The system updates the current values of the set of encoder parameters and the current values of the set of decoder parameters using gradients of the reconstruction loss function.

In implementations where the objective function includes the archetype loss function, one or more dimensions of the latent space are "anchored" dimensions that are associated with a respective target multi-modal data archetype. For each anchored dimension of the latent space, the system processes a predefined embedding that represents the anchored dimension using the decoder neural network to generate multi-modal data that defines a predicted multi-modal data archetype corresponding to the anchored dimension. For each anchored dimension of the latent space, the archetype loss function measures an error between: (i) the predicted multi-modal data archetype corresponding to the anchored dimension, and (ii) the target multi-modal data archetype corresponding to the anchored dimension. The system updates the current values of the set of decoder parameters using gradients of the archetype loss function.

An example process for evaluating the clustering loss function is described in more detail with reference to FIG. 24.

Figure 24:
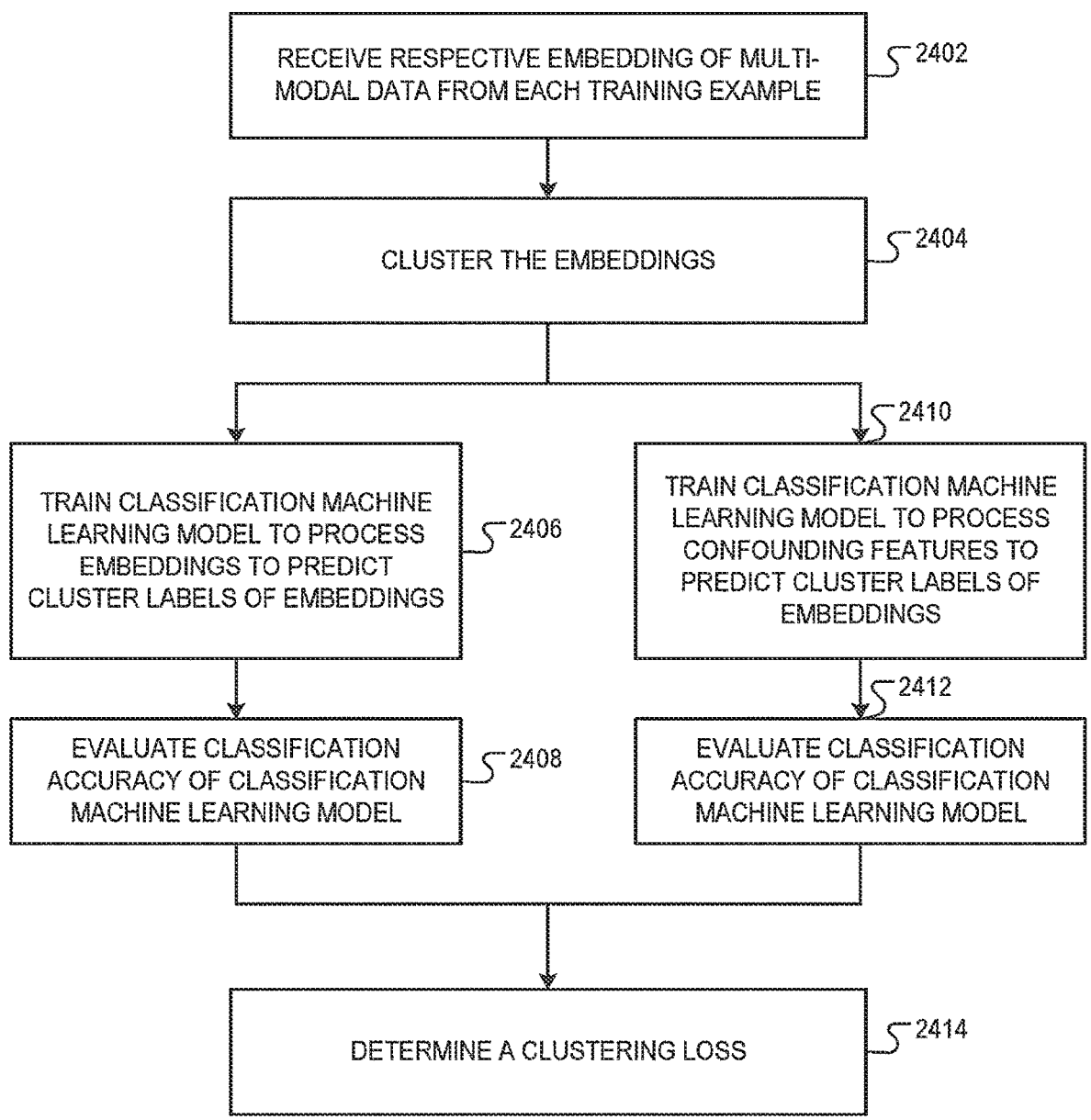
FIG. 24 is a flow diagram of an example process for determining a clustering loss during joint training of an encoder neural network and a decoder neural network.

FIG. 24 is a flow diagram of an example process 2400 for determining a clustering loss during joint training of an encoder neural network and a decoder neural network. For convenience, the process 2400 will be described as being performed by a system of one or more computers located in one or more locations. For example, a cluster hardening system, e.g., the cluster hardening system 1200 of FIG. 12, appropriately programmed in accordance with this specification, can perform the process 2400.

The system receives a respective embedding, generated by the encoder neural network, of the multi-modal data included in each training example (2402).

The system clusters the embeddings into multiple clusters of embeddings (2404). The system can cluster the embeddings by applying an appropriate clustering operation to the embeddings, e.g., a k-means clustering operation. Each embedding is associated with: (i) a cluster label that identifies a cluster that includes the embedding, and optionally, (ii) a set of confounding features.

In some implementations, the system designates a proper subset of the embeddings as being training embeddings, and trains a classification machine learning model to process each training embedding to predict the cluster label of the training embedding (2406). The system can then designate a proper subset of the embeddings as validation embeddings, and evaluate a classification accuracy of the classification machine learning model on a task of processing each validation embedding to predict the cluster label of the validation embedding (2408).

In some implementations, the system designates a proper subset of the embeddings as being training embeddings, and trains a classification machine learning model to process the set of confounding features corresponding to each training embedding to predict the cluster label of the training embedding (2410). The system can then designate a proper subset of the embeddings as validation embeddings, and evaluate a classification accuracy of the classification machine learning model on a task of processing the set of confounding features corresponding to each validation embedding to predict the cluster label of the validation embedding (2412).

The system determines a clustering loss based on the respective classification accuracy of each classification machine learning model (2414). For example, the system can determine the clustering loss as a linear combination of the classification accuracies of the classification machine learning models.

Figure 25:
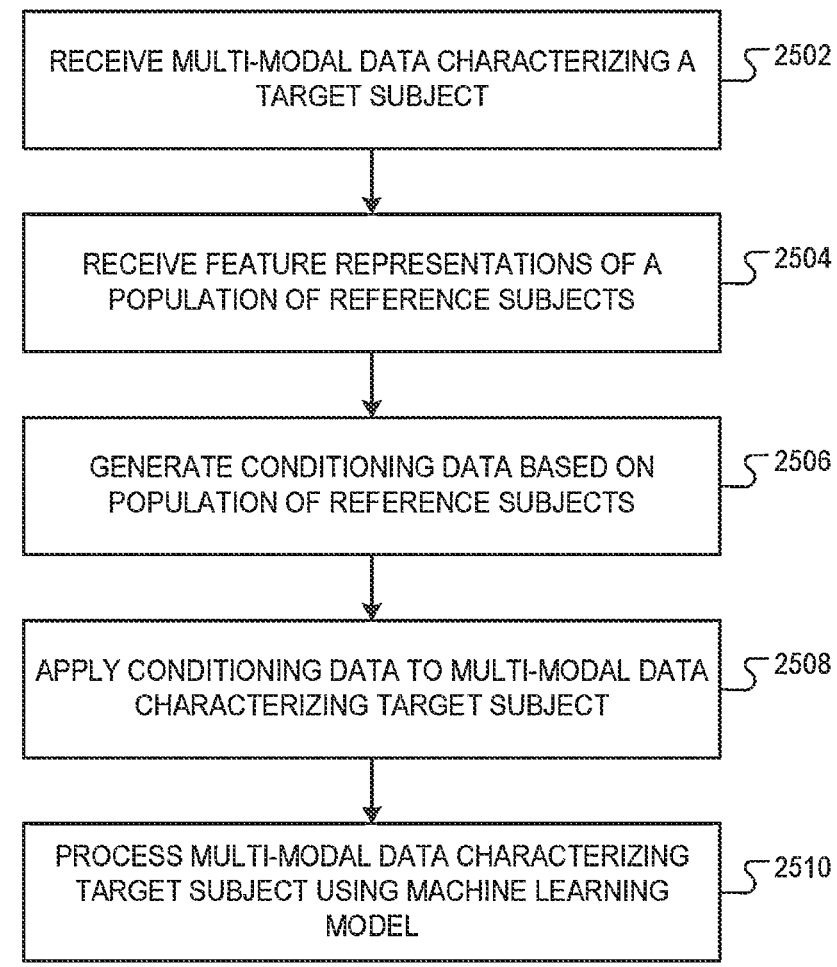
FIG. 25 is a flow diagram of an example process for conditioning multi-modal data characterizing a target subject based on conditioning data derived from a population of reference subjects.

FIG. 25 is a flow diagram of an example process 2500 for conditioning multi-modal data characterizing a target subject based on conditioning data derived from a population of reference subjects. For convenience, the process 2500 will be described as being performed by a system of one or more computers located in one or more locations. For example, a conditioning system, e.g., the conditioning system 1600 of FIG. 16, appropriately programmed in accordance with this specification, can perform the process 2500.

The system receives multi-modal data characterizing a target subject (2502). The multi-modal data characterizing the target subject includes a respective feature representation for each of a plurality of target modalities.

The system receives, for each reference subject in a population of reference subjects, a feature representation of the reference subject corresponding to a reference modality and having a plurality of feature dimensions (2504). In some cases, the system receives a pre-treatment feature representation of each reference subject captured before a medical treatment is applied to the reference subject, and a post-treatment feature representation of each reference subject captured after the medical treatment is applied to the reference subject.

The system generates the conditioning data based on the feature representations of the reference subjects (2506). For example, the system can determine, for each pair of feature dimensions including a first feature dimension and a second feature dimension, a respective correlation coefficient for the pair of feature dimensions that measures a correlation between: (i) a value of the first feature dimension in the feature representations of the reference subjects, and (ii) a value of the second feature dimension in the feature representations of the reference subjects.

The system applies the conditioning data to the multi-modal data characterizing the target subject (2508). For example, the system can pointwise multiply each of multiple feature dimensions of the multi-modal data by corresponding dimensions of the conditioning data.

After applying the conditioning data to the multi-modal data characterizing the target subject, the system processes the multi-modal data characterizing the target subject using a machine learning model to generate a machine learning model output for the target subject (2510). For example, the system can process the multi-modal data characterizing the target subject using the encoder neural network described with reference to FIG. 1.

Figure 26:
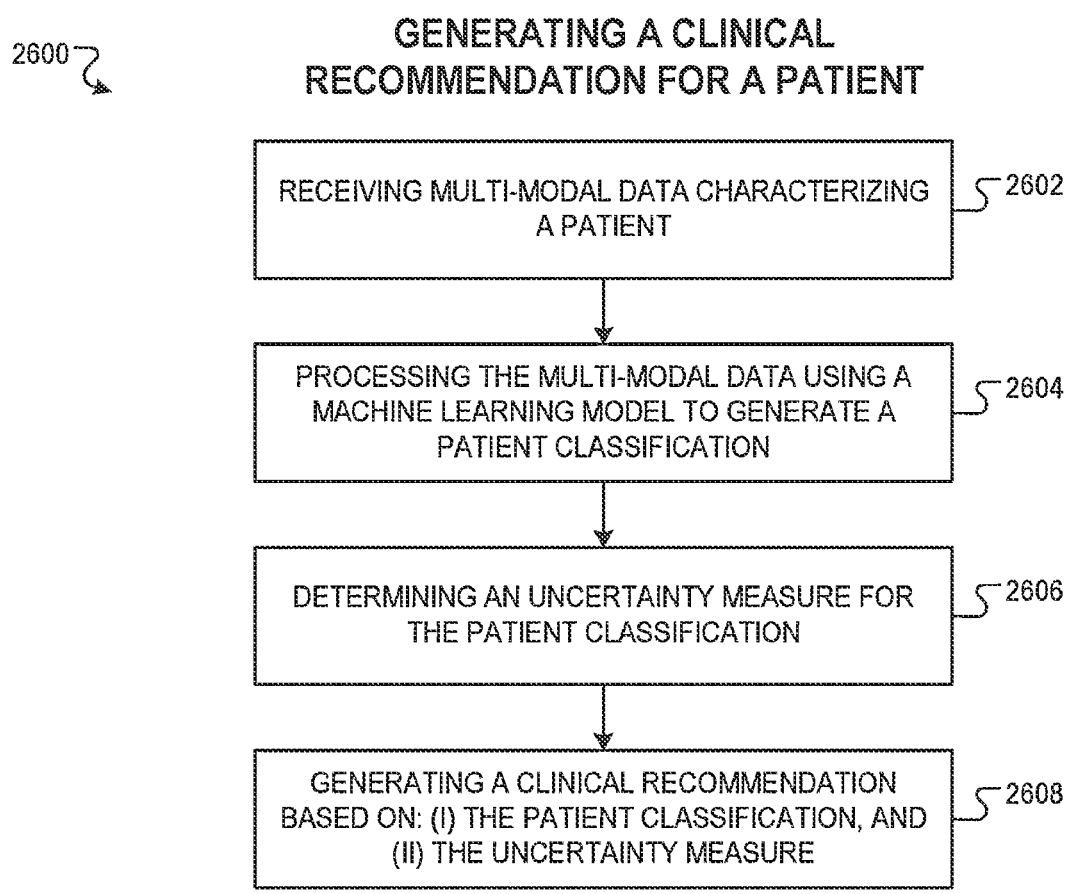
FIG. 26 is a flow diagram of an example process for generating a clinical recommendation for medical treatment of a patient.

FIG. 26 is a flow diagram of an example process 2600 for generating a clinical recommendation for medical treatment of a patient. For convenience, the process 2600 will be described as being performed by a system of one or more computers located in one or more locations. For example, a recommendation system, e.g., the recommendation system 800 of FIG. 8, appropriately programmed in accordance with this specification, can perform the process 2600.

The system receives multi-modal data characterizing a patient (2602). The multi-modal data includes a respective feature representation for each modality in a set of modalities.

The system processes the multi-modal data characterizing the patient using a machine learning model, in accordance with values of a set of machine learning model parameters, to generate a patient classification that classifies the patient as being included in a patient category from a set of patient categories (2604). For example, the system can generate, by the machine learning model, a respective classification score for each patient category in the set of patient categories. The system can then classify the patient as being included in the patient category based on the classification scores.

The system determines an uncertainty measure that characterizes an uncertainty of the patient classification generated by the machine learning model (2606). For example, the system can process the classification scores for the patient categories to identify a trust set for the patient. The trust set specifies one or more patient categories that form a proper subset of the set of patient categories, where the patient is predicted to be included in a patient category within the trust set with at least a threshold probability. The system determines the uncertainty measure based on the trust set for the patient.

The system generates a clinical recommendation for medical treatment of the patient based on: (i) the patient classification, and (ii) the uncertainty measure that characterizes the uncertainty of the patient classification (2608). For example, the system can evaluate a confidence criterion based at least in part on the uncertainty measure that characterizes the uncertainty of the patient classification. In response to determining that the confidence criterion is satisfied, the system can generate the clinical recommendation for the patient based on the patient classification.

Figure 27:
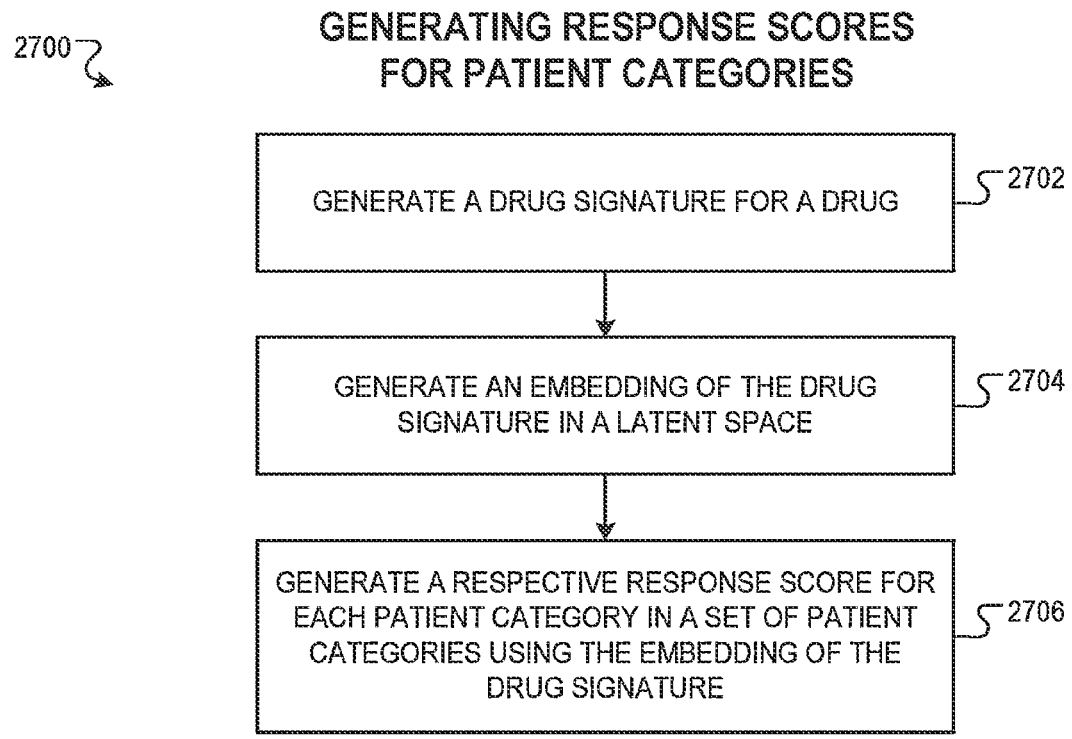
FIG. 27 is a flow diagram of an example process for generating a respective response score for each patient category in a set of patient categories.

FIG. 27 is a flow diagram of an example process 2700 for generating a respective response score for each patient category in a set of patient categories. For convenience, the process 2700 will be described as being performed by a system of one or more computers located in one or more locations. For example, a response estimation system, e.g., the response estimation system 1800 of FIG. 18, appropriately programmed in accordance with this specification, can perform the process 2700.

The system generates a drug signature for a drug (2702). The drug signature includes a respective impact score for each of multiple features. The impact score for a feature characterizes an impact, caused by administering a drug to one or more entities, on a value of the feature measured for the one or more entities.

The system generates an embedding of the drug signature in a latent space (2704). In particular, the system generates a network input to an encoder neural network based on the drug signature. The system processes the network input generated based on the drug signature using the encoder neural network to generate the embedding of the drug signature in the latent space.

The system processes: (i) the embedding of the drug signature in the latent space, and (ii) data defining a set of patient categories, to generate a set of response scores (2706). Each response score corresponds to a respective patient category and characterizes a predicted response of patients included in the patient category to the drug.

FIG. 28-33 show examples of experimental results achieved through applying the machine learning system described in this specification to multi-modal data for a population of patients, including at least some patients having amyotrophic lateral sclerosis (ALS). The multi-modal data for the patients included gene expression data and clinical data (e.g., demographic features, family history features, site of onset features, severity features, grip strength features, and respiratory function features).

Figure 28:
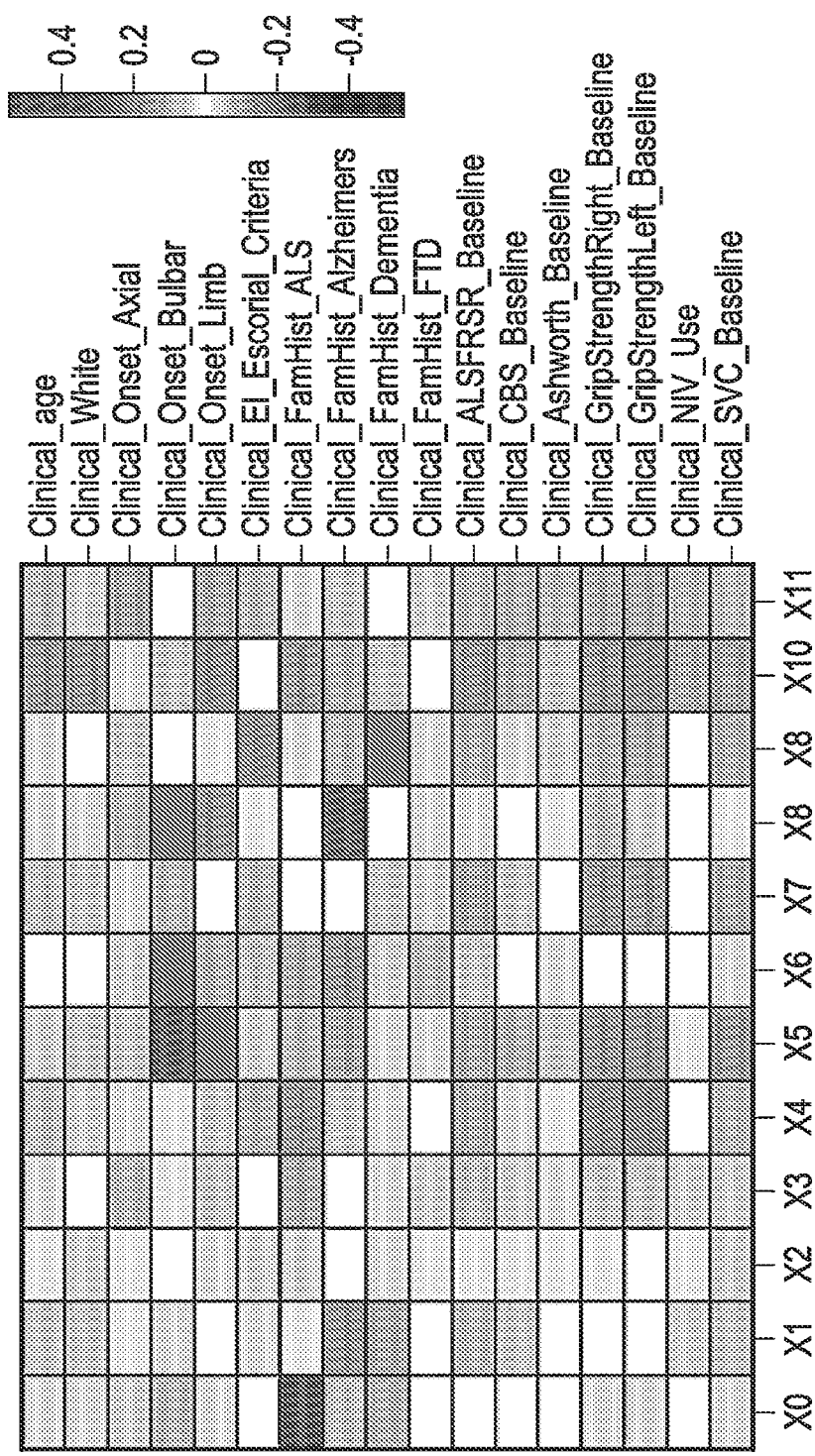
FIG. 28 shows an example of 12 multi-modal data archetypes relative to a set of multi-modal features.

FIG. 28 shows an example of 12 multi-modal data archetypes (labeled on the horizontal axis as "X0," "X1," ..., "X11") relative to a set of multi-modal features (labeled on the vertical axis as "Clinical_age," "Clinical_white," etc.). The shade of each cell shown in FIG. 28 represents an intensity score (e.g., as described with reference to FIG. 3) of a respective feature in a corresponding archetype.

Figure 29A:
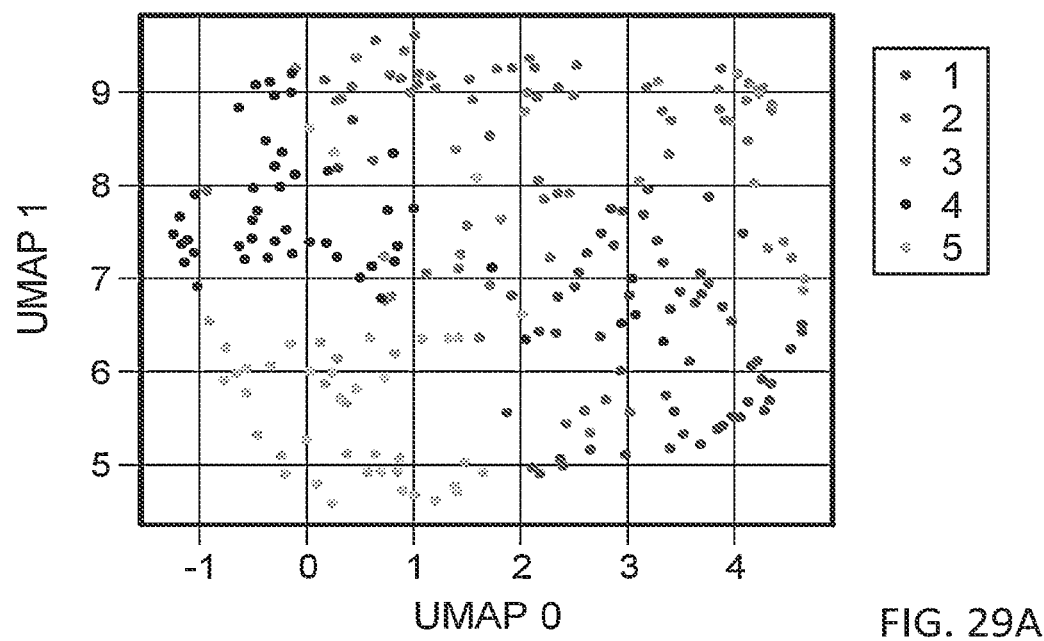
FIG. 29A-B show an example of clustering the patients in the population of patients.
Figure 29B:
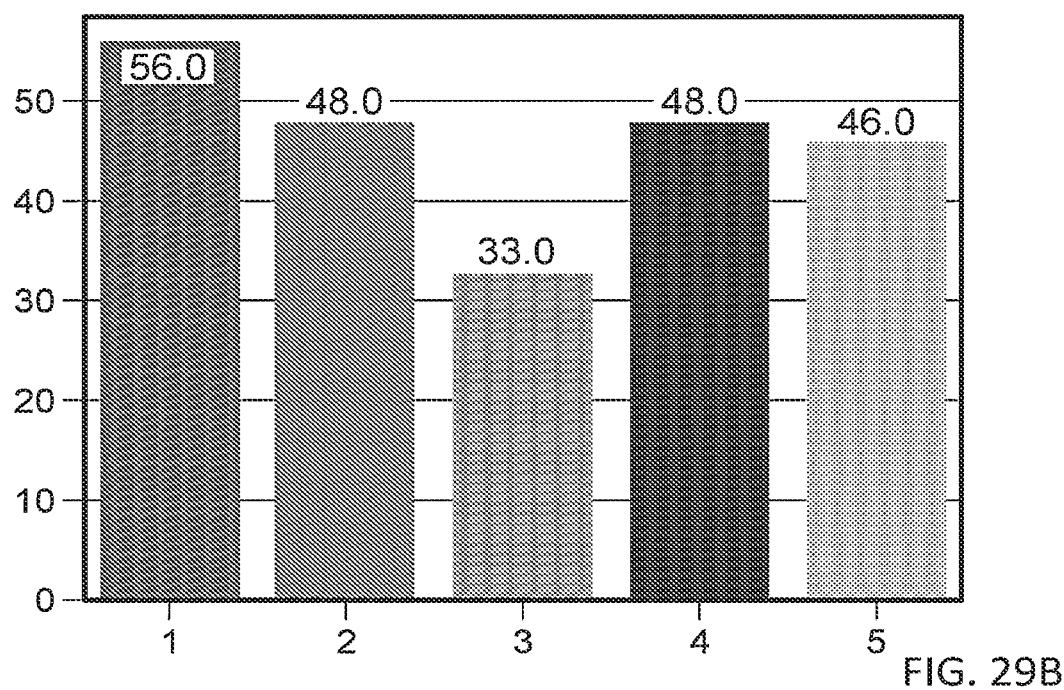

FIG. 29A-B show an example of clustering the patients in the population of patients. More specifically, FIG. 29A shows a two-dimensional visualization of the distribution of the patients in the respective clusters, and FIG. 29B shows the number of patients categorized as being included in each cluster.

Figure 30A:
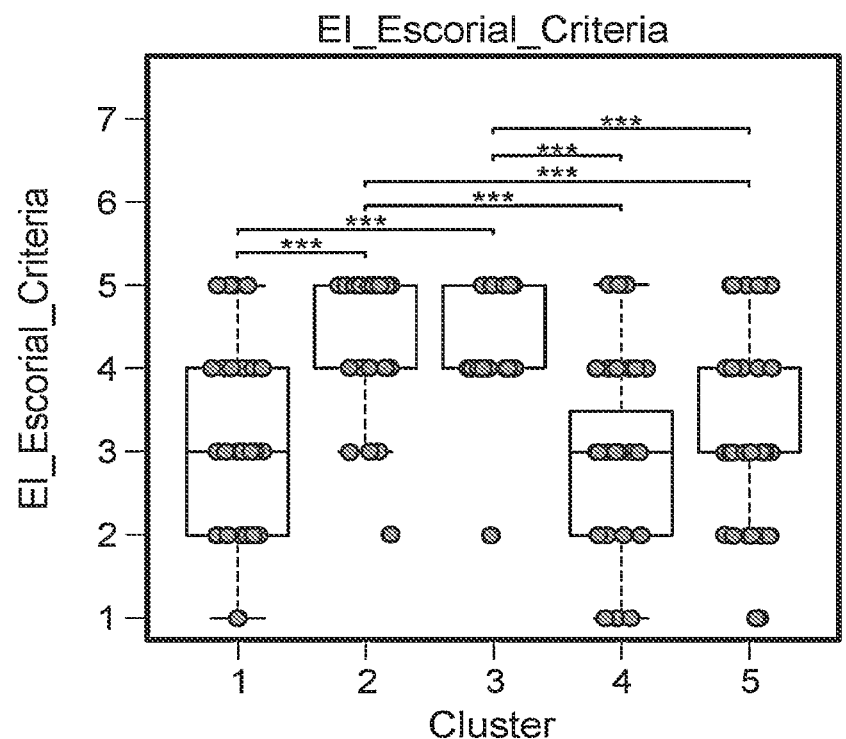
FIG. 30A-B and FIG. 31A-B show examples of the distribution of features for patients within clusters.
Figure 30B:
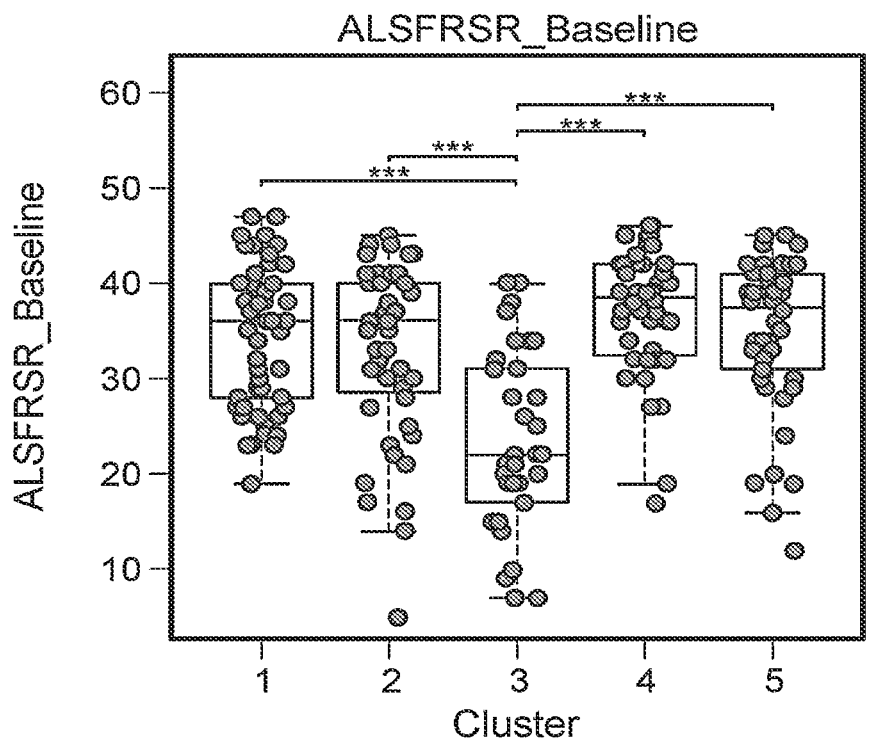
Figure 31A:
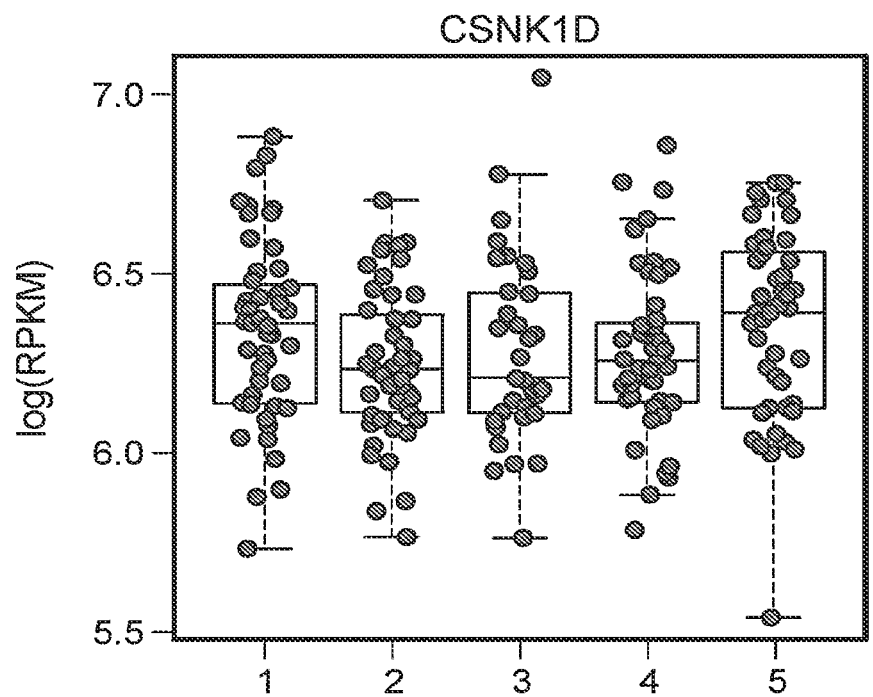
Figure 31B:
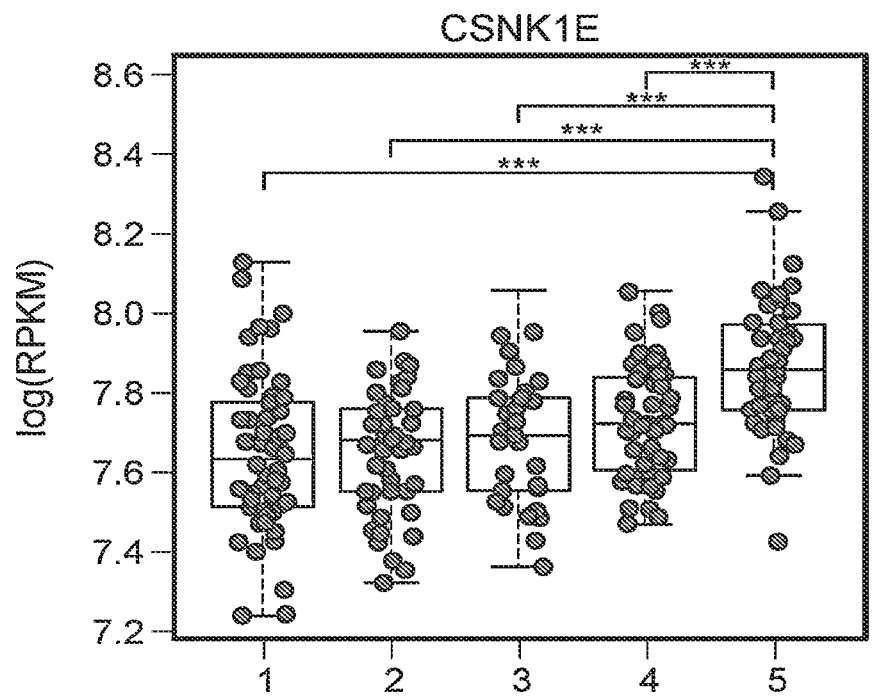

FIG. 30A-B and FIG. 31A-B show examples of the distribution of features for patients within clusters. More specifically, for each of five clusters, FIG. 30A shows a distribution of El Escorial criteria values for patients in the cluster, FIG. 30B shows a distribution of Revised Amyotrophic Lateral Sclerosis Functional Rating Scale (ALSFRS-R) values for patients in the cluster, FIG. 31A shows a distribution of CSNK1D gene expression for patients in the cluster, and FIG. 31B shows a distribution of CSNK1E gene expression for patients in the cluster.

FIG. 32-33 illustrate that the machine learning system is more likely to identify clusters of patients that differentiate along multiple feature dimensions when the machine learning system processes multi-modal patient data (in this case, a combination of gene expression data and clinical data) instead of unimodal patient data (in this case, gene expression data alone or clinical data alone).

Figure 32A:
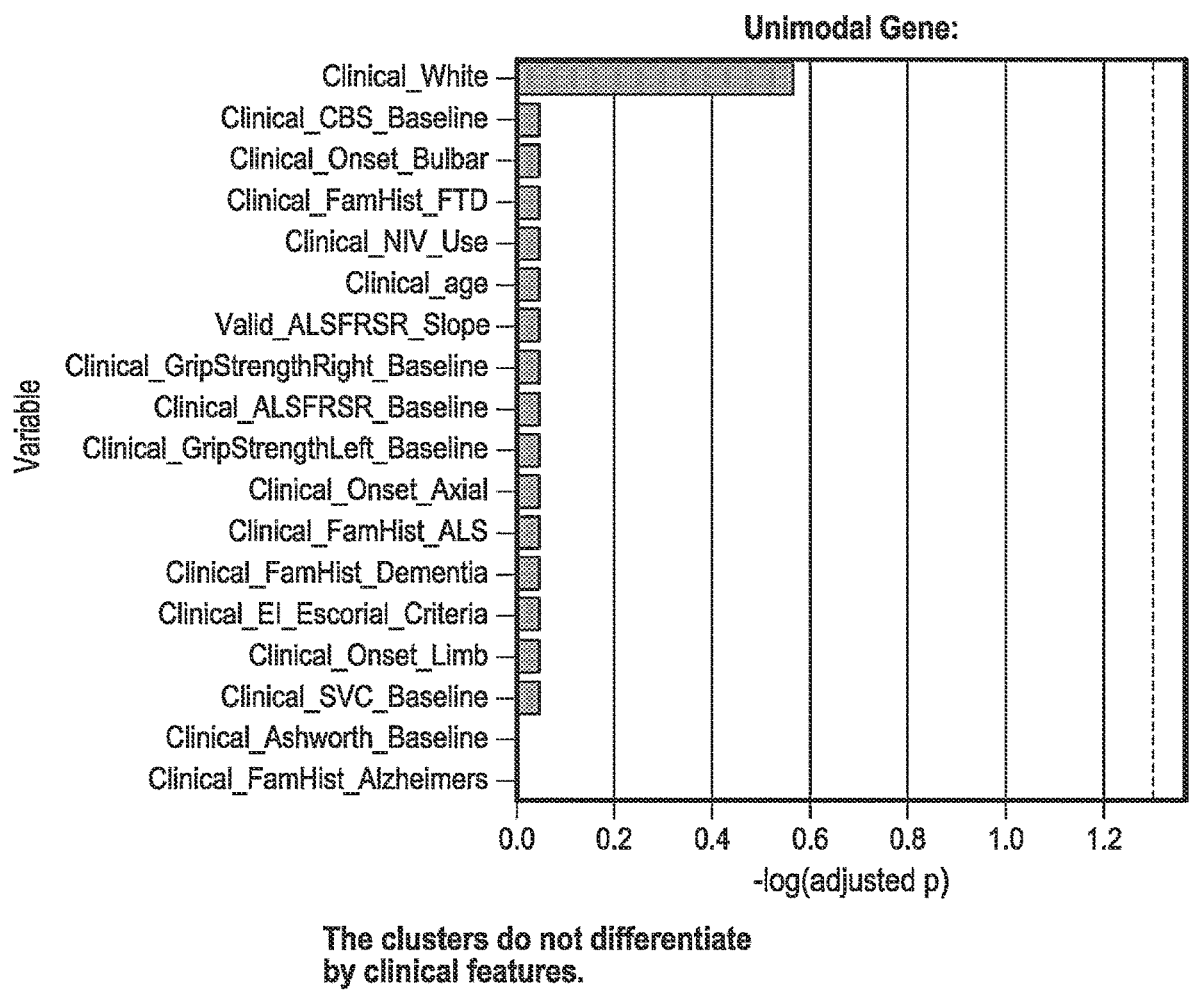
FIG. 32A-C show charts that illustrate the extent to which patient clusters identified by the machine learning system differentiate along clinical feature dimensions.

More specifically, FIG. 32A shows a chart that illustrates the extent to which patient clusters identified by the machine learning system differentiate along clinical feature dimensions when the machine learning system processes unimodal patient data, in particular, gene expression data alone. The length of the bar associated with each feature reflects the extent to which clusters can be differentiated with reference to that feature. It will be appreciated that, in this case, the clusters do not differentiate along clinical feature dimensions.

Figure 32B:
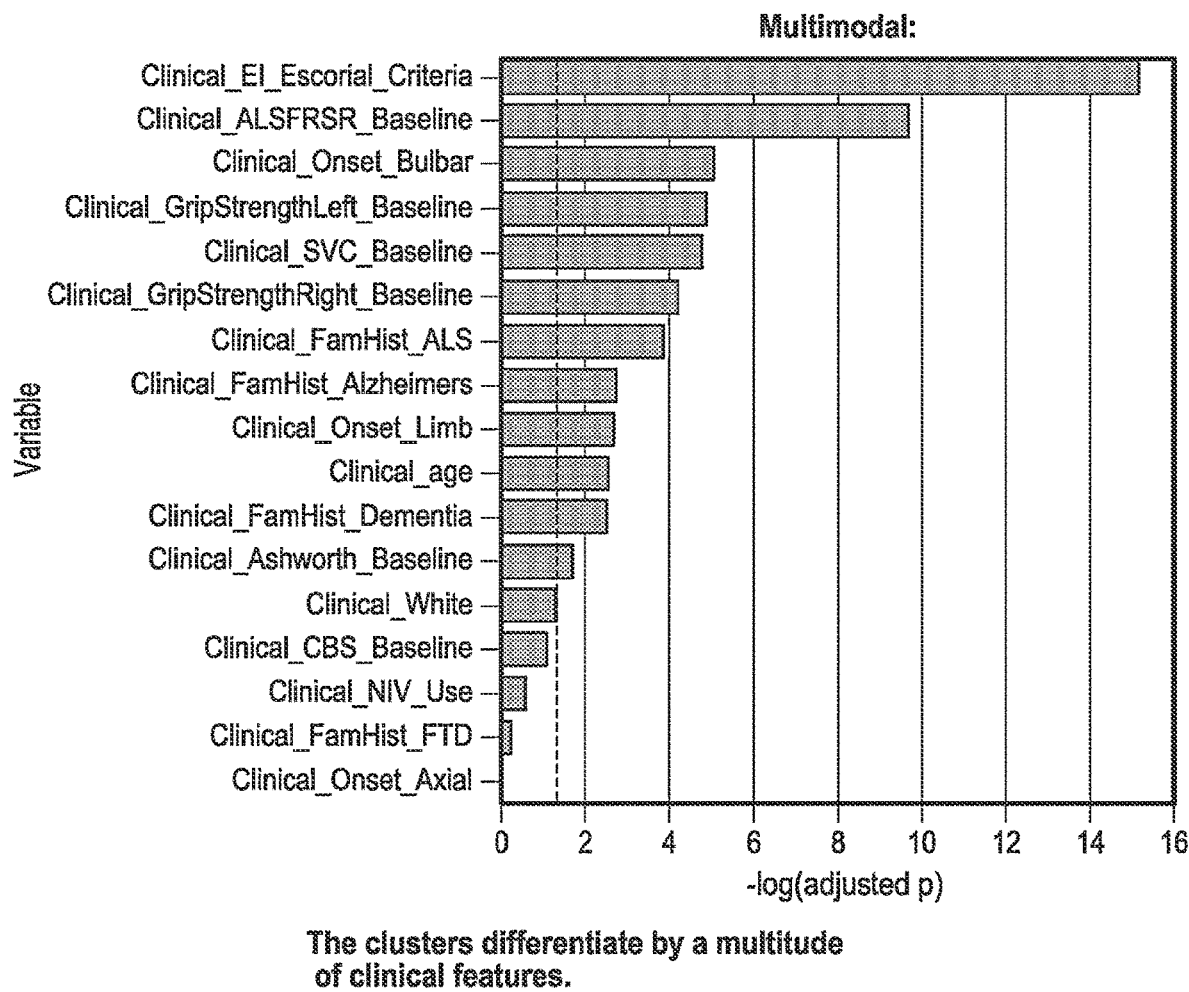

FIG. 32B shows a chart that illustrates the extent to which patient clusters identified by the machine learning system differentiate along clinical feature dimensions when the machine learning system processes multi-modal patient data, in particular, gene expression data and clinical data. The length of the bar associated with each feature reflects the extent to which clusters can be differentiated with reference to that feature. It will be appreciated that, in this case, the clusters are differentiated along many clinical feature dimensions.

Figure 32C:
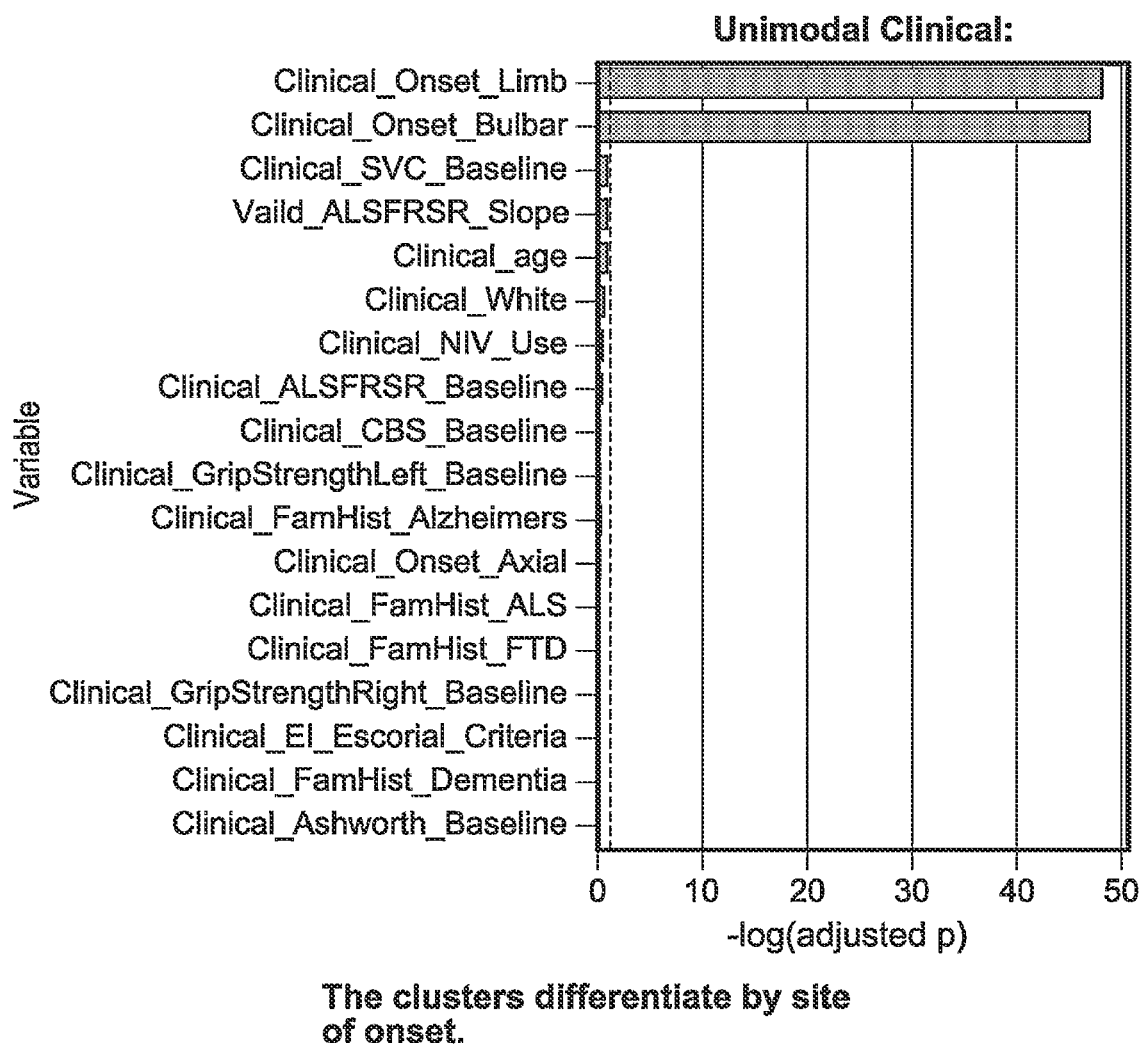

FIG. 32C shows a chart that illustrates the extent to which patient clusters identified by the machine learning system differentiate along clinical feature dimensions when the machine learning system processes unimodal patient data, in particular, clinical data alone. The length of the bar associated with each feature reflects the extent to which clusters can be differentiated with reference to that feature. It will be appreciated that, in this case, the clusters are differentiated along only a couple of clinical feature dimensions, in particular, feature dimension that indicate the site of onset of ALS.

Figure 33A:
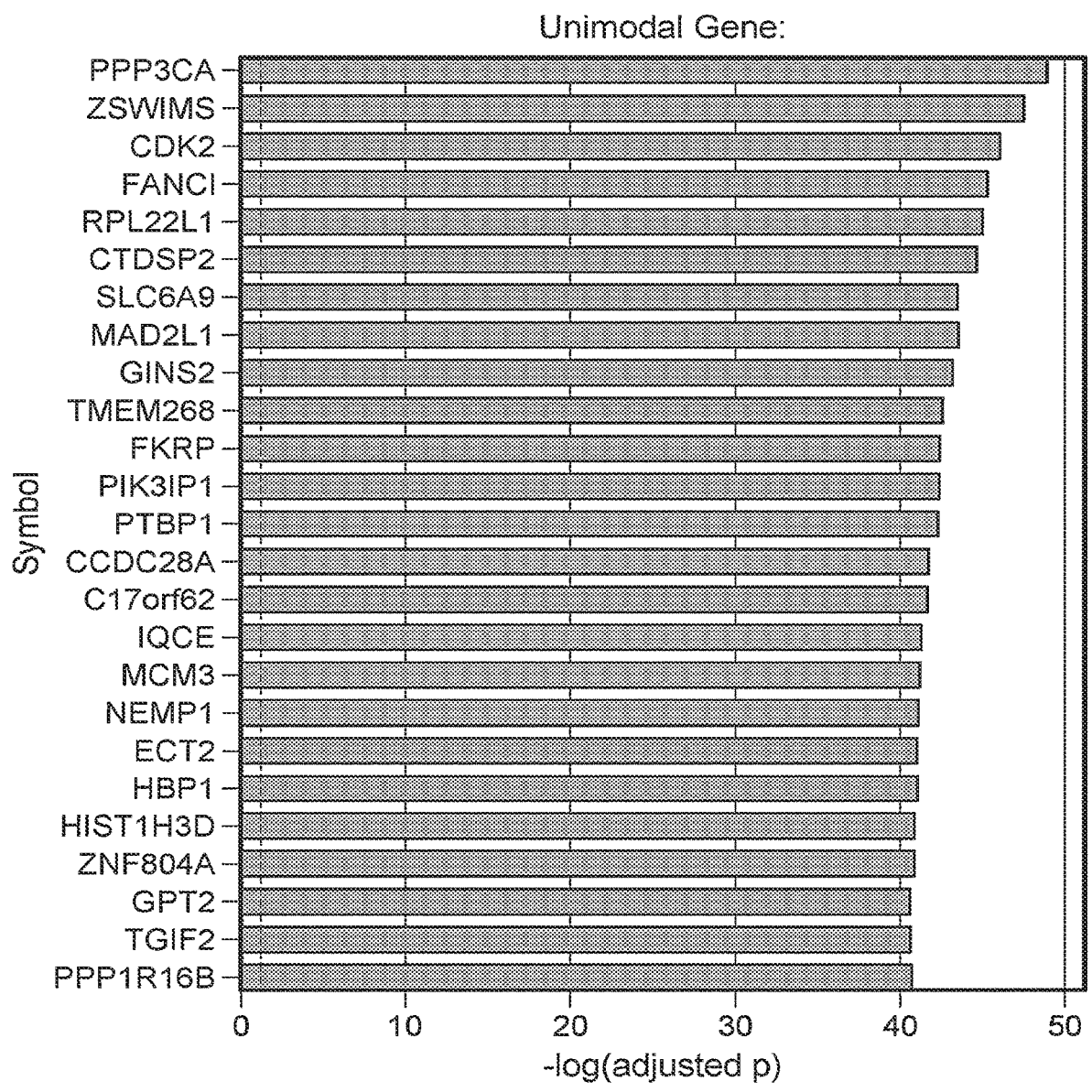
FIG. 33A-C show charts that illustrate the extent to which patient clusters identified by the machine learning system differentiate along gene expression feature dimensions.

FIG. 33A shows a chart that illustrates the extent to which patient clusters identified by the machine learning system differentiate along gene expression feature dimensions when the machine learning system processes unimodal patient data, in particular, gene expression data alone. The length of the bar associated with each feature reflects the extent to which clusters can be differentiated with reference to that feature. It will be appreciated that, in this case, the clusters are differentiated along many gene expression feature dimensions.

Figure 33B:
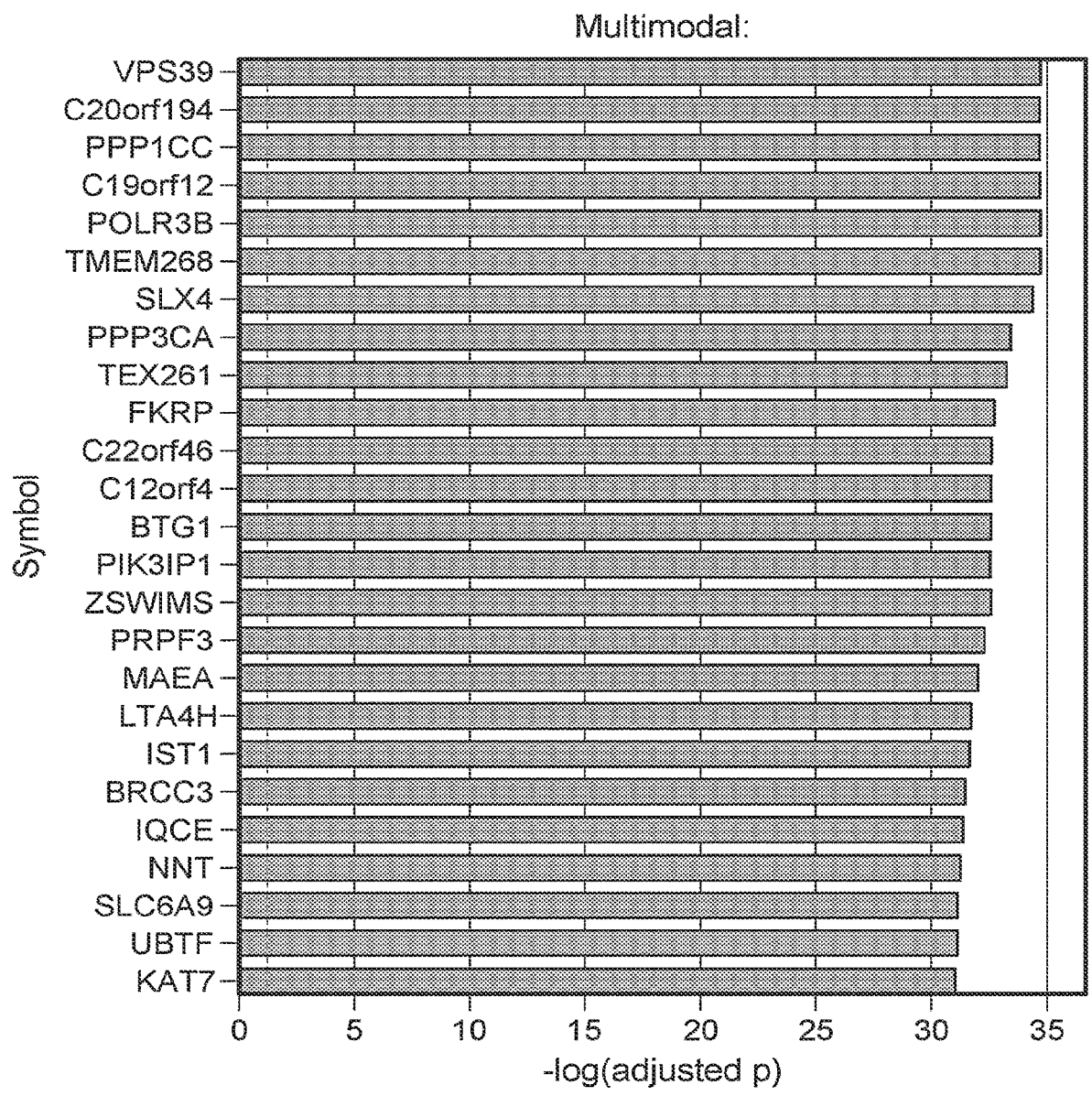

FIG. 33B shows a chart that illustrates the extent to which patient clusters identified by the machine learning system differentiate along gene expression feature dimensions when the machine learning system processes multi-modal patient data, in particular, gene expression data and clinical data. The length of the bar associated with each feature reflects the extent to which clusters can be differentiated with reference to that feature. It will be appreciated that, in this case, the clusters are differentiated along many gene expression feature dimensions.

Figure 33C:
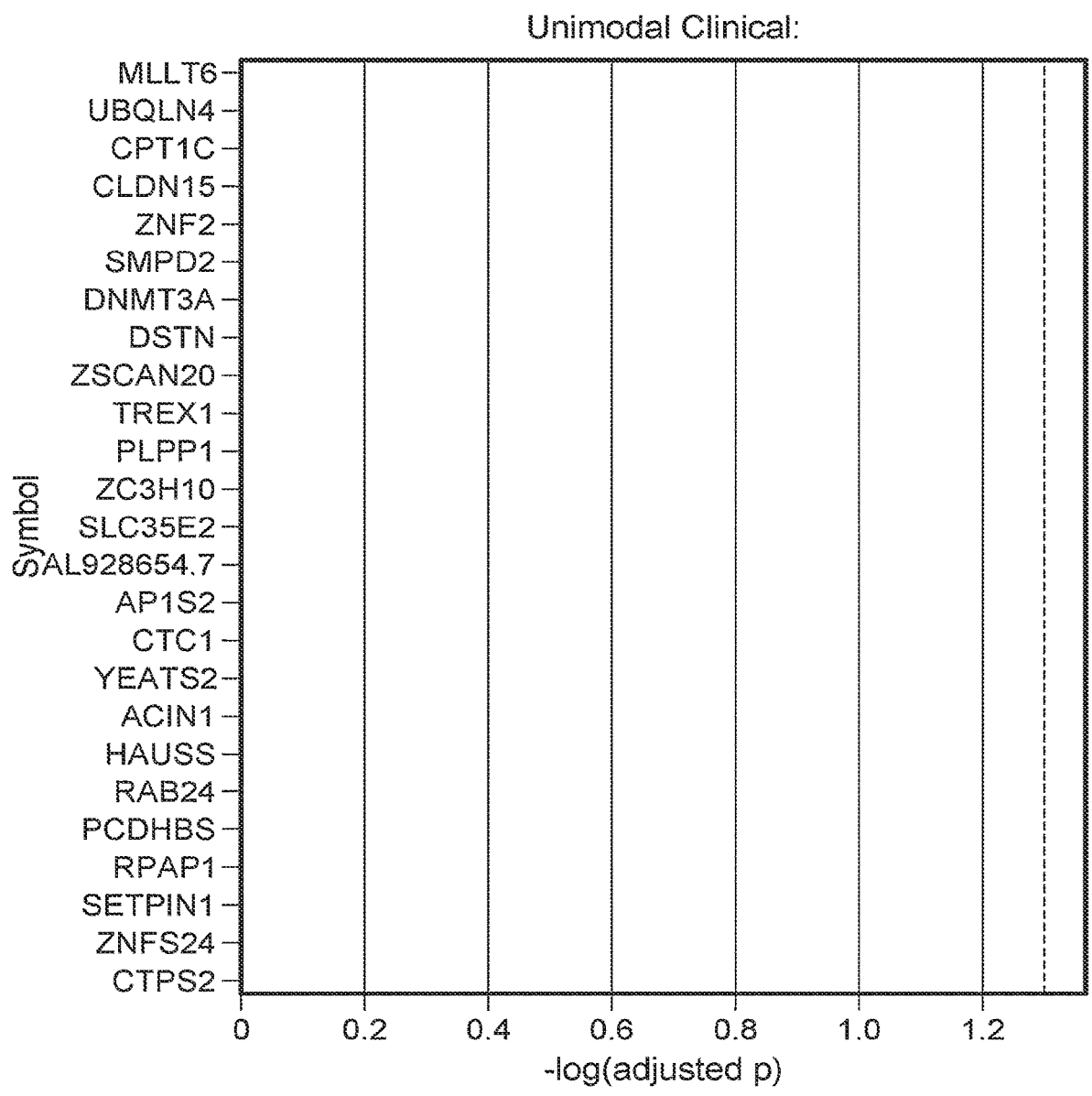

FIG. 33C shows a chart that illustrates the extent to which patient clusters identified by the machine learning system differentiate along gene expression feature dimensions when the machine learning system processes unimodal patient data, in particular, clinical data alone. The length of the bar associated with each feature reflects the extent to which clusters can be differentiated with reference to that feature. It will be appreciated that, in this case, the clusters do not differentiate along gene expression feature dimensions.

Comparing and contrasting FIG. 32A-C and FIG. 33A-C suggests that the machine learning system should process both gene expression data and clinical data in order to identify well-differentiated categories (sub-types) of patients with ALS. More generally, FIG. 32A-C and FIG. 33-A-C suggest that processing multi-modal patient data (as opposed to unimodal patient data) can enable the machine learning system to stratify patients into well-differentiated clusters. Clusters can be referred to as being "well-differentiated" if they are differentiated along many feature dimensions. Well-differentiated clusters are more likely to represent categories of patients that differentiate in clinically significant and reproducible ways, e.g., such that patients in the same cluster are more likely to share characteristics such as response and/or side effects from receiving a medical treatment, e.g., a drug.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using any appropriate machine learning framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:
1. A method comprising:
  generating a plurality of multi-modal data archetypes using an encoder neural network that has been jointly trained along with a decoder neural network, wherein:
    the encoder neural network is configured to process input multi-modal data characterizing an input patient to generate an embedding of the input multi-modal data in a multi-dimensional latent space;
    the decoder neural network is configured to process the embedding of the input multi-modal data to generate a reconstruction of the input multi-modal data; and
    generating the plurality of multi-modal data archetypes comprises:
      processing, for each patient in a population of patients, multi-modal data characterizing the patient using the encoder neural network to generate an embedding of the multi-modal data in the latent space,
> wherein the embeddings of multi-modal data characterizing the patients in the population of patients collectively define a set of embeddings in the latent space;

processing the set of embeddings in the latent space to generate a set of parameters defining a convex hull of the set of embeddings in the latent space;

processing: (i) the set of parameters defining the convex hull of the set of embeddings in the latent space, and (ii) the set of embeddings, to identify a proper subset of the embeddings in the set of embeddings as being archetype embeddings; and identifying the respective multi-modal data represented by each archetype embedding as a respective multi-modal data archetype.

2. The method of claim 1, further comprising generating a respective representation of each of the plurality of multi-modal data archetypes, comprising, for each multi-modal data archetype:

generating a respective intensity score for each of a plurality of feature dimensions of the multi-modal data archetype based on: (i) a value of the feature dimension of the multi-modal data archetype, and (ii) a distribution defined by values of the feature dimension of multi-modal data included in the plurality of training examples;

wherein the representation of the multi-modal data archetype comprises the respective intensity score for each of the plurality of feature dimensions of the multi-modal data archetype.

3. The method of claim 2, wherein for each of the plurality of feature dimensions of the multi-modal data archetype, the intensity score for the feature dimension characterizes a likelihood of the value of the feature dimension of the multi-modal data archetype under the distribution defined by values of the feature dimension of multi-modal data included in the plurality of training examples.

4. The method of claim 3, wherein for each of the plurality of feature dimensions of the multi-modal data archetype, determining the intensity score for the feature dimension comprises:

determining a mean and a standard deviation of the distribution defined by values of the feature dimension of multi-modal data included in the plurality of training examples; and determining the intensity score for the feature dimension using the mean and the standard deviation of the distribution defined by values of the feature dimension of multi-modal data included in the plurality of training examples.

5. The method of claim 2, further comprising providing the representations of the multi-modal data archetypes as explainability data that explains the dimensions of the latent space.

6. The method of claim 1, wherein jointly training the encoder neural network and the decoder neural network comprises, for each of a plurality of training examples:

processing multi-modal data from the training example using the encoder neural network, in accordance with current values of a set of encoder parameters, to generate an embedding of the multi-modal data from the training example;

processing the embedding of the multi-modal data from the training example using the decoder neural network, in accordance with current values of a set of decoder parameters, to generate a reconstruction of the multi-modal data from the training example; and updating the current values of the set of encoder parameters and the current values of the set of decoder parameters using gradients of a reconstruction loss function that measures an error in the reconstruction of the multi-modal data from the training example, wherein:

the reconstruction loss function comprises a plurality of scaling factors that each scale a respective term in the reconstruction loss function that measures an error in the reconstruction of a corresponding proper subset of a set of feature dimensions of the multi-modal data from the training example, and each of the plurality of scaling factors has a respective value that is based on a relevance of the corresponding proper subset of the feature dimensions of the multi-modal data from the training example to a particular medical condition.

7. The method of claim 6, wherein the respective value of each of the plurality of scaling factors is based on a relevance of the corresponding proper subset of the feature dimensions of the multi-modal data from the training example to diagnosing the particular medical condition.

8. The method of claim 6, wherein the respective value of each of the plurality of scaling factors is based on a relevance of the corresponding proper subset of the feature dimensions of the multi-modal data from the training example to a treatment for the particular medical condition.

9. The method of claim 6, wherein scaling factors corresponding to proper subsets of the feature dimensions of the multi-modal data that are more relevant to the particular medical condition have higher values than scaling factors corresponding to proper subsets of the feature dimensions of the multi-modal data that are less relevant to the particular medical condition.

10. The method of claim 1, wherein jointly training the encoder neural network and the decoder neural network comprises, for each latent dimension in a proper subset of a plurality of latent dimensions of the latent space:

obtaining multi-modal data that defines a target multi-modal data archetype, having a plurality of feature dimensions, that corresponds to the latent dimension;

processing a predefined embedding that represents the latent dimension using the decoder neural network to generate multi-modal data, having the plurality of feature dimensions, that defines a predicted multi-modal data archetype corresponding to the latent dimension; and updating values of a set of decoder parameters using gradients of a loss function that measures an error between: (i) the predicted multi-modal data archetype corresponding to the latent dimension, and (ii) the target multi-modal data archetype corresponding to the latent dimension.

11. The method of claim 1, wherein each of the plurality of multi-modal data archetypes includes a feature representation for a functional magnetic resonance imaging (fMRI) modality, and wherein the feature representation for the fMRI modality is derived from a series of fMRI images that each correspond to a respective time point in a sequence of time points and characterize blood flow in a brain of the patient at the time point.

12. The method of claim 1, wherein each of the plurality of multi-modal data archetypes includes a feature representation for an electroencephalography (EEG) modality, and wherein the feature representation of the EEG modality is derived from a plurality of voltage waveforms that are each measured by a respective electrode placed in proximity to a brain of the patient.

13. The method of claim 1, wherein each of the plurality of multi-modal data archetypes includes a feature representation for a genomics modality, and wherein the feature representation of the genomics modality is derived from data defining a sequence of nucleotides from a genome of the patient.

14. The method of claim 1, further comprising:
processing the plurality of multi-modal data archetypes to identify one or more dimensions to be removed from the latent space; and
removing the identified dimensions from the latent space.

15. The method of claim 14, wherein processing the plurality of multi-modal data archetypes to identify one or more dimensions to be removed from the latent space comprises, for each multi-modal data archetype:
determining whether a value of a feature dimension of the multi-modal data archetype satisfies a threshold; and
determining whether a corresponding dimension of the latent space should be removed based at least in part on the whether the value of the feature dimension of the multi-modal data archetype satisfies the threshold.

16. The method of claim 1, wherein processing: (i) the set of parameters defining the convex hull of the set of embeddings in the latent space, and (ii) the set of embeddings, to identify a proper subset of the embeddings in the set of embeddings as being archetype embeddings comprises:
determining a set of vertices of the convex hull of the set of embeddings in the latent space; and
identifying the archetype embeddings using the set of vertices of the convex hull of the set of embeddings in the latent space.

17. The method of claim 16, wherein identifying the archetype embeddings using the set of vertices of the convex hull of the set of embeddings in the latent space comprises, for each vertex:
identifying an embedding in the set of embeddings that has a minimum distance to the vertex from among the embeddings in the set of embeddings as being an archetype embedding corresponding to the vertex.

18. The method of claim 17, wherein for each vertex, identifying an embedding in the set of embeddings that has a minimum distance to the vertex comprises:
identifying an embedding in the set of embeddings that has a minimum Euclidean distance to the vertex.

19. A system comprising:
one or more computers; and
one or more storage devices communicatively coupled to the one or more computers, wherein the one or more storage devices store instructions that, when executed by the one or more computers, cause the one or more computers to perform operations comprising:
generating a plurality of multi-modal data archetypes using an encoder neural network that has been jointly trained along with a decoder neural network, wherein:
the encoder neural network is configured to process input multi-modal data characterizing an input patient to generate an embedding of the input multi-modal data in a multi-dimensional latent space;
the decoder neural network is configured to process the embedding of the input multi-modal data to generate a reconstruction of the input multi-modal data; and
generating the plurality of multi-modal data archetypes comprises:
processing, for each patient in a population of patients, multi-modal data characterizing the patient using the encoder neural network to generate an embedding of the multi-modal data in the latent space,
wherein the embeddings of multi-modal data characterizing the patients in the population of patients collectively define a set of embeddings in the latent space;
processing the set of embeddings in the latent space to generate a set of parameters defining a convex hull of the set of embeddings in the latent space;
processing: (i) the set of parameters defining the convex hull of the set of embeddings in the latent space, and (ii) the set of embeddings, to identify a proper subset of the embeddings in the set of embeddings as being archetype embeddings; and
identifying the respective multi-modal data represented by each archetype embedding as a respective multi-modal data archetype.

20. One or more non-transitory computer storage media storing instructions that when executed by one or more computers cause the one or more computers to perform operations comprising:
generating a plurality of multi-modal data archetypes using an encoder neural network that has been jointly trained along with a decoder neural network, wherein:
the encoder neural network is configured to process input multi-modal data characterizing an input patient to generate an embedding of the input multi-modal data in a multi-dimensional latent space;
the decoder neural network is configured to process the embedding of the input multi-modal data to generate a reconstruction of the input multi-modal data; and
generating the plurality of multi-modal data archetypes comprises:
processing, for each patient in a population of patients, multi-modal data characterizing the patient using the encoder neural network to generate an embedding of the multi-modal data in the latent space,
wherein the embeddings of multi-modal data characterizing the patients in the population of patients collectively define a set of embeddings in the latent space;
processing the set of embeddings in the latent space to generate a set of parameters defining a convex hull of the set of embeddings in the latent space;
processing: (i) the set of parameters defining the convex hull of the set of embeddings in the latent space, and (ii) the set of embeddings, to identify a proper subset of the embeddings in the set of embeddings as being archetype embeddings; and
identifying the respective multi-modal data represented by each archetype embedding as a respective multi-modal data archetype.

* * * * *